US006180098B1

(12) United States Patent
Christian

(10) Patent No.: US 6,180,098 B1
(45) Date of Patent: Jan. 30, 2001

(54) RECOMBINANT HELICOVERPA BACULOVIRUSES EXPRESSING HETEROLOGOUS DNA

(75) Inventor: Peter Daniel Christian, Macgregor (AU)

(73) Assignee: Commonwealth Scientific and Industrial Research Organisation, Campbell (AU)

( * ) Notice: Under 35 U.S.C. 154(b), the term of this patent shall be extended for 0 days.

(21) Appl. No.: 09/029,213

(22) PCT Filed: Aug. 26, 1996

(86) PCT No.: PCT/AU96/00535

§ 371 Date: Aug. 31, 1998

§ 102(e) Date: Aug. 31, 1998

(87) PCT Pub. No.: WO97/08297

PCT Pub. Date: Mar. 6, 1997

(30) Foreign Application Priority Data

Aug. 25, 1995 (AU) ........................................... PN 5034

(51) Int. Cl.[7] ........................... A01N 63/00; C12N 7/01; C12N 15/86

(52) U.S. Cl. .................... 424/93.2; 435/69.1; 435/235.1; 435/320.1

(58) Field of Search ............................. 435/320.1, 252.3, 435/69.1, 235.1; 424/93.2; 536/23.72

(56) References Cited

FOREIGN PATENT DOCUMENTS

| | | |
|---|---|---|
| 385394 | 9/1990 | (EP) . |
| 2218421 | 11/1989 | (GB) . |
| 93/03144 | 2/1993 | (WO) . |
| 93/25666 | 12/1993 | (WO) . |

OTHER PUBLICATIONS

Sun et al, Virologica Sinica 9(4):p309–318 (abstract only), 1994.*

Proceedings Series; Management of insect pests: Nuclear and related molecular and genetic techniques, pp. 125–132. International Atomic Energy Agency (IAEA), Vienna, Austria (title only), 1992.*

Somasekar S et al, Phytoparasitica 21(4):p333–337 (abstract only), 1993.*

Chuikova, VOPR Virusol 35(6). 497–500 (abstract only), 1990.*

JiN et al., Acta Entomol Sin 30(4). 377–386(abstract only), 1987.*

Ke et al., Virol Sin 2(1), 57–64 (Abstract only), 1987.*

Kislev, Intervirology 24(1), 50–57 (Abstract only), 1985.*

Williams et al, Ann Appl Biol 104(3). 405–412 (Abstract only), 1984.*

McCarthy et al, Virology 90(2). 374–378 (Abstract only), 1978.*

Boswell et al, In: Computational Molecular Biology, ed. A. M. Lesk, Oxford University Press, p. 161–178, 1988.*

Cowan et al, Journal of General Virology 75:3211–3218, Nov. 1994.*

Cowan et al.: "Nuclotide sequence of the polyhedrin gene region of *Helicoverpa zea* single nucleocapsid nuclear polyhedrosis virus: placement of the virs in lepidopeteran nuclear polyhedrosis virus group II." Journal of General Virology, 75(11), pp. 3211–3218, 1994.

* cited by examiner

*Primary Examiner*—Mary E. Mosher
(74) *Attorney, Agent, or Firm*—McDermott, Will & Emery

(57) ABSTRACT

Recombinant *Helicoverpa armigera* nuclear polyhedrosis viruses (HaSNPV) capable of expressing heterologous DNA sequences are described. Also described are pre-occluded baculoviruses which lack a functional polyhedrin gene and exhibit greater pathogenicity over wild-type viruses.

12 Claims, 21 Drawing Sheets

Figure 2A A44EB1 polyhedrin gene sequence.

```
              -150            -130            -110             -90
No.:5)  ATCTTTTGCAAGAATATGAAGATTTCTGTCGTCGTGTTGAAAATTTGTAATAAAACTAAATAAACCTTTAATATAAAT

-70             -50             -30             -10
        ATTAAACATACACTTTTATTCTAAAATAAGTATTTTTTTTCCTATTGTTCAAGATTGTGAAAAATCAAATATCCCATA 0               10              30              50              70
        ATGTATACTCGTTACAGTTACAGCCCTACTTTGGGCAAAACCTATGTGTACGACAACAAATACTTTAAGAATTAGGT
No.:6)   M  Y  T  R  Y  S  Y  S  P  T  L  G  K  T  Y  V  Y  D  N  K  Y  F  K  N  L  G 90              110             130             150
        GCTGTTATTAAAAATGCCAAACGCAAGAAGCATTTAGAGGAGCACGAAGAACGCAACTTAGATTCGCTCGAC
         A  V  I  K  N  A  K  R  K  K  H  L  E  E  H  E  E  R  N  L  D  S  L  D 170              190             210             230
        AAATACTTGGTGGCGGAAGATCCTTTTTTGGGACCTGGCAAAAATCAAAAACTAACTTTGTTTAAAGAGATTCGCAGC
         K  Y  L  V  A  E  D  P  F  L  G  P  G  K  N  Q  K  L  T  L  F  K  E  I  R  S 250              270             290             310
        GTTAAGCCCGACACAATGAAGCTTGTAGTTAACTGAGTTGTAGTGGAGCGGTCGCGAATTCTTCGCGAAACTTGGACTCGTTTCATG
         K  P  D  T  M  K  L  V  V  V  N  W  S  G  R  E  F  L  R  E  T  W  T  R  F  M 330              350             370              390
        GAAGACAGTTTTCCCATTGTAAACGACCAAGAAATTATGGACGTGTTTCTGTCTGTTAATATGCGACCAACAAACCG     4
         E  D  S  F  P  I  V  N  D  Q  E  I  M  D  V  F  L  S  V  N  M  R  P  T  K  P 410              430             450
        AACCGTGTTACCGATTCTTAGGCCAACACGCTCTGCGTTGTGATCCCGACTATATTCCTCACGAAGTCATTCGTATT
         N  R  C  Y  R  F  L  A  Q  H  A  L  R  C  D  P  D  Y  I  P  H  E  V  I  R  I 490              510             530
        GTAGAACCTTCCTATGTAGTAGGCAGTAACAACGAGTACAGAATTAGTTTAGCCAAAAAATACGGCGGTTGCCCCGTTATG
         V  E  P  S  Y  V  V  G  S  N  N  E  Y  R  R  I  S  L  A  K  K  Y  G  G  C  P  V  M
```

Figure 2B

```
550              570                590                610
AATTTGCACGCTGAATACACACTAATTCCTTTGAAGATTCATTACCAACGTAATTTGGGAGAACTTCTACAAACCAATT
 N  L  H  A  E  Y  T  N  S  F  E  D  F  I  T  N  V  I  W  E  N  F  Y  K  P  I 630              650                670                690
GTTTACGTAGGCACTGATTCTGCCGAAGAAGAGGAAATACTCCTAGAGGTTTCTTTGATATTTAAGATCAAAGAATTT
 V  Y  V  G  T  D  S  A  E  E  E  E  I  L  L  E  V  S  L  I  F  K  I  K  E  F 710              730                750                770
GCACCTGACGCTCCGCTATACACTGGTCCTGCATATTAAACTGCGATTCAGTTGACATCGTCAATTGTAACTCATA
 A  P  D  A  P  L  Y  T  G  P  A  Y 790              810                830                850
ATTTTATCTAAATTCGATCGCAATTCTTGTAATTTTTGATTGGTTCCTAATGCCGACACCACATTAGCT 870              890                910                930
AACGCTTTATCGTACTGTTTTTGAATGTCAAATCTTCCACCGCCATAATGAATTGTTGTAAATTTCTATCGGACAAT 950              970                990                1010
TGAAGTTCGACATCATCGGATTGTCCAAAGGATTATCATACGTTTCTTGTATCAAGTTATCTTCAATAAATATTT
```

Figure 3A (SEQ ID NO. :7)
```
     1 CTCGAGAATGTTGGTTTATCTGTGACTAAAGGTACGGGCCATTTTCGGTTAGCATCGATT
       ----------+----------+----------+----------+----------+----------+ 60
       GAGCTCTTACAACCAAATAGACACTGATTTCCATGCCCGGTAAAAGCCAATCGTAGCTAA
           S  F  T  P  K  D  T  V  L  P  V  P  W  K  R  N  A  D  I  -
                                                              ←

61 TGTACTAAGTCGGGATTCATTGCAACCGCACTGTGATCAATGGCGTTATTTTTTTCAATC
       ----------+----------+----------+----------+----------+----------+ 120
       ACATGATTCAGCCCTAAGTAACGTTGGCGTGACACTAGTTACCGCAATAAAAAAAGTTAG
         Q  V  L  D  P  N  M  A  V  A  S  H  D  I  A  N  N  K  E  I  -
                                          ←

121 AATTCAATAATTTGTCTGTATATGTATGTTTGCAAATCGTGAAATATAGTTTCGCTGTTC
       ----------+----------+----------+----------+----------+----------+ 180
       TTAAGTTATTAAACAGACATATACATACAAACGTTTAGCACTTTATATCAAAGCGACAAG
         L  E  I  I  Q  R  Y  I  Y  T  Q  L  D  H  F  I  T  E  S  N  -
                                          ←

181 TCGCAACGGGTTAAATTTTTATTCTTGATCCATTCAACTAGATTATTGTACGAATTGTGC
       ----------+----------+----------+----------+----------+----------+ 240
       AGCGTTGCCCAATTTAAAAATAAGAACTAGGTAAGTTGATCTAATAACATGCTTAACACG
         E  C  R  T  L  N  K  N  K  I  W  E  V  L  N  N  Y  S  N  H  -
                                          ←

241 AATTGTACCAGTTCTTCAAATATAATATTGTGATCGACTTCGATGACAAAATGCCAAACG
       ----------+----------+----------+----------+----------+----------+ 300
       TTAACATGGTCAAGAAGTTTATATTATAACACTAGCTGAAGCTACTGTTTTACGGTTTGC
         L  Q  V  L  E  E  F  I  I  N  H  D  V  E  I  V  F  H  W  V  -
                                          ←

301 TCTTCAACGAATCTCATTTGATAGATTTTGTCAAAGTACAAACCAATAGTGCGCGGCAAA
       ----------+----------+----------+----------+----------+----------+ 360
       AGAAGTTGCTTAGAGTAAACTATCTAAAACAGTTTCATGTTTGGTTATCACGCGCCGTTT
           D  E  V  F  R  M
                                          ←

361 GAGATAATTTTTAGCAAATTTGTAGGATCGATGGCAAAAGACTCTGTCGTTTCGCGACTC
       ----------+----------+----------+----------+----------+----------+ 420
       CTCTATTAAAAATCGTTTAAACATCCTAGCTACCGTTTTCTGAGACAGCAAAGCGCTGAG

421 GCGTCAACGACATAGAAATAGATATAGTACACAATAAAATTTTAGTCAGCTTAGAGCTGG
       ----------+----------+----------+----------+----------+----------+ 480
       CGCAGTTGCTGTATCTTTATCTATATCATGTGTTATTTTAAAATCAGTCGAATCTCGACC

481 ACAGACTACTYTTTATCGCAACCANTGTTACAAAACTGACGTTGAACACTTTGAACGGTC
       ----------+----------+----------+----------+----------+----------+ 540
       TGTCTGATGARAAATAGCGTTGGTNACAATGTTTTGACTGCAACTTGTGAAACTTGCCAG

541 TACTTTATATATTTTCGTAACCTTATAACTATTACGGAACGGGTTAATATAAAAATAACT
       ----------+----------+----------+----------+----------+----------+ 600
       ATGAAATATATAAAGCATTGGAATATTGATAATGCCTTGCCCAATTATATTTTTATTGA

601 AGATTAATAAATGTATGTTTTTATTGTATAAAGATAACAAATACACATTTATATTATAAA
       ----------+----------+----------+----------+----------+----------+ 660
       TCTAATTATTTACATACAAAAATAACATATTTCTATTGTTTATGTGTAAATATAATATTT
                                                              *  I  I  F
                                                              ←

661 TCCATAAGGATTACACATTTTAGAAGTTATTAATTCGTTAAAAGTAATATAATTTCTATA
       ----------+----------+----------+----------+----------+----------+ 720
       AGGTATTCCTAATGTGTAAAATCTTCAATAATTAAGCAATTTTCATTATATTAAAGATAT
         G  Y  P  N  C  M  K  S  T  I  L  E  N  F  T  I  Y  N  R  Y
                                          ←
```

Figure 3B

```
     AGTATTTACGTCTGTTACACAGTAATCGGAGTTATTTGTAGTATTCATATCTGTGTAAAT
721  ------------+----------+----------+----------+----------+----------+  780
     TCATAAATGCAGACAATGTGTCATTAGCCTCAATAAACATCATAAGTATAGACACATTTA
      T  N  V  D  T  V  C  Y  D  S  N  N  T  T  N  M  D  T  Y  I  -
                                        ←

GTCACAATACCAAGGTTTTCTAAAAAGTTTGTTTTCGTCGTGACATTTAAATATATCGGA
781  ------------+----------+----------+----------+----------+----------+  840
     CAGTGTTATGGTTCCAAAAGATTTTTCAAACAAAAGCAGCACTGTAAATTTATATAGCCT
        D  C  Y  W  P  K  R  F  L  K  N  E  D  H  C  K  F  I  D  S  -
                                        ←

AAAGCAAAACCACAAAAAATCTTTGTTCAAAGCCAAACTAATATCAGTAACTAGATTCAA
841  ------------+----------+----------+----------+----------+----------+  900
     TTTCGTTTTGGTGTTTTTTAGAAACAAGTTTCGGTTTGATTATAGTCATTGATCTAAGTT
        F  C  F  W  L  F  D  K  N  L  A  L  S  I  D  T  V  L  N  L  -
                                        ←

TTTTCTTCGTCAATATTTTCAAAATTATAAAATACGGTATAGGCAATACCATAATTGAA
901  ------------+----------+----------+----------+----------+----------+  960
     AAAAAGAAGCAGTTATAAAAGTTTTAATATTTTATGCCATATCCGTTATGGTATTAACTT
        K  E  E  D  I  N  E  F  N  Y  F  V  T  Y  A  I  G  Y  N  F  -
                                        ←

CCATTTGTCGTTACGGCACCATTTTTTCCATCWTTTTATATATTGTAGCATCTGGTTCCA
961  ------------+----------+----------+----------+----------+----------+  1020
     GGTAAACAGCAATGCCGTGGTAAAAAAGGTAGWAAAATATATAACATCGTAGACCAAGGT
        W  K  D  N  R  C  W  K  K  W  ?  K  I  Y  Q  L  M  Q  N  W  -
                                        ←

ATTGATTTCGTCGTTTTTAACCGCAATTTCGCTTTCGACAGACGAATAATACCATCCAGA
1021 ------------+----------+----------+----------+----------+----------+  1080
     TAACTAAAGCAGCAAAAATTGGCGTTAAAGCGAAAGCTGTCTGCTTATTATGGTAGGTCT
        N  I  E  D  N  K  V  A  I  E  S  E  V  S  S  Y  Y  W  G  S  -
                                        ←

CGGTAGAGCAATACGAATATGTTCAAATATAGCCATATATTCTTTTTCGATACGAACATT
1081 ------------+----------+----------+----------+----------+----------+  1140
     GCCATCTCGTTATGCTTATACAAGTTTATATCGGTATATAAGAAAAAGCTATGCTTGTAA
        P  L  A  I  R  I  H  E  F  I  A  M  Y  E  K  E  I  R  V  N  -
                                        ←

GTGATACACAACTTGTAATAGACTCAATGTCAGCAGACTCGATGGTGTACACATTTTGTT
1141 ------------+----------+----------+----------+----------+----------+  1200
     CACTATGTTGAACATTATCTGAGTTACAGTCGTCTGAGCTACCACATGTGTAAAACAA
        H  Y  V  V  Q  L  L  S  L  T  L  L  S  S  P  T  C  M  -
                                        ←

AGATTCCTAACGATGCGAATGGTGAATAGCATTATTGTTTAAACGGTTATATAGTAATTA
1201 ------------+----------+----------+----------+----------+----------+  1260
     TCTAAGGATTGCTACGCTTACCACTTATCGTAATAACAAATTTGCCAATATATCATTAAT

TTAATCTAATCTTGACATTATCATTTTATTGATAACAATAGATATGATAAAATTATACTA
1261 ------------+----------+----------+----------+----------+----------+  1320
     AATTAGATTAGAACTGTAATAGTAAAATAACTATTGTTATCTATACTATTTTAATATGAT

TATAAATCAAAACAGAATTCATTTTAATTACAGTTTATACAATTGTACAAACAGTTTATA
1321 ------------+----------+----------+----------+----------+----------+  1380
     ATATTTAGTTTTGTCTTAAGTAAAATTAATGTCAAATATGTTAACATGTTTGTCAAATAT

ACCAACCATGTGTAACGTGTGGCCAGTGGTTAACCGTGTGCTTTGCAAACTAGTCATGCA
1381 ------------+----------+----------+----------+----------+----------+  1440
     TGGTTGGTACACATTGCACACCGGTCACCAATTGGCACACGAAACGTTTGATCAGTACGT
                M  C  N  V  W  P  V  V  N  R  V  L  C  K  L  V  M  Q  -
                →
```

Figure 3C

```
     AAATTTGTCCAAAATATATGGCAATATACAATTTTTATATCTGATGGGCAACAAGCCAAA
1441 ------------+---------+---------+---------+---------+---------+ 1500
     TTTAAACAGGTTTTATATACCGTTATATGTTAAAAATATAGACTACCCGTTGTTCGGTTT
      N  L  S  K  I  Y  G  N  I  Q  F  L  Y  L  M  G  N  K  P  K  -
                                   →

GGAAATTCAAGAGGAACAAGCCAATTTCAACGAACTATATTACAAGTTCAAAGTGTTTAG
1501 ------------+---------+---------+---------+---------+---------+ 1560
     CCTTTAAGTTCTCCTTGTTCGGTTAAAGTTGCTTGATATAATGTTCAAGTTTCACAAATC
      E  I  Q  E  E  Q  A  N  F  N  E  L  Y  Y  K  F  K  V  F  R  -
                                   →

ATCACAATTGCCCGACATGAATTGTGAAACTTTTGCTCATAAAATTGATTGACCAGAAAAT
1561 ------------+---------+---------+---------+---------+---------+ 1620
     TAGTGTTAACGGGCTGTACTTAACACTTTGAAAACGAGTATTTAACTAACTGGTCTTTTA
      S  Q  L  P  D  M  N  C  E  T  F  A  H  K  L  I  D  Q  K  I  -
                                   →

ATTGTATTGCAGAGAAATTCATAATTTGTATTTGAACTTTTTATATTGCTTCTACAAACA
1621 ------------+---------+---------+---------+---------+---------+ 1680
     TAACATAACGTCTCTTTAAGTATTAAACATAAACTTGAAAAATATAACGAAGATGTTTGT
      L  Y  C  R  E  I  H  N  L  Y  L  N  F  L  Y  C  F  Y  K  Q  -
                                   →

ATACTTTGACACGCTGAAGATTGACTGCCATATTTTTAAGGATTTGATAGATGACGATGT
1681 ------------+---------+---------+---------+---------+---------+ 1740
     TATGAAACTGTGCGACTTCTAACTGACGGTATAAAAATTCCTAAACTATCTACTGCTACA
      Y  F  D  T  L  K  I  D  C  H  I  F  K  D  L  I  D  D  D  V  -
                                   →

ACCATTGCAAGATTTTGAAGAGTTAAATGTTGTTCTACTCGACAATAACATACCAATGTA
1741 ------------+---------+---------+---------+---------+---------+ 1800
     TGGTAACGTTCTAAAACTTCTCAATTTACAACAAGATGAGCTGTTATTGTATGGTTACAT
      P  L  Q  D  F  E  E  L  N  V  V  L  L  D  N  N  I  P  M  Y  -
                                   →

TACGGCTTTGTGTGATGATGTGTTTGAAAAGAAAACCATTATACAAGATATAGAATATGT
1801 ------------+---------+---------+---------+---------+---------+ 1860
     ATGCCGAAACACACTACTACACAAACTTTTCTTTTGGTAATATGTTCTATATCTTATACA
      T  A  L  C  D  D  V  F  E  K  K  T  I  I  Q  D  I  E  Y  V  -
                                   →

AATGAACAAAATATGCGTTGAAGGAGCGTACGTGCCATTTCAAGAAGAANTTTTGCAATA
1861 ------------+---------+---------+---------+---------+---------+ 1920
     TTACTTGTTTTATACGCAACTTCCTCGCATGCACGGTAAAGTTCTTCTTNAAAACGTTAT
      M  N  K  I  C  V  E  G  A  Y  V  P  F  Q  E  E  ?  L  Q  Y  -
                                   →

TCAAATCTTTTTGCAAGAATATGAAGATTTCTGTCGTCGTGTTGAAAATTTGTAATAAAA
1921 ------------+---------+---------+---------+---------+---------+ 1980
     AGTTTAGAAAAACGTTCTTATACTTCTAAAGACAGCAGCACAACTTTTAAACATTATTTT
      Q  I  F  L  Q  E  Y  E  D  F  C  R  R  V  E  N  L  *        -

CGAAATAAACCTTTAATATAAATATTAAACATACACTTTTATTTCTAAAATAAGTATTTT
1981 ------------+---------+---------+---------+---------+---------+ 2040
     GCTTTATTTGGAAATTATATTTATAATTTGTATGTGAAAATAAAGATTTATTCATAAAA

TTCCCTATTGTTCAAGATTGTGAAAAATCAAATATCCCATAATGTATACTCGTTACAGTT
2041 ------------+---------+---------+---------+---------+---------+ 2100
     AAGGGATAACAAGTTCTAACACTTTTTAGTTTATAGGGTATTACATATGAGCAATGTCAA
                                                 M  Y  T  R  Y  S  Y -
                                                 → POLYHEDRIN

ACAGCCCTACTTTGGGCAAAACCTATGTGTACGACAACAAATACTTTAAGAATTTAGGTG
2101 ------------+---------+---------+---------+---------+---------+ 2160
     TGTCGGGATGAAACCCGTTTTGGATACACATGCTGTTGTTTATGAAATTCTTAAATCCAC
      S  P  T  L  G  K  T  Y  V  V  Y  D  N  K  Y  F  K  N  L  G  A -
                                   →
```

Figure 3D

```
      CTGTTATTAAAAATGCCAAACGCAAGAAGCATTTAGAGGAGCACGAACATGAAGAACGCA
2161  ----------+---------+----------+---------+---------+---------+  2220
      GACAATAATTTTTACGGTTTGCGTTCTTCGTAAATCTCCTCGTGCTTGTACTTCTTGCGT
       V  I  K  N  A  K  R  K  K  H  L  E  E  H  E  H  E  E  R  N  -
                                       →

ACTTAGATTCGCTCGACAAATACTTGGTGGCGGAAGATCCTTTTTTGGGACCTGGCAAAA
2221  ----------+---------+----------+---------+---------+---------+  2280
      TGAATCTAAGCGAGCTGTTTATGAACCACCGCCTTCTAGGAAAAAACCCTGGACCGTTTT
       L  D  S  L  D  K  Y  L  V  A  E  D  P  F  L  G  P  G  K  N  -
                                       →

ATCAAAAACTAACTTTGTTTAAAGAGATTCGCAGCGTTAAGCCCGACACAATGAAGCTTG
2281  ----------+---------+----------+---------+---------+---------+  2340
      TAGTTTTTGATTGAAACAAATTTCTCTAAGCGTCGCAATTCGGGCTGTGTTACTTCGAAC
        Q  K  L  T  L  F  K  E  I  R  S  V  K  P  D  T  M  K  L  V -
                                       →

TAGTTAACTGGAGCGGTCGCGAATTTCTTCGCGAAACTTGGACTCGTTTCATGGAAGACA
2341  ----------+---------+----------+---------+---------+---------+  2400
      ATCAATTGACCTCGCCAGCGCTTAAAGAAGCGCTTTGAACCTGAGCAAAGTACCTTCTGT
          V  N  W  S  G  R  E  F  L  R  E  T  W  T  R  F  M  E  D  S -
                                       →

GTTTTCCCATTGTAAACGACCAAGAAATTATGGACGTGTTTCTGTCTGTTAATATGCGAC
2401  ----------+---------+----------+---------+---------+---------+  2460
       CAAAAGGGTAACATTTGCTGGTTCTTTAATACCTGCACAAAGACAGACAATTATACGCTG
         F  P  I  V  N  D  Q  E  I  M  D  V  F  L  S  V  N  M  R  P -
                                       →

CAACCAAACCGAACCGTTGTTACCGATTCTTAGCGCAACACGCTCTGCGTTGTGATCCCG
2461  ----------+---------+----------+---------+---------+---------+  2520
      GTTGGTTTGGCTTGGCAACAATGGCTAAGAATCGCGTTGTGCGAGACGCAACACTAGGGC
        T  K  P  N  R  C  Y  R  F  L  A  Q  H  A  L  R  C  D  P  D -
                                       →

ACTATATTCCTCACGAAGTCATTCGTATTGTAGAACCTTCCTATGTAGGCAGTAACAACG
2521  ----------+---------+----------+---------+---------+---------+  2580
      TGATATAAGGAGTGCTTCAGTAAGCATAACATCTTGGAAGGATACATCCGTCATTGTTGC
         Y  I  P  H  E  V  I  R  I  V  E  P  S  Y  V  G  S  N  N  E -
                                       →

AGTACAGAATTAGTTTAGCCAAAAAATACGGCGGTTGCCCCGTTATGAATTTGCACGCTG
2581  ----------+---------+----------+---------+---------+---------+  2640
      TCATGTCTTAATCAAATCGGTTTTTATGCCGCCAACGGGGCAATACTTAAACGTGCGAC
         Y  R  I  S  L  A  K  K  Y  G  G  C  P  V  M  N  L  H  A  E -
                                       →

AATACACTAATTCCTTTGAAGATTTCATTACCAACGTAATTTGGGAGAACTTCTACAAAC
2641  ----------+---------+----------+---------+---------+---------+  2700
      TTATGTGATTAAGGAAACTTCTAAAGTAATGGTTGCATTAAACCCTCTTGAAGATGTTTG
         Y  T  N  S  F  E  D  F  I  T  N  V  I  W  E  N  F  Y  K  P -
                                       →

CAATTGTTTACGTAGGGACTGATTCTGCCGAAGAAGAGGAAATACTCCTAGAGGTTTCTT
2701  ----------+---------+----------+---------+---------+---------+  2760
      GTTAACAAATGCATCCCTGACTAAGACGGCTTCTTCTCCTTTATGAGGATCTCCAAAGAA
         I  V  Y  V  G  T  D  S  A  E  E  E  E  I  L  L  E  V  S  L  -
                                       →

TGATATTTAAGATCAAAGAATTTGCACCTGACGCTCCGCTATACACTGGTCCTGCATATT
2761  ----------+---------+----------+---------+---------+---------+  2820
      ACTATAAATTCTAGTTTCTTAAACGTGGACTGCGAGGCGATATGTGACCAGGACGTATAA
          I  F  K  I  K  E  F  A  P  D  A  P  L  Y  T  G  P  A  Y  * -
                                                                    →
```

Figure 3E

```
       AAACTTGCGATTCAGTTGACATCGTCAATTTGTAACTCATAATTTTATCTAAATTCGATC
2821   ------------+----------+----------+----------+----------+----------+   2880
       TTTGAACGCTAAGTCAACTGTAGCAGTTAAACATTGAGTATTAAAATAGATTTAAGCTAG
     *  V  Q  S  E  T  S  M  T  L  K  Y  S  M  I  K  D  L  N  S  -
       ←

GCAATTCTTGTAATTTTTGATTGGTCGGTTTGGTTCCTAATGCCGACACCACATTAGCTA
2881   ------------+----------+----------+----------+----------+----------+   2940
       CGTTAAGAACATTAAAAACTAACCAGCCAAACCAAGGATTACGGCTGTGGTGTAATCGAT
        R  L  E  Q  L  K  Q  N  T  P  K  T  G  L  A  S  V  V  N  A  -
                                              ←

ACGCTTTATCGTACTGTTTTTTGAATGTCAAATCTTCCACCGCCATAATGAATTGTTGTA
2941   ------------+----------+----------+----------+----------+----------+   3000
       TGCGAAATAGCATGACAAAAAACTTACAGTTTAGAAGGTGGCGGTATTACTTAACAACAT
        L  A  K  D  Y  Q  K  K  F  T  L  D  E  V  A  M  I  F  Q  Q  -
                                  ←

AATTTCTATCGGACAATTGAAGTTCGACATCATCGGATTTGTCCAAAGGATTATCATACG
3001   ------------+----------+----------+----------+----------+----------+   3060
       TTAAAGATAGCCTGTTAACTTCAAGCTGTAGTAGCCTAAACAGGTTTCCTAATAGTATGC
        L  N  R  D  S  L  Q  L  E  V  D  D  S  K  D  L  P  N  D  Y  -
                                        ←

TTTCTTGTATCAAGTTATCTTCAATAAATATTTGTAGTTTAGCAGAAACCTGTTGTGTTT
3061   ------------+----------+----------+----------+----------+----------+   3120
       AAAGAACATAGTTCAATAGAAGTTATTTATAAACATCAAATCGTCTTTGGACAACACAAA
        T  E  Q  I  L  N  D  E  I  F  I  Q  L  K  A  S  V  Q  Q  T  -
                                                    ←

GTGCATTCGAAAGCCGTTGATTTAATTGATTTTTTATTGATATTAATGTGTCTTGTGCTT
3121   ------------+----------+----------+----------+----------+----------+   3180
       CACGTAAGCTTTCGGCAACTAAATTAACTAAAAAATAACTATAATTACACAGAACACGAA
        Q  A  N  S  L  R  Q  N  L  Q  N  K  I  S  I  L  T  D  Q  A  -
                              ←

CAGTAGACAAAGGATAATTTTTTATCCATGAACTGTCCAATGTTATATTGTACAAAGAAC
3181   ------------+----------+----------+----------+----------+----------+   3240
       GTCATCTGTTTCCTATTAAAAAATAGGTACTTGACAGGTTACAATATAACATGTTTCTTG
        E  T  S  L  P  Y  N  K  I  W  S  S  D  L  T  I  N  Y  L  S  -
                                              ←

GTACATATTGTTTTAATTCGCTGCTGGCTCGCTGCTGTTGTTCGTCGTCGGTCCACCCGT
3241   ------------+----------+----------+----------+----------+----------+   3300
       CATGTATAACAAAATTAAGCGACGACCGAGCGACGACAACAAGCAGCAGCCAGGTGGGCA
        R  V  Y  Q  K  L  E  S  S  A  R  Q  Q  Q  E  D  D  T  W  G  -
                                              ←

TTTCCGATTCTGACGAAACTACAGGACTCGGTTGAACGGCTATGCGTCGTTGTAAAACCT
3301   ------------+----------+----------+----------+----------+----------+   3360
       AAAGGCTAAGACTGCTTTGATGTCCTGAGCCAACTTGCCGATACGCAGCAACATTTGGA
    ←      N  E  S  E  S  S  V  V  P  S  P  Q  V  A  I  R  R  Q  L  V  -

TTGCAGTAGGACTGGCGGCGGCGGTAACGGTATTTACTATCGAGCCATTGGCGGGTTTTA
3361   ------------+----------+----------+----------+----------+----------+   3420
       AACGTCATCCTGACCGCCGCCGCCATTGCCATAAATGATAGCTCGGTAACCGCCCAAAAT
        K  A  T  P  S  A  A  A  T  V  T  N  V  I  S  G  N  A  P  K  -
                                              ←

ATACTTTTTTTAATTTAATTCCTTTCTGTATTTGTTCCATCAATTCGGTACGTGGATCTT
3421   ------------+----------+----------+----------+----------+----------+   3480
       TATGAAAAAAATTAAATTAAGGAAAGACATAAACAAGGTAGTTAAGCCATGCACCTAGAA
        L  V  K  K  L  K  I  G  K  Q  I  Q  E  M  L  E  T  R  P  D  -
                                              ←
```

Figure 3F

```
      TTAAAACTTGCCGAGTCGACGTTGTATAATCGCGATCTTTACTGGATGGTATTACTATAT
3481  ------------+----------+----------+----------+----------+----------+  3540
      AATTTTGAACGGCTCAGCTGCAACATATTAGCGCTAGAAATGACCTACCATAATGATATA
       K  L  V  Q  R  T  S  T  T  Y  D  R  D  K  S  S  P  I  V  I  -
                                           ←

CTTCTATTAATGGTAATGACGGTGGCGGAGGAGGCGGCGGCAAAGGAGGTATCGTCGAAG
3541  ------------+----------+----------+----------+----------+----------+  3600
      GAAGATAATTACCATTACTGCCACCGCCTCCTCCGCCGCCGTTTCCTCCATAGCAGCTTC
       D  E  I  L  P  L  S  P  P  P  P  P  P  P  L  P  P  I  T  S  -
                                           ←

ATAAGTTTGTTTGAGGCGGCGGCGGTGGCGGCGGTATTGGTGGTGGTATTGGTGGCGGCA
3601  ------------+----------+----------+----------+----------+----------+  3660
      TATTCAAACAAACTCCGCCGCCGCCACCGCCGCCATAACCACCACCATAACCACCGCCGT
       S  L  N  T  Q  P  P  P  P  P  P  P  I  P  P  P  I  P  P  P  -
                                           ←

TATGTGTTTGCGGCGAGGAAGATTCAGAATCGATAATTATTGTTGGCGAAATTGTTTTTT
3661  ------------+----------+----------+----------+----------+----------+  3720
      ATACACAAACGCCGCTCCTTCTAAGTCTTAGCTATTAATAACAACCGCTTTAACAAAAAA
       M  H  T  Q  P  S  S  S  E  S  D  I  I  I  T  P  S  I  T  K  -
                                           ←

GCATTATATCCGATGTCGACACAGTTGTCGGTTTAGGTATTGTTGTTTTAGGGACTGTTG
3721  ------------+----------+----------+----------+----------+----------+  3780
      CGTAATATAGGCTACAGCTGTGTCAACAGCCAAATCCATAACAACAAAATCCCTGACAAC
       Q  M  I  D  S  T  S  V  T  T  P  K  P  I  T  T  K  P  V  T  -
                                           ←

GTACTGACATTGTCTGTGACAATGTTGGTATAATAATTTGATCTATCACCAATGTCTATT
3781  ------------+----------+----------+----------+----------+----------+  3840
      CATGACTGTAACAGACACTGTTACAACCATATTATTAAACTAGATAGTGGTTACAGATAA
       P  V  S  M                                                    -
                  ←

AGTACGTCGTTGTTGTATATTCTTGGGCCAATTTCAATAACTGAATACAATCGTACACG
3841  ------------+----------+----------+----------+----------+----------+  3900
      TCATGCAGCAACAACATATAAAGAACCCGGTTAAAGTTATTGACTTATGTTAGCATGTGC

TTTAATTGTATCCGATCAGAATTGGACTGAGCGACAGCGCTGACCGTACGTTTCAAACCT
3901  ------------+----------+----------+----------+----------+----------+  3960
      AAATTAACATAGGCTAGTCTTAACCTGACTCGCTGTCGCGACTGGCATGCAAAGTTTGGA

GTGCGGCGCCGAGTTCATGCGCAGTAGAAAGTCGACATTATTGATGTTTGTGTAGTTTTT
3961  ------------+----------+----------+----------+----------+----------+  4020
      CACGCCGCGGCTCAAGTACGCGTCATCTTTCAGCTGTAATAACTACAAACACATCAAAAA

TTCAGCCAAATATTGTTGAACACTTTGCAGTTGAACCATTATCGCGAATCGCAATGGACG
4021  ------------+----------+----------+----------+----------+----------+  4080
      AAGTCGGTTTATAACAACTTGTGAAACGTCAACTTGGTAATAGCGCTTAGCGTTACCTGC
                                                               M  D  D  -
                                                                →

ACCGTTTCGTTAAGGAAATAAACCAATTTTTCGCCGAAATAAAAATACAAAACAATGTGC
4081  ------------+----------+----------+----------+----------+----------+  4140
      TGGCAAAGCAATTCCTTTATTTGGTTAAAAAGCGGCTTTATTTTTATGTTTTGTTACACG
       R  F  V  K  E  I  N  Q  F  F  A  E  I  K  I  Q  N  N  V  R  -
                                           →

GTTTGGTCGACGGCAAGTTTGGCAAAATGTGTGTTATCAAACACGAGCCCACGGGCAAAC
4141  ------------+----------+----------+----------+----------+----------+  4200
      CAAACCAGCTGCCGTTCAAACCGTTTTACACACAATAGTTTGTGCTCGGGTGCCCGTTTG
       L  V  D  G  K  F  G  K  M  C  V  I  K  H  E  P  T  G  K  L  -
                                           →
```

Figure 3G

```
     TGTTCGTAAAAAAGAGTGTCGCAATTAAATATGTGACCGAGATCGAACCTATGGTGCATC
4201 ------------+---------+---------+---------+---------+---------+ 4260
     ACAAGCATTTTTTCTCACAGCGTTAATTTATACACTGGCTCTAGCTTGGATACCACGTAG
      F  V  K  K  S  V  A  I  K  Y  V  T  E  I  E  P  M  V  H  Q  -
                                     →

AACTAATGAAGGACAACCGATATTTCATCAAATTATATTACTCGTTGACAACGTTAAAAT
4261 ------------+---------+---------+---------+---------+---------+ 4320
     TTGATTACTTCCTGTTGGCTATAAAGTAGTTTAATATAATGAGCAACTGTTGCAATTTTA
      L  M  K  D  N  R  Y  F  I  K  L  Y  Y  S  L  T  T  L  K  S  -
                                     →

CTCAAATACTAATATTAGATTACGTTGCTGGAGGCGATTTGTTTGATTTTTAAAAAAAC
4321 ------------+---------+---------+---------+---------+---------+ 4380
     GAGTTTATGATTATAATCTAATGCAACGACCTCCGCTAAACAAACTAAAAAATTTTTTG
      Q  I  L  I  L  D  Y  V  A  G  G  D  L  F  D  F  L  K  K  H  -
                                     →

ACAAAAAAGTATCTGAAGCGGAAACACGTTCAATAGTGGGTCAATTAACCGAAGCACNSA
4381 ------------+---------+---------+---------+---------+---------+ 4440
     TGTTTTTTCATAGACTTCGCCTTTGTGCAAGTTATCACCCAGTTAATTGGCTTCGTGNST
      K  K  V  S  E  A  E  T  R  S  I  V  G  Q  L  T  E  A  ?  N  -
                                     →

ACGCGCTTCACGCTTACAAATTABAACATAACGATCTCAAACTCGAAAACGTCCTATACG
4441 ------------+---------+---------+---------+---------+---------+ 4500
     TGCGCGAAGTGCGAATGTTTAATVTTGTATTGCTAGAGTTTGAGCTTTTGCAGGATATGC
      A  L  H  A  Y  K  L  ?  H  N  D  L  K  L  E  N  V  L  Y  V  -
                                     →

TACGTCATAAACAAATTTATTTGTGTGATTATGGACTGTGTAAAATTGTCAACACGACTT
4501 ------------+---------+---------+---------+---------+---------+ 4560
     ATGCAGTATTTGTTTAAATAAACACACTAATACCTGACACATTTTAACAGTTGTGCTCAA
      R  H  K  Q  I  Y  L  C  D  Y  G  L  C  K  I  V  N  T  S  S  -
                                     →

CGTGTCGAGACGGCACAAAGGAGTACATGTCTCCGGAGAAGCTCAAACGACAAAATTACG
4561 ------------+---------+---------+---------+---------+---------+ 4620
     GCACAGCTCTGCCGTGTTTCCTCATGTACAGAGGCCTCTTCGAGTTTGCTGTTTTAATGC
      C  R  D  G  T  K  E  Y  M  S  P  E  K  L  K  R  Q  N  Y  D  -
                                     →

ATGTTCACGTCGATTGGTGGGCTTTGGGCATCTTGACGTATGAACTTTTAATTGGACATC
4621 ------------+---------+---------+---------+---------+---------+ 4680
     TACAAGTGCAGCTAACCACCCGAAACCCGTAGAACTGCATACTTGAAAATTAACCTGTAG
      V  H  V  D  W  W  A  L  G  I  L  T  Y  E  L  L  I  G  H  H  -
                                     →

ATCCCTACAAACATAGCAACGACAACGAAGAAGATTTCGATTTGGATGTACTACAACAGA
4681 ------------+---------+---------+---------+---------+---------+ 4740
     TAGGGATGTTTGTATCGTTGCTGTTGCTTCTTCTAAAGCTAAACCTACATGATGTTGTCT
      P  Y  K  H  S  N  D  N  E  E  D  F  D  L  D  V  L  Q  Q  R  -
                                     →

GACAACAAAAAAAACTTCACAAATACAATTTTCTAAGTAGTGACGCTCAAAAATTTTTGG
4741 ------------+---------+---------+---------+---------+---------+ 4800
     CTGTTGTTTTTTTTGAAGTGTTTATGTTAAAAGATTCATCACTGCGAGTTTTAAAAACC
      Q  Q  K  K  L  H  K  Y  N  F  L  S  S  D  A  Q  K  F  L  E  -
                                     →

AAGCAATGTTAATGTATAACNTTAATTACAGGTTGTGTACATACGAGACTGTAATAAAAC
4801 ------------+---------+---------+---------+---------+---------+ 4860
     TTCGTTACAATTACATATTGNAATTAATGTCCAACACATGTATGCTCTGACATTATTTTG
      A  M  L  M  Y  N  ?  N  Y  R  L  C  T  Y  E  T  V  I  K  H  -
                                     →
```

Figure 3H

```
       ACGGTTTTTTATCATAATATATATTTAATAAAAAAGAATAATGTTGTTTCTTTATTACCA
 4861  ------------+----------+----------+----------+----------+----------+ 4920
       TGCCAAAAAATAGTATTATATATAAATTATTTTTCTTATTACAACAAAGAAATAATGGT  -
          G  F  L  S  *
                   →

TTACAACTAANTTATAAAATATTACAAAANTTTATTTACAATCTATTAAAACNAAAATAT
 4921  ------------+----------+----------+----------+----------+----------+ 4980
       AATGTTGATTNAATATTTTATAATGTTTTNAAATAAATGTTAGATAATTTTGNTTTTATA

TATGATATTATAAAAGTTACATTAAATATTATCTGCTTTGCGAGCACGTGAAGTGCGTTG
 4981  ------------+----------+----------+----------+----------+----------+ 5040
       ATACTATAATATTTTCAATGTAATTTATAATAGACGAAACGCTCGTGCACTTCACGCAAC  -
                  *  I  N  D  A  K  R  A  R  S  T  R  Q
                                                     ←

ACGTTTAGCTGGTGGTTCTTCAGTACGAAGAACKGGTACTCTAACCATACGAAAAGTAGC
 5041  ------------+----------+----------+----------+----------+----------+ 5100
       TGCAAATCGACCACCAAGAAGTCATGCTTCTTGMCCATGAGATTGGTATGCTTTTCATCG
         R  K  A  P  P  E  E  T  R  L  V  P  V  R  V  M  R  F  T  A  -
                                                     ←

TATCTGAGGTTTCATGTTATCTGCCCATTGCACKATTTCAACCKCATCGTCACTATCGTC
 5101  ------------+----------+----------+----------+----------+----------+ 5160
       ATAGACTCCAAAGTACAATAGACGGGTAACGTGMTAAAGTTGGMGTAGCAGTGATAGCAG
          I  Q  P  K  M  N  D  A  W  Q  V  I  E  V  ?  D  D  S  D  D
                                                     ←

ATTGACGAACCTAGCAGGGCTTAAAGGTAAATTTAAACATTCAACATCAGACATATCGAC
 5161  ------------+----------+----------+----------+----------+----------+ 5220
       TAACTGCTTGGATCGTCCCGAATTTCCATTTAAATTTGTAAGTTGTAGTCTGTATAGCTG  -
          N  V  F  R  A  P  S  L  P  L  N  L  C  E  V  D  S  M  D  V
                                                     ←

AGGTTCTTGTTTGGGAACACATTCTTCATGATACTCATTAATATAATCAGGATTTTCACA
 5221  ------------+----------+----------+----------+----------+----------+ 5280
       TCCAAGAACAAACCCTTGTGTAAGAAGTACTATGAGTAATTATATTAGTCCTAAAAGTGT  -
          P  E  Q  K  P  V  C  E  E  H  Y  E  N  I  Y  D  P  N  E  C
                                                     ←

TTCAGTATTAAAATCATCCCCAAACAATTCTTTTTTTATGGCAATGTCAAATGGTGCAGC
 5281  ------------+----------+----------+----------+----------+----------+ 5340
       AAGTCATAATTTTAGTAGGGGTTTGTTAAGAAAAAAATACCGTTACAGTTTACCACGTCG
          E  T  N  F  D  D  G  F  L  E  K  K  I  A  I  D  F  P  A  A
                                                     ←

GTCATTATTATCATCAGTAGTGTTAGCATCCTTTGATGTTTTTCTGTTTTAACAGTGAT
 5341  ------------+----------+----------+----------+----------+----------+ 5400
       CAGTAATAATAGTAGTCATCACAATCGTAGGAAACTACAAAAAAGACAAAATTGTCACTA
          D  N  N  D  D  T  T  N  A  D  K  S  T  K  E  T  K  V  T  I  -
                                                     ←

ATGCTCGAAATATTTGCCATTTTTGTCTACATTGGTACTTTTAGCTAATTCTTTATCGAT
 5401  ------------+----------+----------+----------+----------+----------+ 5460
       TACGAGCTTTATAAACGGTAAAAACAGATGTAACCATGAAAATCGATTAAGAAATAGCTA
          H  E  F  Y  K  G  N  K  D  V  N  T  S  K  A  L  E  K  D  I  -
                                                     ←

ACTATCAAGTTCTTCAGTACTCATTGCAACTGGTAACACTGTCGTTGATGATAGTTCTTT
 5461  ------------+----------+----------+----------+----------+----------+ 5520
       TGATAGTTCAAGAAGTCATGAGTAACGTTGACCATTGTGACAGCAACTACTATCAAGAAA
          S  D  L  E  E  T  S  M  A  V  P  L  V  T  T  S  S  L  E  K  -
                                                     ←
```

Figure 3I

```
       TTCAAGCAGATTGCGCACTTCATTTTCAATTTGACTTATTTCGTTCAATTGTGACACAAT
5521   ------------+----------+----------+----------+----------+----------+ 5580
       AAGTTCGTCTAACGCGTGAAGTAAAAGTTAAACTGAATAAAGCAAGTTAACACTGTGTTA
        E  L  L  N  R  V  E  N  E  I  Q  S  I  E  N  L  Q  S  V  I  -
                                            ←

TACTTCTGAAGCTTTCAATTGCTCTGGACTAGTTTTAGACAATTTTTGTTTTGGTTGCAA
5581   ------------+----------+----------+----------+----------+----------+ 5640
       ATGAAGACTTCGAAAGTTAACGAGACCTGATCAAAATCTGTTAAAAACAAAACCAACGTT
        V  E  S  A  K  L  Q  E  P  S  T  K  S  L  K  Q  K  P  Q  L  -
                                   ←

AGCAAATTCATTCATATTACTATTATTATTACTATTAGAAGAAGGAAACACGTTATCGGA
5641   ------------+----------+----------+----------+----------+----------+ 5700
       TCGTTTAAGTAAGTATAATGATAATAATAATGATAATCTTCTTCCTTTGTGCAATAGCCT
        A  F  E  N  M  N  S  N  N  N  S  N  S  S  P  F  V  N  D  S  -
                                       ←

TGCGTTATCACAATGATTGTCTATAACAGTACGAGACAAATTAGTAATATTTACAATAGG
5701   ------------+----------+----------+----------+----------+----------+ 5760
       ACGCAATAGTGTTACTAACAGATATTGTCATGCTCTGTTTAATCATTATAAATGTTATCC
        A  N  D  C  H  N  D  I  V  T  R  S  L  N  T  I  N  V  I  P  -
                                       ←

AAGAGATAAATTAGAAATATCATCATCATCGACGCTGTTCTNGTCATTATCATTTTTNGA
5761   ------------+----------+----------+----------+----------+----------+ 5820
       TTCTCTATTTAATCTTTATAGTAGTAGTAGCTGCGACAAGANCAGTAATAGTAAAAANCT
        L  S  L  N  S  I  D  D  D  D  V  S  N  ?  D  N  D  N  K  S  -
                                       ←
```

Figure 4

```
(SEQ ID NO. :8)   TTTTGCAAGAATATGAAGATTTCTCTCGTCGTGTTGAAAATTTGTAATAA    ELCAR
(SEQ ID NO. :9)   ..................................................    A44EB1
(SEQ ID NO. :10)  ..................................................    A44EA17
(SEQ ID NO. :11)  ..................................................    HaSAEA1

AACTAAATAAACCTTTAATATAAATATTAAACATACACTTTTATTTCTAA
                  ..................................................
                  ..................................................
                  ...C................XXXXXX.......................

AATAAGTATTTTTTTCCTATTGTTCAAGATTGTGAAAAATCAAATATCCC
                  ..................................................
                  ..................................................
                  ..................................................

ATA ATG TAT ACT CGT TAC AGT TAC AGC CCT ACT TTG GGC
                  ... ... ... ... ... ... ... ... ... ... ... ... ...
                  ... ... ... ... ... ... ... ... ... ... ... ... ...
                  ... ... ... ... ... ... ... ... ... ... ... ... ...

AAA ACC TAT GTG TAC GAC AAC AAA TAC TTT AAG AAT TTA
                  ... ... ... ... ... ... ... ... ... ... ... ... ...
                  ... ... ... ... ... ... ... ... ... ... ... ... ...
                  ... ... ... ... ... ... ... ... ... ... ... ... C..

GGT GCT GTT ATT AAA AAT GCC AAA CGC AAG AAG CAT TTA
                  ... ... ... ... ... ... ... ... ... ... ... ... ...
                  ... ... ... ... ... ... ... ... ... ... ... ... ...
                  ... ... ... ... ... ... ... ... ... ... ... ... ...

GAG GAG CAC GAA CAT GAA GAA CGC AAC TTG GAT TCG CTC
                  ... ... ... ... ... ... ... ... ..A ... ... ... ...
                  ... ... ... ... ... ... ... ... ..A ... ... ... ...
                  ... ... ... ... ... ... ... ... ... ... ... ... ...

GAC AAA TAC TTG GTG GCG GAA GAT CCT TTT TTG GGA CCT
                  ... ... ... ... ... ... ... ... ... ... ... ... ...
                  ... ... ... ... ... ... ... ... ... ... ... ... ...
                  ... ... ... ... ... ... ... ... ... ... ... ... ...

GGC AAA AAT CAA AAA CTA ACT TTG TTT AAA GAG ATT CGC
                  ... ... ... ... ... ... ... ... ... ... ... ... ...
                  ... ... ... ... ... ... ... ... ... ... ... ... ...
                  ... ... ... ... ... ... ... ... ... ... ... ... ...

AGC GTT AAG CCC GAC ACA ATG AAG CTT
                  ... ... ... ... ... ... ... ... ...
                  ... ... ... ... ... ... ... ... ...
                  ... ... ... ... ... ... ... ... ...
```

Figure 6A

```
                       10         20         30         40         50         60         70
(SEQ ID NO. :1) TTAATGAAAA TTTGTACATT TTTTATTCCT TTATTCAAAA TGAACTTGTT TTTTTTATTT ATTATTCCAA  1
(SEQ ID NO. :2)  M  K  I   C  T  F    F  I  P   L  F  K  M  N  L  F    F  L  F    I  I  P  T  2
(SEQ ID NO. :3) ---------- ---------- ---------- ---------- ---------- ---------- ----------  3
(SEQ ID NO. :4)  -  -  -   -  -  -    -  -  -   -  -  -  -  -  -  -    -  -  -    -  -  -  -  4

80         90        100        110        120        130        140
                CAATTTTAGC AGTTAAACCT TTTAGGTCTT TTAATAATAT TTCCTTAATT GATAATGGCA ATGTCGAATC  1
                 I  L  A   V  K  P    F  R  S  F  N  N  I  S  L  I    D  N  G  N  V  E  S   2
                ---------- ---------- ---------- ---------- ---------- ---------- ----------  3
                 -  -  -   -  -  -    -  -  -  -  -  -  -  -  -  -    -  -  -  -  -  -  -   4

150        160        170        180        190        200        210
                TGTAAGAGCA GTAGTTATTG ATTATTGTGA TATTAGACAT CCAAATAATT TATGTAAAAA ACATTTTGAA  1
                 V  R  A   V  V  I  D  Y  C  D   I  R  H   P  N  N  L  C  K  K   H  F  E   2
                ---------- ---------- ---------- ---------- ---------- ---------- ----------  3
                 -  -  -   -  -  -  -  -  -  -   -  -  -   -  -  -  -  -  -  -   -  -  -   4

220        230        240        250        260        270        280
                ATCGATTCAT ATTGGAATGA TGATACGGAT TGTTTTACAA ATATTGGATG CAAAGTATAT GGAGGATTTG  1
                 I  D  S  Y  W  N  D  D  T  D    C  F  T  N  I  G  C   K  V  Y   G  G  F  D  2
                ---------- ---------- ---------- ---------- ---------- ---------- ----------  3
                 -  -  -  -  -  -  -  -  -  -    -  -  -  -  -  -  -   -  -  -   -  -  -  -  4

290        300        310        320        330        340        350
                ATATTATTGG TGGTCATACC CCTAAAGTTG GAACTGTATG TAGACTTAAA AAAGGAGAAA ATAAATTTGG  1
                 I  I  G   G  H  T    P  K  V  G  T  V  C   R  L  K    K  G  E  N  K  F  G  2
                ---------- ---------- ---------- ---------- ---------A---- ---------- ----------  3
                 -  -  -   -  -  -    -  -  -  -  -  -  -   -  H  -    -  -  -  -  -  -  -   4

360        370        380        390        400        410        420
                ATATTGTAAT TCAAAGGGAA ATTGCGTTGA AAGAGATTTT AAAGAAAGTT TTGGAATATC TATAAAAATA  1
                 Y  C  N   S  K  G  N  C  V  E   R  D  F   K  E  S  F  G  I  S   I  K  I   2
                ---------- ---------- ---------- ---------- ---------- ---------- ----------  3
                 -  -  -   -  -  -  -  -  -  -   -  -  -   -  -  -  -  -  -  -   -  -  -   4

430        440        450        460        470        480        490
                AAAGGAATTT CTAATAAAGG AGATGATGAA CCAGCATGTC CACAATATAA AAATACTTGG ATTAATTATG  1
                 K  G  I  S  N  K  G   D  D  E   P  A  C  P  Q  Y  K   N  T  W   I  N  Y  G  2
                ---AT---AA --G------- ---AA----- ---------- --ATT---GG -------C--- ----------  3
                 -  I  -  T  D  -  -   E  N  -   -  -  -  -  I  -  G   -  -  -   -  -  -  -  4
```

Figure 6B

```
          500        510        520        530        540        550        560
     GGAAATGTAA TGAACCTTAT TATTGTGGAA CAAATCATGG ATTATTTTAT GCAAACAAAA GAAAACTCGA  1
      K  C  N    E  P  Y    Y  C  G  T   N  H  G    L  F  Y    A  N  K  R    K  L  D   2
     -A--------- ---------- C--------- --G------T- G-----A--- ---------- A---T--TC-    3
      -  -  -    -  -  -    H  -  -     D  -  W    -  L  -    -  -  -    K  N  L  H    4

570        580        590        600        610        620        630
     TTACTTTCCC ACAGACGGTG AAAAATGTAA TTCAAATAAT ATACCATATG CTGTTTGTTA TTTAGGAAGA  1
      Y  F  P    T  D  G  E   K  C  N    S  N  N    I  P  Y  A   V  C  Y    L  G  R   2
     --T-------T -----T---- ---------- ------A--- ---------- ---------- ----------    3
      F  -  -    -  -  -    -  -  -    -  L  -    -  -  -    -  -  -    -  -  -       4

640        650        660        670        680        690        700
     TGTCATACAA CAGGTGGTTT TTTTAGTGAA TTTGGAACTA TTGTTAAAAA TGTCGAAATC GTAACTTTAT  1
      C  H  T  T   G  G  F    F  S  E    F  G  T  I   V  K  N    V  E  I    V  T  L  S   2
     ---------- ----A----- ---------- --C------- ---------- ---------- ----------    3
      -  -  -  -   -  -  -    -  -  -    -  -  -  -   -  -  -    -  -  -    -  -  -  -   4

710        720        730        740        750        760        770
     CAGATGGAAA GAACAGTTCT AGAAGAGGAA AACATAAAAA TTTACCTACT TCTAAAGTAT TTGATAGTTA  1
      D  G  K    N  S  S    R  R  G  K    H  K  N    L  P  T    S  K  V  F    D  S  Y   2
     ---------- ---------- ---------- ---------- ---------- ---------- ----------    3
      -  -  -    -  -  -    -  -  -  -    -  -  -    -  -  -    -  -  -  -    -  -  -   4

780        790        800        810        820        830        840
     TAGTATATAT GATATTGATC CTAAAAATTG GAAAATTGAA GATGATGATA AAGATGTTAC TGTTCATGAA  1
      S  I  Y    D  I  D  P    K  N  W    K  I  E    D  D  D  K    D  V  T    V  H  E   2
     ---------- ---------- ---------- ---------- ---------- ---------- ----------    3
      -  -  -    -  -  -  -    -  -  -    -  -  -    -  -  -  -    -  -  -    -  -  -   4

850        860        870
     AATACATTAG ATCCAAAAAG TGATTCAAGA CTGTGTTAA  1
      N  T  L  D    P  K  S    D  S  R    L  C  *   2
     ---------- ---------- ---------- ---------    3
      -  -  -  -    -  -  -    -  -  -    -  -  *   4
```

RECOMBINANT HELICOVERPA BACULOVIRUSES EXPRESSING HETEROLOGOUS DNA

This application is a U.S. national stage application under 35 U.S.C. 371 of international application PCT/AU96/00535, filed Aug. 26, 1996.

This invention relates to the production of recombinant *Helicoverpa armigera* nuclear polyhedrosis viruses (HaSNPV) capable of expressing heterologous DNA sequences. In one particular application of the invention, the recombinant HaSNPVs are used as biological insecticides for the control of Heliothis and Helicoverpa pest species.

Nuclear polyhedrosis viruses (NPVs) are large double-stranded DNA viruses of insects and crustaceans in which the rod-shaped nucleocapsids are enclosed in a lipoprotein membrane. NPVs are a genus in the family Baculoviridae, and are characterised by multiple virus particles being occluded in a large, virally encoded, pseudo-crystalline protein matrix known as the polyhedron. Also included in the Baculoviridae are the granulosis viruses (in which only a single virus particle is occluded into the polyhedron) and the non-occluded baculoviruses (that produce no inclusion body at all).

The polyhedra of NPVs are characteristically polyhedral or cuboidal in shape and between 1–15 μm in diameter. Within the polyhedron the nucleocapsids are arranged in two distinct ways. In the case of the multiple enveloped NPVs (MNPVs) one or more nucleocapsids share the same lipoprotein membrane, while in the case of the single enveloped NPVs (SNPVs) each nucleocapsid has its own membrane. In both SNPVs and MNPVs the polyhedron itself is comprised almost entirely of a single protein, polyhedrin, encoded by a single viral gene. It is around this gene sequence, and in particular the DNA sequences (promoter) that control its expression, that technologies have been developed for the insertion of heterologous DNA sequences into the baculovirus genome. Indeed, three species of NPV namely Alfalfa looper *Autographa californica* (AcMNPV), the SNPV of the silkworm *Bombyx mori* (BmSNPV) and the SNPV of the corn earworm *Helicoverpa zea* (HzSNPV), have been engineered in this manner to express a wide range of viral, bacterial, plant and animal genes and have been expressed in permissive hosts in both cell culture and insects.

The promoters of genes other than polyhedrin have also been utilised for expression of heterologous DNA sequences in AcMPNV. For instance, the promoter of the gene, p10, has been used to express a wide range of genes and the promoters of basic core protein and ORF 603, has also been used to drive expression of reporter genes. Further, recombinant AcMNPVs have been constructed which contain synthetic promoters (Miller, 1990), modifications of existing promoter sequences (Kang, 1990) and heterologous promoters (Miller, 1991). It has also proven possible to add more copies of a promoter (Emery and Bishop, 1987; Takehara et al., 1988), in some instances up to three additional promoters, to allow the co-expression of up to four heterologous proteins (Belyaev and Roy, 1993).

Due to their high pathogenicity to insects, and the large range of insects from which baculoviruses have been isolated, several NPVs have been employed as biological insecticides. In a few cases these viruses have been applied over large areas to achieve insect pest control, and a proportion of these have been commercially or semi-commercially produced. Even though they are high infectious to their hosts, many baculoviruses can not be used for insecticidal purposes in their wild-type form as they take a relatively long time to kill an infected individual. Considerable interest has therefore been shown in the manipulation of baculoviruses, especially NPVs, to improve their speed of action. To achieve this, recombinant viruses have been generated that express heterologous DNA sequences encoding proteinaceous agents that are toxic or otherwise deleterious to their insect host. Such manipulations in AcMNPV include the insertion of genes encoding proteinaceous toxins from the straw itch mite *Pyemotes tritici* (Tomalski and Miller, 1991) and the scorpion *Androctonus australis* (Stewart et al, 1991). In these examples the expression of the heterologous DNA sequences led to significant reductions in the $LT_{50}$ (time at which 50% of the test organisms had died/been paralysed). In other examples, improved insecticidal properties have been achieved with heterologous genes that express proteins that disrupt the normal physiology and hormonal control mechanisms of the host. In one instance, a gene encoding juvenile hormone esterase (JHE) was expressed by a recombinant AcMNPV (Hammock et al. 1990) giving some improvement in insecticidal potential. In a later example, a recombinant AcMNPV expressing an inactive form of JHE gave further improvement in insecticidal potential. Further, Maeda (1989) demonstrated that a recombinant BmSNPV expressing a synthetic gene encoding the diuretic hormone of *Manduca sexta* reduced the time to death by about 20%.

It is noteworthy that not all toxin encoding genes that have been inserted into NPVs lead to the generation of recombinant viruses with improved insecticidal potential. Insertion of the gene encoding the delta-endotoxin of the entomopathogenic bacterium *Bacillus thuringiensis* subsp. kurstaki did not generate AcMNPV recombinants with improved insecticidal potential. Likewise, insertion of a gene synthesised from the known protein sequence of a proteinaceous toxin from the scorpion *Buthus europeus* did not improve the insecticidal potential of AcMNPV (Carbonell et al., 1988).

In most of the above examples, the virus is produced in cell culture and is genetically polyhedrin negative (pol−), with the inserted gene disrupting expression of the polyhedrin gene. Despite the fact that these viruses are incapable of occlusion, it has been found that pre-occluded viruses (POVs), that is viral progeny produced for inclusion into polyhedra, are infectious per os to their host organisms (Wood et al, 1993).

The insect genus Helicoverpa/Heliothis include a number of species which are major pests of broadacre crops. For the development of recombinant virus-based insecticides for these species, it is highly desirable that suitable viruses be identified which are infectious to most, if not all, of the major pest species but are not infectious to non-Helicoverpa/Heliothis insects. In this regard, it has been found that AcMNPV does not have an appropriate infectivity range.

For instance, Vail et al. (1978) demonstrated that *Helicoverpa zea* was between 12.9 and 68.9 times less susceptible to AcMNPV than was *Heliothis virescens*. Furthermore, we ourselves have shown that *H. armigera* is over a thousand (1,000) times less susceptible than *H. punctigera* to AcMNPV. In contrast, HzSNPV shows infectivity to most Helicoverpa/Heliothis species (with the notable exception of *H. subflexa* which is about 1000 fold less susceptible than any other species), but has not been found to infect any species outside of the subfamily Heliothinae. Consequently, HzSNPV appears to be a suitable candidate for development for use as a Helicoverpa/Heliothis specific insecticide.

The present invention have now identified a further candidate virus for the development of recombinant virus-based insecticides for Helicoverpa/Heliothis, in *Helicoverpa armigera* SNPV.

Accordingly, in a first aspect of the present invention relates to a recombinant HaSNPV characterised in that heterologous DNA is located in one or more non-essential regions of the viral genome, in a manner to permit the expression of the heterologous DNA, and wherein said recombinant HaSNPV is pol+.

Preferably, the recombinant HaSNPV is prepared from an HaSNPV isolate with a polyhedrin gene including a nucleotide sequence greater than 95% (more preferably, greater than 99%) homologous to any of the nucleotide sequences shown in FIG. 4. Alternatively, the recombinant HaSNPV is prepared from an HaSNPV isolate having a Bam H1 restriction fragment size profile as shown in Table 1, or includes a nucleotide sequence greater than 95% (more preferably, greater than 99%) homologous to the nucleotide sequence shown in FIG. 3.

Recombinant HaSNPV according to the invention may be used as biological insecticides, optionally in admixture with an acceptable agricultural carrier. The heterologous DNA inserted into the genome of the recombinant HaSNPV may comprise gene(s) encoding one or more substances that are deleterious to insects. Such substances include, insect specific toxins such as *Pyemotes tritici* tox 34-like toxins, insect neurohormomes or proteins which interact with such hormones (e.g., juvenile hormone esterase or juvenile hormone binding protein), or factors designed to attack and kill infected cells in such a way as to cause pathogenesis in the infected tissue (e.g., a ribozyme targeted against an essential cellular function). Expression of the heterologous DNA may be driven by the natural or other suitable promoter, but more preferably by an NPV promoter, particularly the polyhedrin promoter of HaSNPV.

Further, the recombinant HaSNPV according to the invention may be used for the production of desired, biologically active proteins, polypeptides or peptides, for example cytokines, insulin, growth hormones, antibodies and fragments thereof. Expression of the gene encoding the desired product may be driven by the gene's natural promoter or another suitable promoter, but more preferably expression is driven by an NPV promoter, particularly the polyhedrin promoter of HaSNPV. Recombinant HaSNPV's may be used to produce desired proteins and peptides by infecting cultured Helicoverpa cells, for example, cells comprising or derived from the Helicoverpa BCIRL-HZ-AM1 line.

The invention should further be understood as relating to method for producing desired proteins, polypeptides or peptides, comprising infecting susceptible host cells with a recombinant HaSNPV according to the first aspect of the invention.

The heterologous DNA is preferably located within a non-essential region selected from the regions encoding chitinase and the ecdysteroid UDP-glucosy transferase. Also, as shown hereinafter, heterologous DNA may also be located within a site located about 150 nucleotides upstream of the polyhedrin start codon, provided that expression of the adjacent 5' ORF is not disrupted. Locating the heterologous DNA within a non-essential region other than the polyhedrin-encoding region permits production of occluded pol+ recombinant viruses.

Regions suspected to be non-essential may be tested by:
isolating a genomic fragment containing the region to be tested, preferably with about 2 kb of flanking sequence on each side of the region,
inserting heterologous DNA (e.g. a reporter gene under the control of the polyhedrin promoter) into the region to generate a transfer vector,
co-transfecting suitable insect host cells with the transfer vector and viral DNA, and isolating recombinant viral clones that express the reporter gene.

The heterologous DNA is most conveniently inserted into the non-essential region of the HaSNPV by homologous recombination. Homologous recombination is preferably carried out in an infected permissive host cell line, by transfecting the host cell line with a construct wherein the heterologous DNA is flanked by a sequence of at least 5–10 nucleotides complementary to the sequence of the target, non-essential region.

In a yet further aspect, the invention also provides a method for controlling the proliferation of pest insects (particularly Lepidoptera), comprising applying to an infested area a recombinant HaSNPV or pre-occluded baculovirus according to the present invention, optionally in admixture with an acceptable agricultural carrier.

The term "substantially corresponding" as used herein in relation to nucleotide sequences is intended to encompass minor variations in the nucleotide sequence which due to degeneracy in the DNA code do not result in a change in the encoded protein, polypeptide or peptide. Further, this term is intended to encompass other minor variations in the sequence which may be required to enhance expression in a particular system but in which the variations do not result in a decrease in biological activity of the encoded protein, polypeptide or peptide.

The term "substantially corresponding" as used herein in relation to amino acid sequences is intended to encompass minor variations in the amino acid sequence which do not result in a decrease in biological activity of the encoded protein, polypeptide or peptide. The substitutions envisaged are:

G,A,V,I,L,M; D,E,N,Q; S,T; K,R,H; F,Y,W,H; and P, Nα-alkalamino acids.

The invention will now be further described by way of the accompanying figures and the following non-limiting examples.

BRIEF DESCRIPTION OF THE FIGURES

FIGS. 2A and 2B provide the nucleotide sequence of the A44EB1 polyhedrin gene and its flanking regions.

FIGS. 3A–3I provide the nucleotide sequence, and deduced amino acid sequence of the region surrounding the polyhedrin gene in the vector construct pA44ASL. Transcriptional direction of the putative open reading frames (ORFs) are shown by the symbols ← and →.

FIG. 4 shows the aligned sequences of the polyhedrin promoter and 5'250 bp of the polyhedrin coding sequence for a range of geographic isolates of Helicoverpa SNPVs.

FIGS. 6A and 6B provide the sequence of the *Pyemotes tritici* toxin gene Tox 34#4 and its relationship to the previously published sequence of Tomalski and Miller (1991). The sequence of Tox34#4 is shown in (1). (2) shows the deduced amino acid sequence. The published nucleotide sequence of Tomalski and Miller (1991) is shown in (3) and the deduced amino acid sequence in (4). In (3) and (4) where the amino acids match those of Tox 34#4 the position is marked with a dash (—); only where differences occur are they indicated by other characters.

EXAMPLE 1

Characterisation of HaSNPV

Virus

Figure 1:
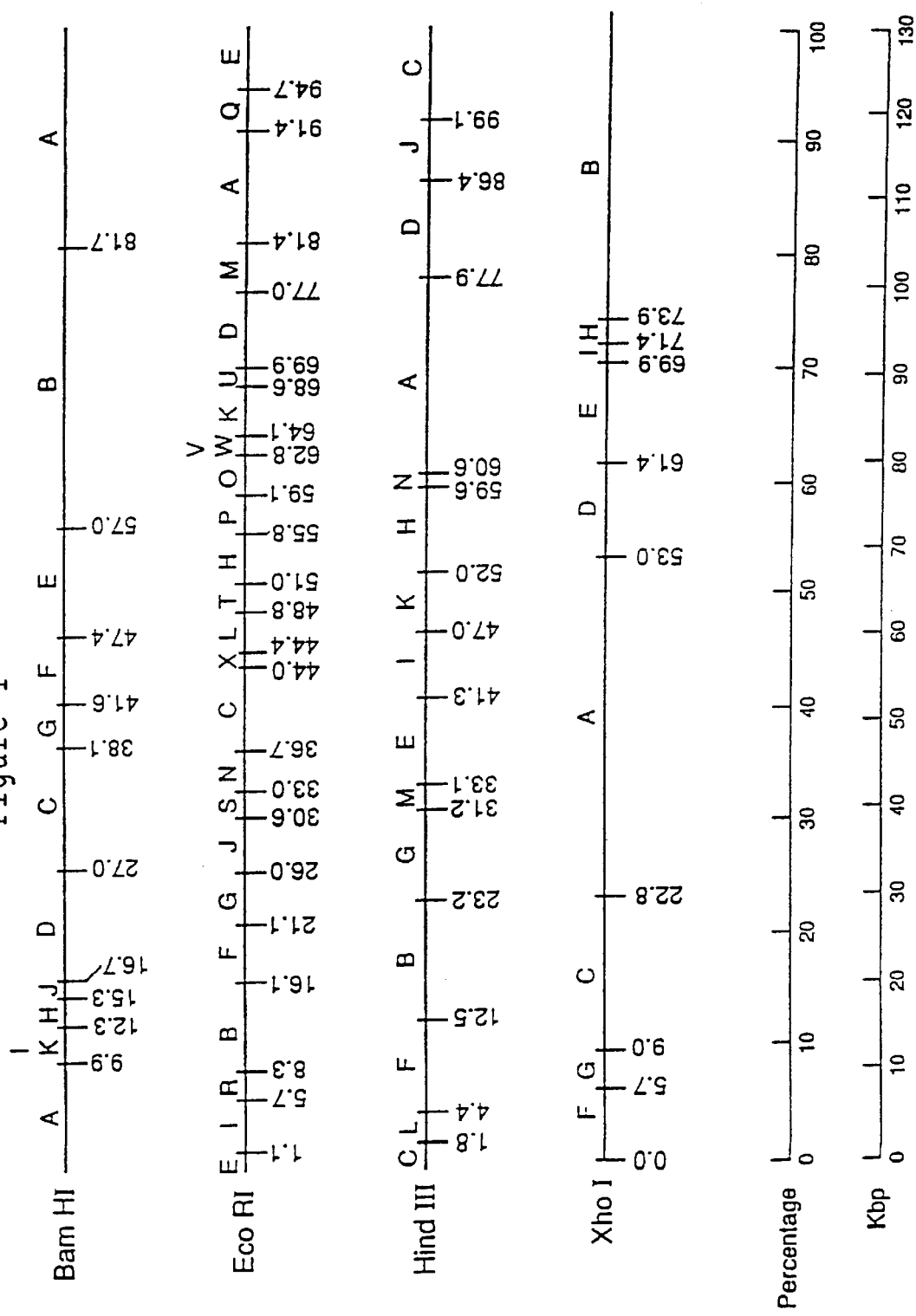
FIG. 1 shows a restriction map of A44EB1 for the enzymes Bam HI, Eco RI, Hind III and Xho I.

Wild-type HaSNPV was originally obtained from Dr Bob Teakle (Queensland Department of Primary Industry, Indooroopilly, Queensland). The wild-type isolate was passaged twice through five-day old (late third instar) *Helicoverpa armigera* larvae maintained from hatching at 25° C. on artificial diet (Shorey and Hale, 1965). Polyhedral inclusion bodies (PIBs) were purified by differential centrifugation. Restriction enzyme analysis revealed that the passaged wild-type isolate contained several genotypes.

To isolate individual genotypes, the product resulting from the above passages (A44) was subjected to end-point serial passage twice in *H. armigera* larvae (Smith and Crook, 1988). The virus receovered from a single larva, hereafter designated A44EB1, was then passaged once in third instar *Helicoverpa armigera* larvae at a rate of 100 PIBs/mm2, polyhedra purified, adjusted to a final concentration of $5\times10^9$ PIBs/ml and stored at 4° C.

DNA was prepared from this viral suspension in the following manner. One ml of the virus suspension is added to 500 ml of dissolution buffer (0.3M $Na_2CO_3$, 0.03M EDTA, 0.51M NaCl) and incubated at 37° C. for 1 hour. This suspension is clarified by centrifugation at 3,000×g for 5 minutes. Virus particles are then precipitated from the supernatant by centrifugation at 14,000×g for 30 minutes at 4° C. The resulting pellet was resuspended overnight in 200µl of sterile TE (0.01M Tris-HCl pH 7.4, 0.001 M EDTA).

An equal volume of NOV digestion buffer (0.01 M Tris-HCl, pH 7.4, 0.001 M EDTA, 0.2% KCl, 0.2% sarkosyl) was added to the NOV suspension along with 4 µl of Proteinase K solution (10 mg/ml in TE; TE=0.01 M Tris-HCl, pH7.4, 0.001 M EDTA). This reaction was then incubated at 65° C. for 2–3 hours. The DNA was extracted twice with two volumes of phenol:CIA (1:1) (CIA= chloroform:iso-amyl alcohol, 24:1). The DNA was then dialysed against sterile distilled water overnight (Horowitz and Barnes, 1983).

Restriction analysis of HaSNPV

A44EB1 virus DNA was digested with restriction enzymes in accordance with the manufacturers instructions. Restriction digestion fragments were separated by electrophoresis through 0.7% horizontal agarose gels at 1.5–2.5 V/cm for 16–18 hours in Tris/acetate/EDTA (TAE) buffer. DNA bands were visualised under medium range ultraviolet light after staining with ethidium bromide (1.5 µg/ml).

Construction of HaSNPV Physical Map

All Eco RI, Hind III and Xho I genomic restriction fragments from A44EB1 under 20 Kbp in size, were cloned into the plasmid vector Bluescript M13+ (pBSM13+). Ligation mixes were transformed into *Escherichia coli* strain TG-1 using the method of Morrison (1979). Recombinant plasmids were prepared according to the alkaline lysis method of Birnboim and Doly (1979).

A preliminary restriction map of the HaSNPV genome was deduced by hybridising each Eco RI clone to souther blots of HaSNPV genomic DNA digested with Bam HI, Eco RI, Hind III and Xho I. The molecular weights of fragments generated by the above digestions are shown in Table 1.

TABLE 1

Molecular size (Kbp) of HaSNPV restriction fragments. All fragment sizes were determined by agarose gel electrophoresis of restricted genomic DNA and cloned genomic fragments.

| FRAGMENT | BamHI | EcoRI | HindIII | XhoI |
|---|---|---|---|---|
| A | 36.7 | 13.0 | 22.5 | 39.2 |
| B | 32.1 | 10.2 | 14.0 | 33.9 |
| C | 14.6 | 9.6 | 13.0 | 18.1 |
| D | 13.6 | 9.2 | 11.0 | 11.0 |
| E | 12.5 | 8.4 | 10.6 | 11.0 |
| F | 7.7 | 6.4 | 10.5 | 7.3 |
| G | 4.5 | 6.3 | 10.3 | 4.4 |
| H | 3.9 | 6.25 | 9.8 | 3.3 |
| I | 1.9 | 6.0 | 7.5 | 2.1 |
| J | 1.8 | 5.9 | 7.1 | |
| K | 1.25 | 5.9 | 6.3 | |
| L | | 5.7 | 3.3 | |
| M | | 5.7 | 2.6 | |
| N | | 4.8 | 1.3 | |
| O | | 4.5 | | |
| P | | 4.35 | | |
| Q | | 4.35 | | |
| R | | 3.4 | | |
| S | | 3.1 | | |
| T | | 2.9 | | |
| U | | 1.75 | | |
| V | | 1.0 | | |
| W | | 0.7 | | |
| X | | 0.45 | | |
| TOTAL | 130.5 | 129.85 | 129.8 | 130.3 |

Electrophoretically separated viral DNA fragments were transferred to Hybond-N (Amersham, U.K.) membrane and then, hybridisations for mapping were carried out overnight at 65° C. in the presence of 0.6M sodium chloride, 0.1% sodium pyrophosphate, and filters washed at 45° C. in 0.3M sodium chloride, 0.03M sodium citrate, pH 7.5, 0.1% SDS. Cloned viral DNA was nick-translated in the presence of [α-32P]dATP to produce 32P-labelled hybridisation probes.

Although the sizes of fragments greater than 10 kbp were estimated from agarose gels, their size was ultimately deduced from the size of their component Eco RI fragments. The preliminary map was refined by digestion of individual cloned restriction fragments with various single and double combinations of enzymes. The final restriction map of the HaSNPV genome is presented in FIG. 1. The orientation of the restriction map was determined by Southern hybridisation to an AcMNPV polyhedrin gene probe and the presumed direction of transcription of the polyhedrin gene (see below).

The restriction map of A44EB1 is similar to that previously described for HzSNPV (an isolate derived from the commercially produced insecticide ELCAR™ and propagated in *H. virescens* larvae.) However, it does differ in several important respects most notably in the absence of Bam HI site in the region 11.6–18.5 and in the presence of an additional Eco RI site in the region 46.3–50.6 (map units are as presented in Knell and Summers, 1984). Allowing for the slight differences in absolute size obtained between laboratories in mapping studies, comparison of the HzSNPV and HaSNPV map using the RESTSITE program of Miller and Nei (1990) provides an overall nucleotide divergence between the viruses of 0.45%. In contrast, direct comparison of virus derived from ELCAR™ and A44EB1 by restriction endonuclease (REN) analysis gives a nucleotide divergence of 0.98%.

To isolate the fragment carrying the A44EB1 polyhedrin gene, Eco RI generated fragments of AcMNPV genomic DNA were cloned into the plasmid vector pBSM13+ as described above. A 250 bp EcoRV-BamHI fragment containing the partly deleted polyhedrin gene of AcMNPV, was removed from the plasmid construct pACYM1 (supplied by Dr D. H. L. Bishop, Institute of Virology, Oxford, U.K.). The EcoRI fragment of AcMNPV containing the polyhedrin gene was identified from the AcMNPV Eco RI library, hybridisation was carried out with the 250 b.p. fragment of pACYM1. From the clone selected, a 350 bp fragment of the AcMNPV polyhedrin gene, containing 100 bp of 5' flanking sequence and 250 bp of the polyhedrin coding region, was used as a hybridisation probe to select the polyhedrin gene containing clone from the A44EB1 EcoRI generated library. The latter hybridisation was performed at 42° C. in 0.6M sodium chloride, 0.1% sodium pyrophosphate and washed at room temperature in 0.3M sodium chloride, 0.03M sodium citrate, pH 7.5, 0.1% SDS.

Sequencing of the Polyhedrin Gene of A44EB1

The Eco RI clone containing the putative A44EB1 polyhedrin gene was digested with a variety of enzymes and Southern hybridisation performed with the 350 b.p. fragment from AcMNPV. Viral DNA fragments were excised from pBSM13+ clones and cloned into the phagemid pTZ 18/19. Sequencing was carried out using the dideoxy method of Sanger et al. (1977) with the T7 sequencing kit (Pharmacia, Uppsala, Sweden) and [α-35S]dATP. Nucleotide sequences and deduced amino-acid sequences were aligned using the University of Wisconsin sequence analysis package, GCG. The sequence of the A44EB1 polyhedrin gene is presented in FIG. 2.

Further to this, approximately 2.0 Kb either side of the polyhedrin gene was sequenced (FIG. 3).

Comparison with other HaNPVs

HaSNPVs isolated from *Helicoverpa armigera* in India (HaSNPVIn) South Africa (HaSNPVSA) and China (HaSNPVCh) were provided by Dr Bill McCarthy (Pennsylvania State University, Pennsylvania, U.S.A.). A sample of the commercial preparation of HzSNPV (ELCAR™) was provided by Dr. Bob Teakle (Queensland Department of Primary Industry, Indooroopilly, Queensland) along with an SNPV isolated from *Helicoverpa assulta* HasSNPVE19. These wild-type isolates were passaged twice through third instar *H. armigera* larvae and polyhedral inclusion bodies (PIBs) purified by differential centrifugation. Individual genotypes were purified by limiting end-point dilution in third instar larvae by the method of Smith and Crook (1988), and propagated at high concentration (100 PIBs/mm$^2$) in third instar larvae. The resulting isolates from the original Indian, South African, Chinese and *Helicoverpa assulta* preparations are termed HaInEA1, HaSAEA1, HaChEE1 and E19EA2 respectively.

DNA purified from the above isolates were digested with the restriction enzymes Xho I, Eco RI, Hind III, BamHI and EcoRV and fragments separated on 0.8% agarose gels in TAE buffer. DNA from A44EB1 was included in the analysis along with another isolate derived in parallel with A44EB1 namely, A44EA17. Fragments that were readily resolved below 12 kbp were scored for presence or absence in each of the isolates. Co-migrating bands were scored as homologous. These fragment data were used to estimate average nucleotide divergence between isolates (d hat) using the RESTSITE program of Nei and Miller (1990). The resulting distance matrix for some of these isolates is shown in Table 2.

TABLE 2

Distance matrix of average percent nucleotide substitutions (d hat) between various geographic isolates of Helicoverpa SNPVs.

|         | A44EB1 | E19EA2 | ELCAR  | HaCHEE1 |
|---------|--------|--------|--------|---------|
| E19EA2  | 0.0126 |        |        |         |
| ELCAR   | 0.0098 | 0.0180 |        |         |
| HaChEE1 | 0.0267 | 0.0239 | 0.0245 |         |
| HaINEA1 | 0.0271 | 0.0360 | 0.0250 | 0.0377  |

These data show that Helicoverpa/Heliothis SNPVs have similar restriction profiles over a wide geographic range that translates to between 1–4% divergence at the nucleotide level.

The Hind III fragments restriction fragments encoding the 5' end of the polyhedrin gene were also cloned from some of the above isolates and the 5' 250 bp coding and 160 bp upstream sequences determined. These sequences are shown in FIG. 4.

These data indicate that the polyhedrin gene and its 5' region are much more highly conserved than the rest of genome as indicated by restriction enzyme analysis.

Host Range and Biological activity of HaNPV

The biological activity of A44EB1 was tested against *Helicoverpa armigera, H. punctigera, H. zea, H. virescens* and *Heliothis subflexa*. Included for comparison in these tests was AcMNPV. Before use in these comparative tests AcMNPV was passaged three times in fourth instar *Triochoplusia ni* at high concentrations (100 PIBs/mm2). Bioassays were carried out on mid first instar Helicoverpa/Heliothis larvae using the surface contamination methods of Ignoffo et al. (1976; 1983). An untreated control was also included. All larvae were maintained at 30° C. and monitored regularly for viral deaths. Final mortality was scored at 10 days post-infection. The results of these bioassays are presented in Table 3. These data show that A44EB1 has better activity against the major heliothine pest species (*H. armigera, H. punctigera, H. virescens* and *H. zea*) than does AcMNPV.

TABLE 3

$LC_{50}$s for A44EB1 and AcMNPV against a range of Helicoverpa/Heliothis larvae.

|             |              | VIRUS A44EB1 | AcMNPV       |
|-------------|--------------|--------------|--------------|
| H. armigera | $^{(1)}LC_{50}$ | 0.224        | $^{(4)}$>800.00 |
|             | $^{(2)}$95% C.L. | 0.162–0.314  | N/A          |
|             | Slope (b)    | 1.366        | N/A          |
|             | $^{(3)}$+/− slope | 0.147        | N/A          |
| H. punctigera | $LC_{50}$  | 0.384        | 0.667        |
|             | 95% C.L.     | 0.216–0.683  | 0.283–1.186  |
|             | Slope (b)    | 1.515        | 1.177        |
|             | +/− slope    | 0.182        | 0.148        |
| H. zea      | $LC_{50}$    | 0.018        | 0.088        |
|             | 95% C.L.     | 0.011–0.026  | 0.003–0.310  |
|             | Slope (b)    | 1.568        | 0.607        |
|             | +/− slope    | 0.175        | 0.088        |
| H. virescens | $LC_{50}$   | 0.072        | 0.286        |
|             | 95% C.L.     | 0.039–0.132  | 0.100–0.919  |
|             | Slope (b)    | 1.687        | 1.273        |
|             | +/− slope    | 0.185        | 0.163        |

TABLE 3-continued

LC$_{50}$s for A44EB1 and AcMNPV against a range of Helicoverpa/Heliothis larvae.

| | | VIRUS A44EB1 | AcMNPV |
|---|---|---|---|
| H. subflexa | LC$_{50}$ | [5]>10.000 | 0.106 |
| | 95% C.L. | N/A | 0.059–0.186 |
| | Slope (b) | | 1.713 |
| | +/- slope | | 0.323 |

[1]LC$_{50}$ calculated from at least two replicates of at least four dilutions. LC$_{50}$ calculated by probit analysis and expressed in PIBs/mm2. All data were generated from bioassays performed on 24 hour old (mid first instar) larvae at 30° C. using the diet surface contamination method
[2]95% C.L. - 95% confidence limits
[3]standard error of the slope
[4]Approximately 25% mortality at 800 PIBs/mm2
[5]At 100 PIBs/mm2 A44EB1 gives mortality between 50% and 99%.

Growth of HaSNPV in Cell Culture

The *Helicoverpa zea* cell line Hz-BCIRL-AM1 was obtained from Dr Art McIntosh (USDA, Biological Control, of Insects Research Laboratory, Columbia, Mo.) and maintained in TC199MK media (McIntosh et al., 1973). Infection in these cells was initiated in the following fashion. Approximately 5×10$^9$ PIBs were dissolved in polyhedral dissolution buffer at room temperature for 15 minutes. Debris and undissolved polyhedra were removed by centrifugation at 5,000×g for five minutes and virus particles sedimented from the resulting supernatant by centrifugation at 15,000×g for 30 minutes.

The virus particles were resuspended in 1 ml of TC199MK media and layered onto a monolayer of Hz-BCIRL-AM1 (5×10$^5$ cells) in a 25 cm$^2$ tissue culture flask. After absorption for 1 hour the cells were washed with fresh media and then incubated at 29° C. until polyhedra appeared in the nuclei of the cells. The supernatant was then collected and stored at −20° C. Reference virus was produced by passage of the above supernatant through Hz-BCIRL-AM1 cells at an m.o.i. of 1.0 and collection of cell supernatants at 4 days post infection.

DNA purified as described above was used to produce productive infections in Hz-BCIRL-AM1 cells by transfection with the lipid transfection reagents DOTMA and DOTAP (Boehringer Mannheim). Briefly, 150 ng of viral DNA was mixed with the reagent as per the manufacturers instruction. This viral DNA-lipid emulsion was then added to cells in TC199MK media without foetal calf serum (FCS) and left at 29° C. for 16 hours, after which the transfection reagent and media were removed and replaced with fresh, TC199MK media containing FCS.

Because of the apparent heterogeneity of the Hz-BCIRL-AM1 cell line, clonal cell lines were generated in the following manner. A cell suspension was diluted to give a final concentration of approximately 1 cell/100 μl. Fifty microliter aliquots of this suspension were dispensed into a 96 well microtitre plate and each well scored for the number of cells present. The cells in each of those wells containing only single cells were propagated until reaching a density at which they could be frozen for long-term storage in liquid nitrogen. This process yielded a total of 28 clonal cell lines.

Each of these clonal lines was then assessed for; division time, sensitivity to infection with A44EB1, ability to be transfected with the lipid based reagent DOTAP (Boehringer Mannheim), and PIB production. The results from these studies are presented in Table 4.

TABLE 4

Growth and virus production characteristics of clonal *Helicoverpa zea* cell lines.

| | [1]Division Time Days (±SD) | | [2]TCID$_{50}$ | [3]DOTAP | PIB Production [4](PIBs/cell) (±SD) | |
|---|---|---|---|---|---|---|
| Parental | 1.47 | (0.13) | +++ | + | 188.10 | (82.85) |
| IC10 | 1.66 | (0.17) | +++ | − | 78.35 | (16.21) |
| 1D6 | 1.50 | (0.18) | ++ | + | 138.13 | (65.57) |
| 2B2 | 1.98 | (0.28) | +++ | s | 176.36 | (95.90) |
| 2C3 | 1.88 | (0.10) | ++ | + | 347.01 | (116.39) |
| 2C10 | 2.02 | (0.18) | + | + | 159.61 | (65.60) |
| 2D2 | 2.03 | (0.23) | ++ | +s | 127.25 | (48.34) |
| 2E3 | 1.86 | (0.25) | ++++ | + | 120.00 | (59.68) |
| 2E5 | 1.94 | (0.17) | ++ | s | 161.86 | (68.23) |
| 2E10 | 1.80 | (0.21) | + | − | 340.75 | (69.35) |
| 2F3 | 1.93 | (0.37) | + | | 29.79 | (18.98) |
| 2F8 | 1.81 | (0.15) | ++ | − | 27.25 | (21.31) |
| 2F9 | 1.95 | (0.20) | + | + | 245.24 | (114.85) |
| 2G11 | 2.03 | (0.28) | +++ | + | 27.30 | (10.52) |
| 3B2 | 1.99 | (0.22) | ++++ | + | 148.00 | (81.43) |
| 3B5 | 1.85 | (0.28) | +++ | + | 108.04 | (102.87) |
| 3B7 | 1.90 | (0.12) | +++ | s | 124.81 | (79.25) |
| 3C7 | 1.93 | (0.16) | ++ | + | 128.70 | (78.22) |
| 3C8 | 1.53 | (0.14) | +++ | + | 125.40 | (16.24) |
| 3D7 | 1.75 | (0.16) | +++ | + | 77.11 | (26.45) |
| 3D11 | 1.89 | (0.16) | + | + | 64.79 | (30.06) |
| 3E2 | 2.06 | (0.18) | +++ | + | 138.78 | (52.34) |
| 3E4 | 2.21 | (0.20) | + | + | 112.86 | (54.66) |
| 5B8 | 2.23 | (0.08) | +++ | + | 48.76 | (30.77) |
| 5B11 | 1.55 | (0.12) | +++ | − | 199.52 | (161.54) |
| 5D4 | ND | | +++ | + | 169.09 | (67.73) |
| 5F10 | ND | | +++ | + | 91.00 | (20.62) |
| 5G3 | ND | | + | s | 264.54 | (147.25) |

Figure 5A:
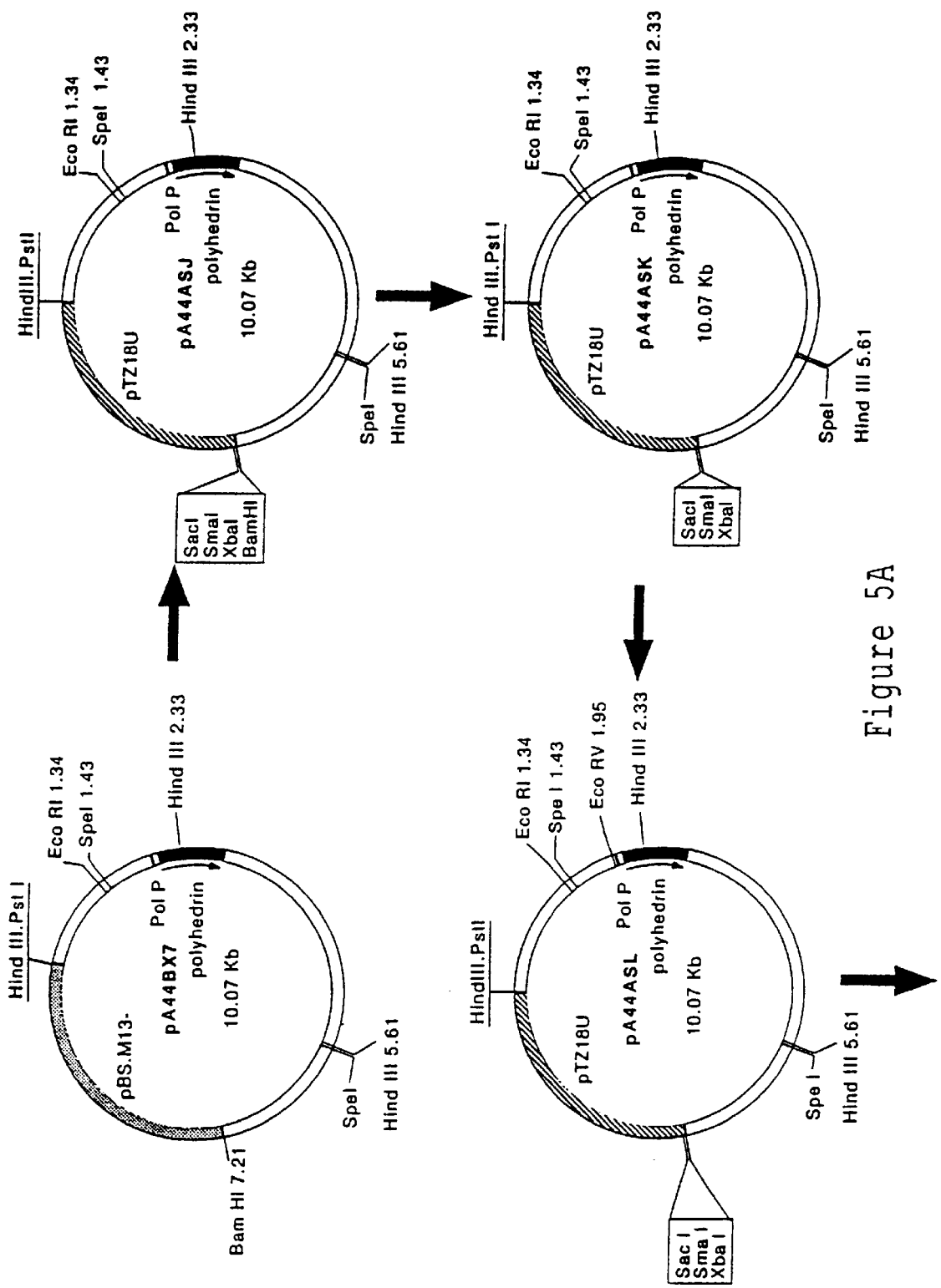
FIGS. 5A and 5B outline the construction of pol− HaSNPV transfer vectors.
Figure 5B:
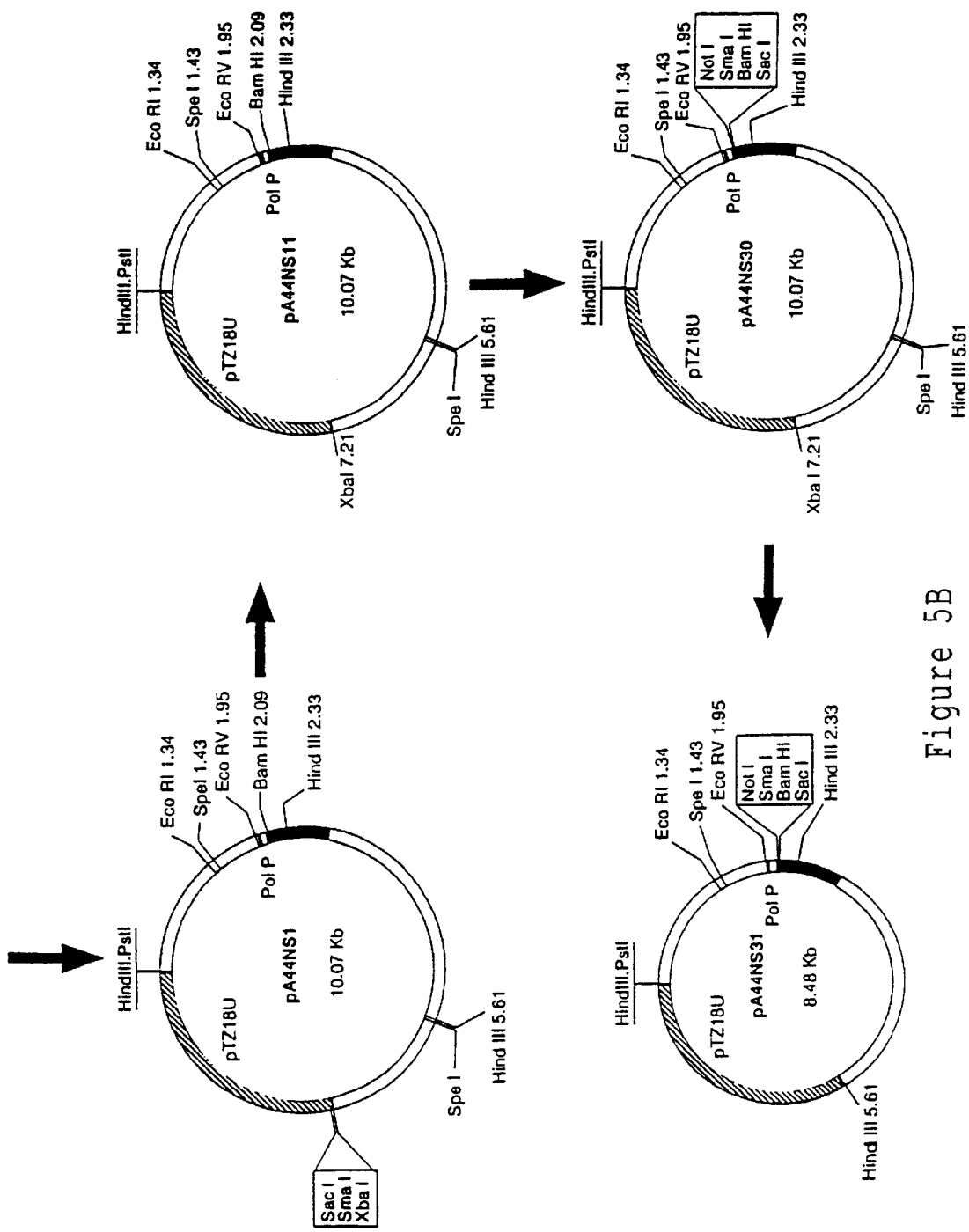

[1]Division times are given in hours. ND = not determined
[2]The TCID$_{50}$ of a standard inoculum of A44EB1 was determined in each of the cell lines.
++++ = greater than titre obtained in parental (*H. zea*) line; +++ = equal to the titre obtained in the parental line; ++ = fourfold to tenfold lower than titre obtained in the parental line; + = more than tenfold lower than titre obtained in the parental line.
[3]Ability to be transfected with the lipid based reagent DOTAP (Boehringer Mannheim). s = sensitive to the reagent.
(4)The number of PIBs produced by each cell. The number of cells was taken as those present at infection (infected with A44EB1 at an m.o.i. of 5.0). Replicates were performed in 6 well tissue culture trays and PIBs were harvested at 4 day post infection These data show that there is considerable variation amongst these lines in the parameters that were measured, suggesting that these lines may have utility for the performance of different functions in the generation, selection and production of recombinant HaSNPV.

Example 2

Recombinant HaNPVs Expressing the esterase-6 (Est-6) gene, the b-galactosidase (Gal) gene or the b-glucuronidase gene (GUS)

The 7.0 kbp Xho I fragment containing the whole of the polyhedrin gene and promoter was cloned into the bacterial plasmid pBluescript SK- (pA44BX7; FIG. 5). The viral fragment was removed from this plasmid by digestion with Bam HI and Pst I and inserted between the Pst I and Bam HI sites of the plasmid pTZ19U (pA44ASJ; FIG. 5). The Bam HI site remaining in the plasmid vector was destroyed by Bam HI digestion, end-filling using the Klenow fragment of DNA polymerase I and subsequent religation of the blunt-ended linear DNA (pA44ASK: FIG. 5).

A unique Eco RV site was introduced into the transfer vector at position −150 upstream of the polyhedrin start codon (ATG) by in vitro site directed mutagenesis using the oligonucleotide 5'-TATGAAGATATCTGTCGT-3' (pA44ASL: FIG. 5) (SEQ ID NO:12).

A unique Bam HI site was then introduced into the region around the ATG of the polyhedrin coding region by site directed mutagenesis using the oligonucleotide 5'-TCCCATAAAGGATCCTCGTTACAG-3' (pA44NS1: FIG. 5) (SEQ ID NO:13). Sma I and Sac I sites were removed from the transfer vector pA44NS1 by digestion with Sma I and Sac I, end-filling using the Klenow fragment of DNA polymerase I, and subsequent religation of the blunt-ended linear DNA (pA44NS11: FIG. 5).

A polylinker was made for insertion into pA44NS11 by annealing the oligonucleotides:
5'-GATCGCGGCCGCCCGGGATCCGAGCTC-3' (SEQ ID NO:14) and
5'-GATCGAGCTCGGATCCCGGGCGGCCGC-3' (SEQ ID NO:15)
and ligating the resulting dsDNA fragment into the Bam HI site of pA44NS11 (pA44NS30; FIG. 5). The polylinker introduced by the above procedure introduced additional Not I, Sma I, Bam HI and Sac I sites adjacent to the polyhedrin promoter.

To allow the insertion of larger DNA fragments, a 1.6 kbp fragment was removed between map positions 5.6 and 7.2 in the transfer vector pA44NS30. This was achieved by digestion of the transfer vector with Xba I, partial digestion with Spe I and religation of the 8.5 kbp fragment (pA44NS31; FIG. 5).

To generate a recombinant HaSNPV expressing the esterase-6 gene from *Drosophila melanogaster* (pE6) (Oakeshott et. al., 1987) a 1.6 kbp cDNA fragment containing the whole of the esterase-6 gene was inserted into the transfer vector pA44NS1. This was achieved by digesting the clone containing the Est-6 coding sequence with Eco RI, end-filling the fragment using the Klenow fragment of DNA polymerase I and then ligating it into the Bam HI site of the transfer vector which had been end-filled using the Klenow fragment of DNA polymerase I. This transfer vector along with A44EB1 viral DNA was transfected into *H. zea* cells, and recombinants were selected by serial end-point dilution and screening of the resultant supernatants on Titan-III cellulose acetate gels stained for esterase. Esterase-6 from *D. melanogaster* migrates much slower than any endogenous esterases in the cells and recombinants are readily identified.

To generate a recombinant virus expressing the b-galactosidase from the bacterium *E. coli,* a fragment containing the whole of b-galactosidase coding sequence was removed from the plasmid pGH101 (Herman et al., 1986) by digestion with Bam HI. This fragment was ligated into the Bam HI site of pA44NS1. This transfer vector along with A44EB1 viral DNA was transfected into *H. zea* cells, and recombinants selected by serial end-point dilution and their ability to express b-galactosidase that catalyses X-gal (5-Bromo-4-chloro-3-indolyl-b-D-galactopyranoside).

To generate a recombinant virus expressing the beta-glucoronidase (Gus; Jefferson, 1987) gene originally isolated from the bacterium *Escherichia coli,* a fragment containing the whole of b-glucoronidase coding sequence was inserted into the Bam HI site of pA44NS3. This transfer vector along with A44EB1 viral DNA was transfected into *H. zea* cells, and recombinants selected by serial end-point dilution and their ability to express b-glucoronidase that catalyses t-Gluc (5-Bromo-4-chloro-3-indolyl-b-D-glucuronic acid).

Recombinants containing esterase-6, b-galactosidase and b-glucoronidase are hereinafter referred to as A44NS1-E6, A44NS1-Gal and A44NS31-Gus respectively.

All of the above recombinant viruses were taken through three rounds of serial end-point dilution and individual clones were then propagated in Hz-BCIRL-AM1 cell line to high titres. Titred stocks were stored frozen at $-20°$ C. until required for further use.

For infectivity studies 25 cm$^2$ flasks containing $5\times10^5$–$1\times10^6$ Hz-BCIRL-AM1 cells were infected with one of the recombinant viruses A44NS1-Gal, A44NS1-E6 or A44NS31-Gus. Four days after infection the supernatant was harvested and an additional 5 ml of fresh media added. Twenty-four hours later the cells were harvested using a cell-scraper and stored at 4° C. until further use.

For bioassays, cell suspensions harvested as described above, were diluted in sterile phosphate buffered saline and then 100 microliters of the appropriate dilution was spread on the surface of standard insect diet (lacking formalin) (Shorey & Hale, 1965) dispensed into J2 jelly cavities (Nu-trend Containers, Jacksonville, Fla.). Individual larvae were placed into each cavity and the cavity sealed with heat-sealable Mylar™ (DuPont). Larvae were monitored for viral death at regular intervals over ten days, at which time the assays were terminated. $LC_{50}$'s were determined by probit analysis using the POLO program (Russell et al, 1977) while $LT_{50}$'s were estimated graphically.

In a first experiment, A44NS1-Gal and A44NS31-Gus were bioassayed against 24 hour old *H. armigera*. For A44NS1-Gal an $LC_{50}$ of 0.00485 (b=0.760+/−0.247) was obtained while for A44NS31-Gus and $LC_{50}$ of 0.00275 (b=1.527+/−0.247) was obtained. From these bioassays, $LT_{50}$'s were deduced of 3.7 days and 3.9 days for A44NS1-Gal at doses of 8.25 and 1.65 $LC_{50}$'s/well respectively and 3.7 days and 3.9 days for A44NS31-Gus at doses of 14.55 and 2.91 $LC_{50}$'s/well respectively.

The number of $LC_{50}$'s/well were calculated from: dosage applied/the estimated $LC_{50}$.

Surprisingly, in these experiments it was noted that the $LT_{50}$'s obtained were lower than had previously been observed in bioassays carried out with the wild-type A44EB1. In one such experiment an $LC_{50}$ of 0.06786 PIBs/mm$^2$ was obtained (b=1.335+/−0.286), with derived $LT_{50}$'s of 4.3 days, 4.8 days and 5.5 days at 14.9, 5.9 and 1.5 $LC_{50}$'s/well. Therefore, from these data it would appear that A44EB1 produced in a non-occluded recombinant form, lacking polyhedrin and expressing another protein in its place, has a faster rate of kill than the normal, polyhedrin producing, wild-type virus. Baculovirus produced in this non-occluded form from intact insects cells prior to lysis have been termed pre-occluded viruses (POVs) (Wood et al, 1993).

To further test the utility of recombinant A44EB1 NOVs, bioassays were carried out on a range of instars of both *H. armigera* and *H. punctigera*. The data from these tests are summarised in Table 5 and clearly show that POVs generated from A44EB1-derived recombinants viruses are infectious against a wide range of larval instars of both *H. armigera* and *H. punctigera*.

TABLE 5 bioassays conducted against *H. armigera* and *H. punctigera* with recombinant HaNPVs expressing β-galactosidase and β-glucoronidase.

| Bioassay Species | [1]Inst | [2]Virus | [3]LC$_{50}$ | [3]95% CL (Lower) (Upper) | Slope (b) (+/−) | [4]LT$_{50}$ | [4]Dose |
|---|---|---|---|---|---|---|---|
| *H. armigera* | M1 | A44NS31-Gus | 0.00275 | 0.00181 | 1.527 | 3.7 | 14.55 |
|  |  |  |  | 0.00411 | 0.247 | 3.9 | 2.91 |
| *H. armigera* | M1 | A44NS1-Gal | 0.00485 | 0.00244 | 0.760 | 3.7 | 8.25 |
|  |  |  |  | 0.01028 | 0.247 | 3.9 | 1.65 |
| *H. armigera* | L2 | A44NS1-Gal | 0.01199 | 0.00817 | 1.749 | 5.1 | 3.3 |
|  |  |  |  | 0.01832 |  |  |  |
| *H. armigera* | L2 | A44NS31-Gus | 0.00705 | 0.00384 | 1.107 | 4.7 | 5.7 |
|  |  |  |  | 0.01245 | 0.283 | 5.1 | 1.1 |
| *H. punctigera* | M1 | A44NS31-Gus | 0.00185 | 0.00079 | 1.540 | 3.7 | 21.6 |
|  |  |  |  | 0.00304 | 0.377 | 4.9 | 4.3 |
| *H. punctigera* | M1 | A44NS31-Gus | 0.01722 | 0.00851 | 0.788 | 4.9 | 1.5 |
|  |  |  |  | 0.06579 | 0.215 |  |  |
| *H. punctigera* | M1 | A44NS31-Gus | 0.00594 | 0.00449 | 2.622 | 4.2 | 4.2 |
|  |  |  |  | 0.00788 | 0.453 | 4.1 | 1.1 |
| *H. punctigera* | L2 | A44NS31-Gus | 0.00537 | 0.00319 | 1.305 | 3.6 | 18.6 |
|  |  |  |  | 0.00909 | 0.220 | 4.5 | 1.9 |

[1]Larval instars are as follows; M1 = mid-first instar, L2 = late second instar
[2]Each experiment was performed with a different POV preparation
[3]LC$_{50}$ and 95% confidence limits were calculated using the probit analysis program POLO (Russell et al. 1977). All values are expressed as a dilution of the original POV preparation
[4]LT$_{50}$'s are expressed in days for the doses shown (expressed as number of LC$_{50}$s/well)

Example 3
Cloning of a gene encoding a proteinaceous toxin from *Pyemotes tritici*

Total RNA was extracted from *Pyemotes tritici* obtained from Biofa Inc. (Mathis, Tex.) using a guanadinium isothiocyanate-sarcosine protocol as described by Sambrook et al (1989). Poly(A)+ RNA was obtained by two rounds of extraction of total RNA using Dynabeads oligo(dT)25 (Dynal (UK) Ltd). cDNA was synthesised using a cDNA synthesis kit from Amersham (Amersham International PLC,).

Primers were designed from the published sequence of *Pyemotes tritici* toxin (Tox 34) cDNA (Tomalski and Miller, 1991). Primer A1 was designed to sit at the very 5' end of the coding sequence (5'1–29 3') and primer A2 approximately 90 basepairs downstream of A1 (5'121–150 3'). Primer D was designed to sit at the opposite end of the published Tox 34 cDNA sequence and to be complementary to the published cDNA (5'879-849 3'). The numbers shown above in brackets refer to the sequence as presented in FIG. 6.

PCR was carried out with A1 and D (denaturation, 1.1 minutes at 94° C.),; annealing, 1 minute at 60° C.; polymerisation, 4 minutes at 72° C.;) or A2 and D for 25 cycles. After 25 cycles fresh Taq polymerase was added and a further 25 cycles carried out. Amplicons were ligated directly in between the Bgl II and Eco RI sites of the commercial vector pVL1392 (Invitrogen Corp., San Diego, Calif.) to generate the transfer vector pVL1392-Tox 34#4. The Pyemotes derived insert in pVL1392-Tox 34#4 was then sequenced and this sequence, along with the deduced amino acid sequence, is presented in FIG. 6. As can be seen, the sequence of the Pyemotes derived insert in pVL1392-Tox 34#4 is clearly different from that originally published by Tomalski and Miller (1991). Most surprising is the distribution of the observed differences in the presumptive protein. Although the amino and carboxy terminii of the proteins are in good agreement there is a 17% difference in the protein in the central 100 amino acids (amounting to a difference of approximately 5.8% over the whole protein).

Example 4
Recombinant HaNPV expressing a toxin encoding sequence from *Pyemotes tritici*

For generation of recombinant HaSNPVs containing a *Pyemotes tritici* toxin sequence, the coding sequence of the toxin was excised from pVL1392-Tox 34#4 by digestion with Bgl II and Bam HI and ligated into the Bam HI site of the transfer vector pA44NS31 (pA44NS31-Tox 34#4). Co-transfections were carried out with pA44NS31-Tox 34#4 and DNA from the A44EB1 recombinant, A44NS31-Gus.

Transfection supernatants were subjected to serial and limiting end-point dilution and putative recombinants were assessed for positive cytopathic effect (C.P.E.) and their inability to express β-glucuronidase that catalyzes X-Gluc (5-Bromo-4-chloro-3-indolyl-b-D-glucuronic acid). Recombinants were further screened using PCR primers designed from the A44EB1 sequence. The first of these primers was located upstream of the polyhedrin promoter (A44RV; 5'-TATGAAGATATCTGTCGT-3') (SEQ ID NO:12) and the second (A44ASLR; 5'-GTAGGGCTGTAACTGTAACG-3') (SEQ ID NO:16) within the coding sequence of the mutated polyhedrin gene.

In the first round of screening four clones were picked that produced a positive CPE but laced β-glucuronidase activity. Of these four clones only one was found, by PCR, to contain the complete Tox 34#4 insert. This clone (A44NS31-Tox 34#4-2A10) was amplified to produce sufficient quantities of POVs for bioassays and preliminary bioassays carried out.

In the first experiment conducted, mid-second instar *H. armigera* were bioassayed as described above, with A44NS31-Gus POVs included as a control. For A44NS31-Tox 34#4-2A10 an LC$_{50}$ of 0.00955 (b=1.089+/−0.144) was obtained with LT$_{50}$s of 4.7 and 5.5 days derived at doses of 20.94 and 4.19 LC$_{50}$s/well respectively. For the A44NS31-Gus control and LC$_{50}$ of 0.02638 (b=1.023+/−0.199) was obtained with and LT$_{50}$ of 6.1 days derived at a dose of 7.58 LC$_{50}$s/well.

In the second experiment, late-first instar *H. punctigera* were bioassayed (with different preparations of A44NS31-

Gus and A44NS31-Tox 34#4-2A10). For A44NS31-Tox 34#4-2A10, an $LC_{50}$ of 0.00280 was obtained (b=1.629+/−0.273) with derived $LT_{50}$s of 3.4 and 4.3 days at doses of 14.29 and 2.86 $LC_{50}$s/well respectively. For A44NS31-Gus an $LC_{50}$ of 0.00402 was obtained (b=1.616+/−0.296) with $LT_{50}$s of 4.1 and 4.8 days at doses of 9.95 and 1.99 $LC_{50}$s/well respectively.

Both of the above experiments indicated that the Pyemotes derived Tox 34#4 insert was capable of improving the speed of action of a recombinant HaNPV above and beyond that which can be obtained from the insertion of b-galactosidase/b-glucoronidase into the wild-type virus. However, in the course of the above experiments, routine PCR screening of the A44-NS31-Tox 34#4-2A10 clone revealed that it was contaminated with A44NS31-Gus. Notwithstanding this contamination, it is noteworthy that the mixture of A44NS31-Tox 34#4-2A10 and A44NS31-Gus gave an improvement in $LT_{50}$ over that obtained with A44NS31-Gus alone.

For the above reason an additional round of limiting end-point purification were applied to A44NS31-Tox 34#4-2A10 to purify it way from the contaminating A44NS31-Gus. Two clones were selected from the cloning process for further analysis (A44NS31-Tox 34#4-2A10-D8 and A44NS31-Tox 34#4-2A10-D10).

In the first experiment conducted with these clones, bioassays were carried out against mid-first instar *H. punctigera;* using A44NS31-Gus as a control. The A44NS31-Gus control gas an $LC_{50}$ of 0.0221 (b=1.228+/−0.485). A44NS31-Tox 34#4-2A10-D8 and A44NS31-Tox 34#4-2A10-D10 gave corresponding low mortality and at dilutions of 0.1 gave only 43% and 8% mortality respectively. However, when *H. armigera* (more susceptible to HaSNPV than *H. punctigera*—see Table 3) were treated with 1 in 10 dilutions of A44NS31-Gus, A44NS31-Tox 34#4-2A10-D8 and A44NS31-Tox 34#4-2A10-D10, $LT_{50}$s of 4.3, 3.9 and 4.0 days respectively were obtained.

Further preparations of both A44NS31-Tox 34#4-2A10-D8 and A44NS31-Tox#4-2A10-D10 were tested against mid-first instar *H. punctigera*, along with an A44NS31-Gus control. The A44NS31-Gus control gave an $LC_{50}$ of 0.00185 (b=1.540+/−0.377), with derived $LT_{50}$s of 3.7 days and 4.9 days at 21.6 and 4.3 $LC_{50}$s/well respectively. For A44NS31-Tox 34#4-2A10-D8 an $LC_{50}$ of 0.1446 was obtained (b=1.681+/−0.427) and an $LT_{50}$ of 3.1 days derived at a dose of 1.4 LC50s/well. A44NS31-Tox 34#4-2A10-D10 gave an $LC_{50}$ of 0.1451 (b=2.070+/−0.477) with a derived $LT_{50}$ of 3.8 days at 1.4 $LC_{50}$s/well. Clearly both A44NS31-Tox 34#4-2A10-D8 and A44NS31-Tox 34#4-2A10-D10 give reductions in time-to-kill compared with the A44NS31-Gus control.

In a final experiment, 80–100 mg, *H. punctigera* larvae were injected with cell culture supernatants of A44NS31-Gus, A44NS31-Tox, 34#4-2A10-D8 and A44NS31-Tox 34#4-2A10-D10 containing $3.2 \times 10^5$, $4.2 \times 10^5$ and $3.2 \times 10^5$ $TCID_{50}$'s/ml respectively. Groups of twenty larvae each received 2 microliters of the relevant supernatant, injected into the haemocoel with a Small-bore glass capillary needle. Larvae were monitored every day for paralysis and/or viral death. The following results (Table 6) were obtained (Cumulative percentage mortality/paralysis are shown in each cell):

TABLE 6

| Virus | DAYS AFTER INJECTION | | | | | | | |
|---|---|---|---|---|---|---|---|---|
| | 3 | 4 | 5 | 6 | 7 | 8 | 9 | 10 |
| Saline | 0 | 0 | 0 | 0 | 0 | 0 | 0 | 0 |
| A44NS31-Gus | 0 | 0 | 11 | 35 | 60 | 60 | 60 | 90 |
| Tox 34-2A10-D8 | 0 | 33 | 52 | 85 | 90 | 90 | 90 | 90 |
| Tox 34-2A10-D10 | 0 | 50 | 77 | 83 | 88 | 88 | 88 | 88 |

From the above data $LT_{50}$s of 4.6, 4.0 and 6.6 days were obtained for A44NS31-Tox 34#4-2A10-D8, A44NS31-Tox 34#4-2A10-D10 and A44NS31-Gus respectively. Therefore, for the most active of the two Tox 34#4 containing recombinants i.e. A44NS31-Tox 34#4-2A10-D10 a reduction of 39% in $LT_{50}$ is observed relative to the $LT_{50}$ for the A44NS31-Gus recombinant.

Example 5

Generation of a Recombinant HaSNPV that Produces the Occluded Form of the Virus

Figure 9:
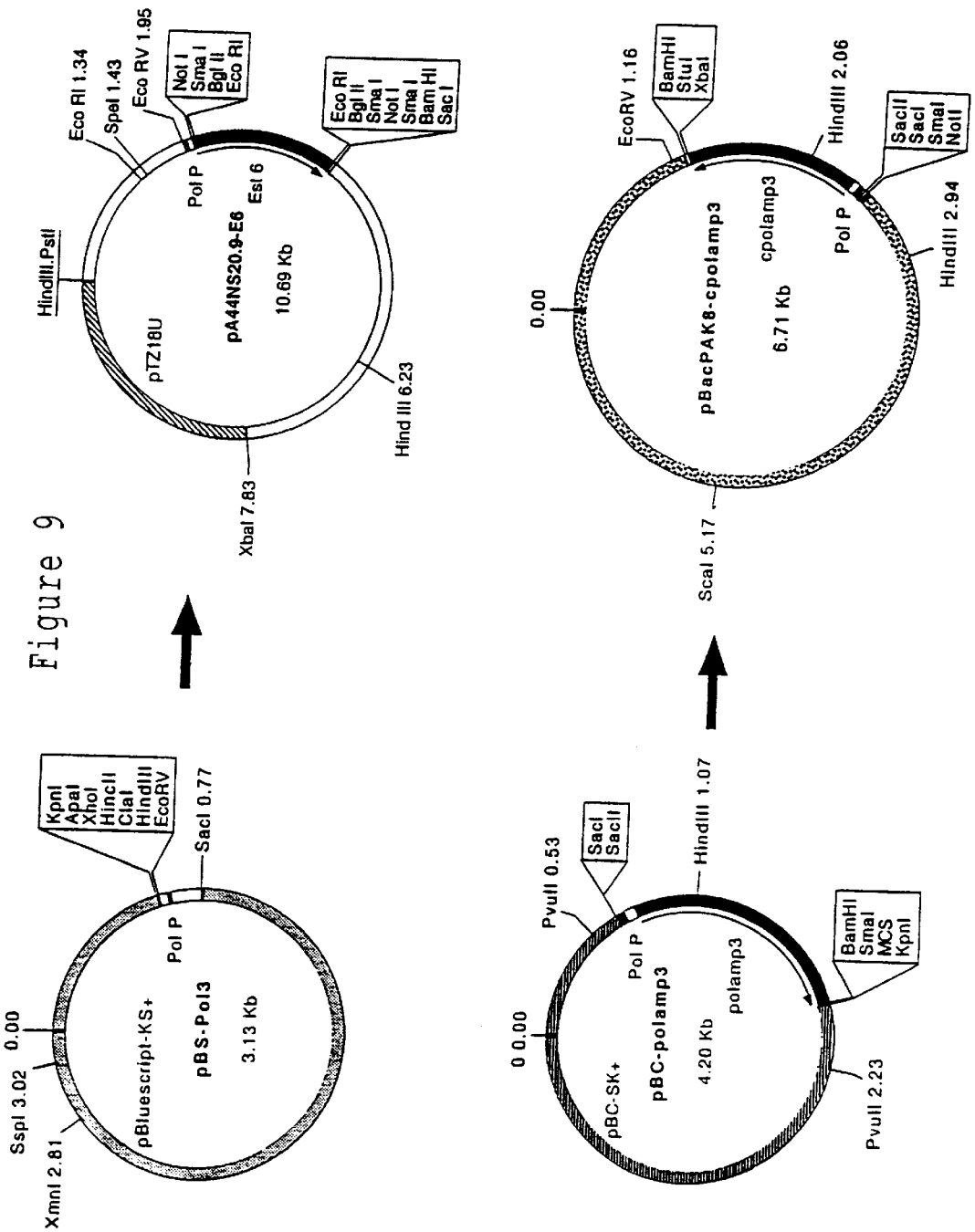
FIG. 9 details intermediates vectors used in the construction of HaNPV transfer vectors.

For generation of a recombinant virus capable of producing the virus in the occluded (pol$^+$) form, two separate approaches were tested. In the first approach, a copy of the polyhedrin promoter region was excised from the transfer vector pA44NS31 (FIG. 5) by digestion with Eco RV and Sac I. This fragment was ligated into the plasmid pBSKS+ (Stratagene, Palo Alto, Calif.), that had been digested with Eco RV and Sac I to generate the intermediate, shuttle vector pBS-Pol3 (FIG. 9). The fragment containing the promoter was then removed from pBS-Pol3 by digestion with Eco RV and Sma I and ligated into the transfer vector pA44NG1 that had previously been digested with Eco RV and treated with alkaline phosphate (Boehringer Mannheim, Mannheim, Germany).

pA44NG1 was generated from pA44ASL in the following way (FIG. 7A). pA44ASL was digested to completion with Xba I and then partially digested with Spe I. The products resulting from this partial digestion were separated by electrophoresis in a 0.8% agarose gel and the 8.48 Kb fragment isolated and purified by electroelution as described in Sambrook et al. (1989). The isolated 8.48 Kbp fragment was re-ligated to generate pA44NG1.

Figure 7A:
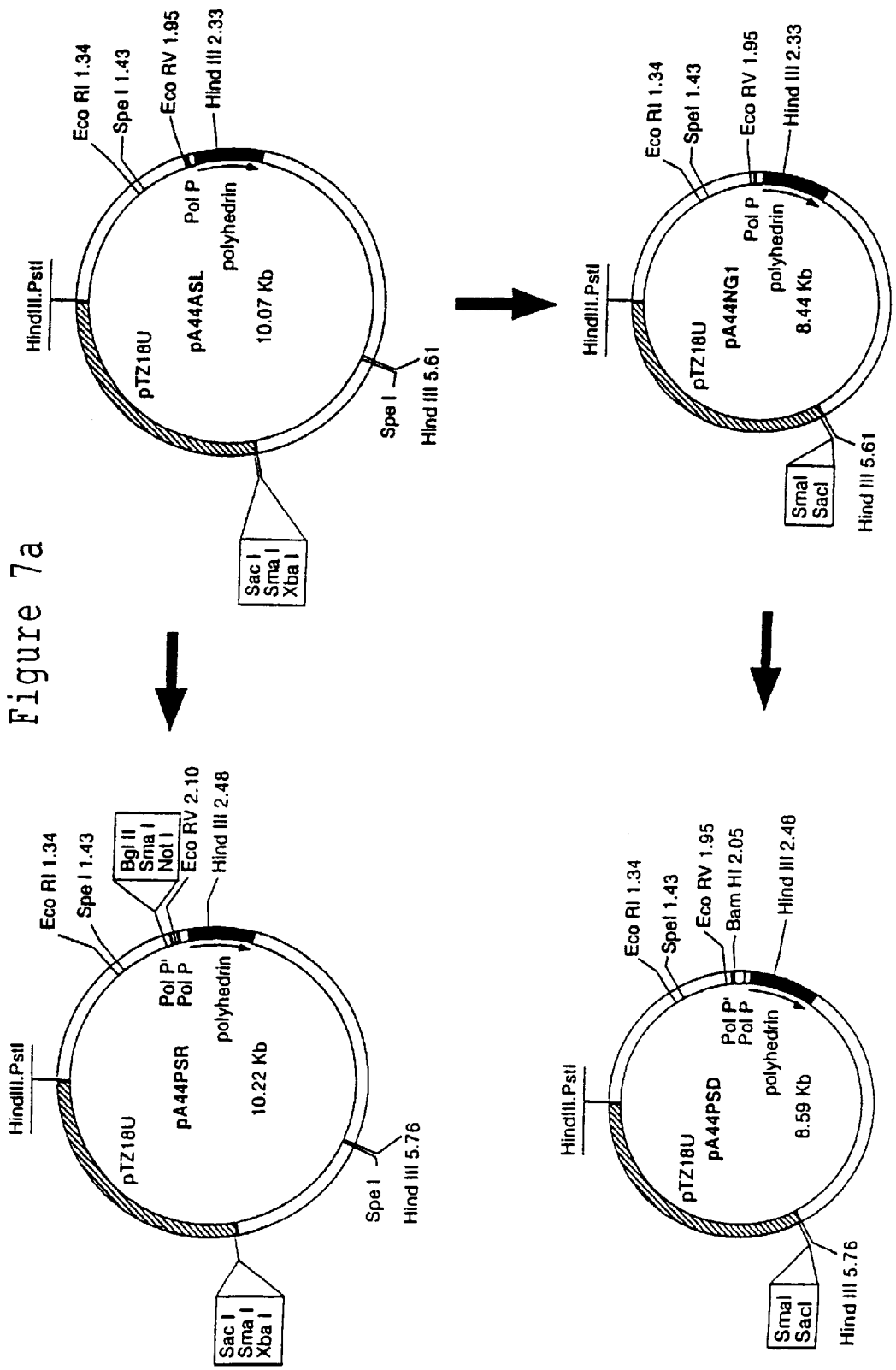
FIG. 7 (A) outlines the construction of one pol+ transfer vectors, (B) outlines the construction of intermediate vectors used in the construction of those vectors outlined in FIG. 7(A).
Figure 7B:
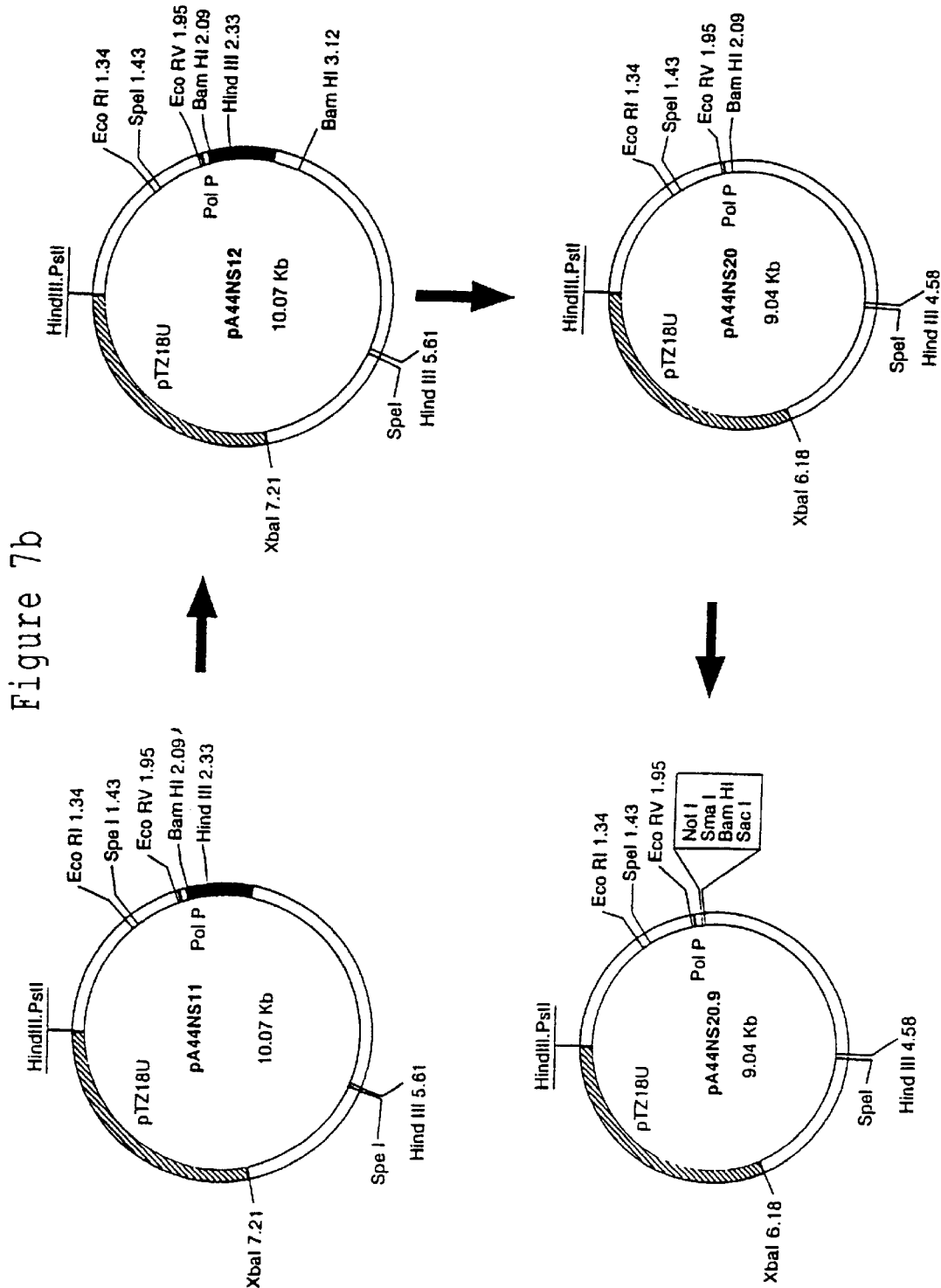
Figure 8:
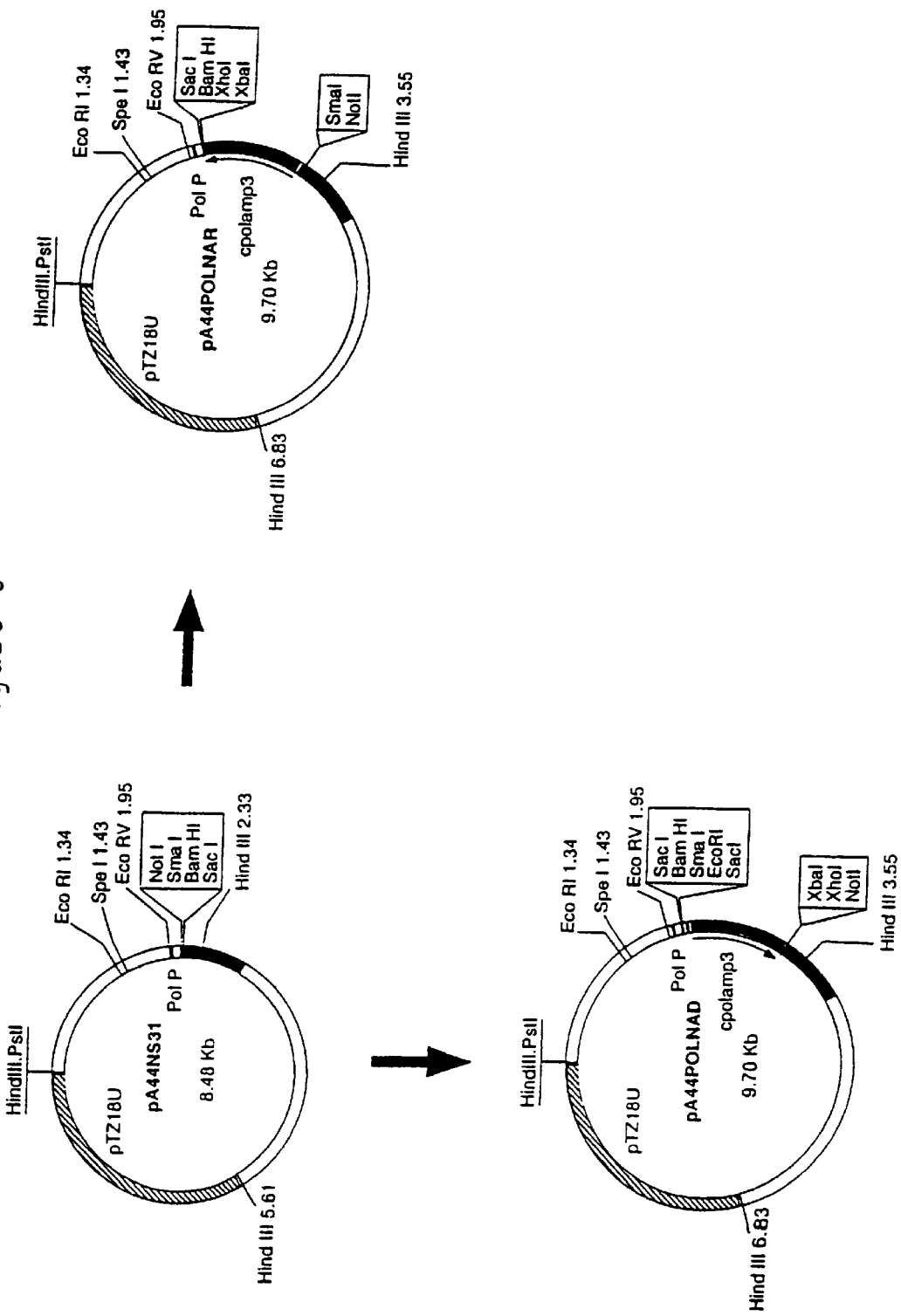
FIG. 8 outlines the construction of some of the pol+ transfer vectors.

The transfer vector containing the native polyhedrin promoter and coding sequence and a second copy of the polyhedrin promoter, inserted in the same transcriptional orientation upstream of the native promoter/coding sequence, is referred to as pA44PSD (FIG. 7A). Using the above method we were unable to generate a transfer vector in which the second copy of the polyhedrin promoter was inserted in the opposite transcriptional orientation to the in situ copy of the promoter.

The b-galactosidase coding sequence was removed from the vector pGH101 (Herman et al, 1986) by digestion with Bam HI and inserted into the pA44PSD transfer vector that had been digested with Bam HI. This transfer vector, referred to as pA44PSD-Gal was then co-transfected along with viral DNA from the recombinant A44NS31-Gus into *H. zea* cells.

Transfection supernatants harvested 10–14 days post-transfection were subjected to serial and limiting end-point dilution to identify putative recombinants. We isolated several recombinants that were phenotypically pol$^+$, above to express β-galactosidase but unable to express β-glucoronidase. These pol$^+$ viruses were subsequently subjected to bioassay along with other cell culture and in vivo derived viruses to ascertain whether they retained biological activity. The results of these bioassays are shown in Table 7.

TABLE 7

Provides the results of a bioassay against *H. armigera*of the pol+ recombinant A44-PSD-GAL#1 compared with other A44EB1 viruses derived from cell culture.

| Virus[5] | [1]$LC_{50}$ | [2]Lower Limit | [3]Upper Limit | (4)b(+/−S.E) |
|---|---|---|---|---|
| A44EB1 wt | 0.160 | 0.089 | 0.324 | 1.729(0.205) |
| A44EB1 Cells | 0.182 | 0.121 | 0.255 | 1.776(0.202) |
| A44-PSD-GAL#1 | 1.100 | 0.505 | 1.843 | 1.707(0.158) |

[1]$LC_{50}$'s are expressed PIBs/mm2. Estimates of $LC_{50}$ were obtained by probit analysis using the POLO program and are derived from the pooled data from three at least separate replicates in which four virus concentration between 10.0–0.001 PIBs/mm2 were used.
(2)Lower 95% fiducial limit of $LC_{50}$ estimate
(3)Upper 95% fiducial limit of $LC_{50}$ estimate
(4)Slope of probit mortality line
(5)Viruses used; A44EB1 wt; standard A44EB1 propagated in *H. armigera* larvae.A44EB1 Cells = A44EB1 propagated in *H. zea* cells (Passage 3); A44-PSD-GAL#1 = pol+ recombinant propagated in *H. zea* cells;

To generate a transfer vector in which the second copy of the polyhedrin promoter was inserted in the opposite transcriptional orientation to the in situ copy of the promoter the following procedure was adopted in which a number of intermediate vectors were constructed. The first of these, pFE6 contains the esterase-6 coding sequence flanked by linkers containing the Eco RI, Bgl II, Sma I and Not I restriction sites. To generate this vector the esterase-6 coding sequence was removed from pE6 by digestion with Eco RI. Linkers were then generated by annealing the primers:

ECONOTA AATTCAGATCTCCCGGGC (SEQ ID NO:17)

ECONOTB GGCCGCCCGGGAGATCTG (SEQ ID NO:18)

The resulting dsDNA linkers from the annealing reaction were then ligated to the isolated DNA fragment containing the esterase-6 cDNA, digested, with Not I and then inserted into the vector pBluescript SK- that had been digested with Not I. The resultant clone that contained the esterase-6 cDNA with Eco RI, Bgl II, Sma I and Not I sites on either end is referred to as pFE6. The esterase-6 insert was then removed from pFE6 by digestion with Not I and inserted into the transfer vector pA44NS20.9 to generate the transfer vector pA44NS20.9-E6.

pA44NS20.9 was generated in the following way. A primer was designed from the known sequence of pA44ASL, downstream of the polyhedrin coding sequence in the region of the putative polyadenylation signal (FIG. 2). This primer (5'-GTTTGTGGGATCCGAAAGC-3') (SEQ ID NO:19) was used in an in vitro mutagenesis reaction to introduce a second Bam HI site into pA44NS11. The resulting vector (pA44NS12) was digested with Bam HI and then religated to generate the vector pA44NS20. A multiple cloning site was then introduced into pA44NS20 in the same way as that introduced into pA44NS1 (FIG. 5; see also Example 2). The transfer vector containing the multiple cloning site in the orientation with the Not I site proximal to the polyhedrin promoter and the Sac I site distal to the promoter is referred to as pA44NS20.9 (FIG. 9).

The polyhedrin promoter and E6 coding sequence were then removed as a single fragment from pA44NS20.9-E6 by complete digestion with Eco RV and partial digestion with Sma I. The resultant 1.75 kbp blunt-ended fragment was then ligated into pA44ASL that had been digested with Eco RV, the esterase coding sequence removed by digestion with Bgl II and the transfer vector re-ligated to generate pA44PSR. (FIG. 7A).

The b-galactosidase coding sequence was inserted into pA44PSR by digestion of pGH101 with Bam HI, isolation of the DNA fragment and then ligated into pA44PSR that had been digested with Bgl II to generate the transfer vector pA44PSR-Gal. This transfer vector was then co-transfected along with viral DNA from the recombinant A44NS31-Gus into *H zea* cells. Transfection supernatants harvested 10–14 days post-transfection were subjected to serial and limiting end-point dilution to identify putative recombinants. However, in three separate transfection experiments no recombinants were isolated that were phenotypically pol+ and also able to express β-galactosidase.

In a separate experiment, pA44NS20.9-E6 was co-transfected along with viral DNA from A44EB1 into *H zea* cells. Transfection supernatants harvested 10–14 days post-transfection were subjected to serial and limiting end-point dilution to identify putative recombinants. However, in four separate transfection experiments no recombinants were isolated that were able to express esterase-6 (as determined by Titan II cellulose acetate electrophoresis—Example 2) and were phenotypically pol−.

The above results are useful in helping to delimit the sequences flanking the polyhedrin gene and promoter that have essential functions and therefore cannot be disrupted in the generation of recombinants. With pA44PSR-Gal, heterologous nucleotide sequences are inserted into the 3' end of the coding sequence of the ORF upstream of the polyhedrin promoter and gene (see FIG. 3). Failure to isolate recombinants from this construct strongly suggests that this gene has an essential function and that it's transcription cannot be disrupted by the insertion of heterologous nucleotide sequences. With pA44NS20.9-E6, the vector pA44NS20.9 was constructed by removal of all polyhedrin coding sequence and 3' untranslated sequence, up to and including the putative polyadenylation signal. In this case, the removal of this DNA disrupts the 3' end of the ORF downstream of polyhedrin. Again this suggests that disruption of this coding sequence is deleterious to the generation of recombinant viruses (i.e. the product of this ORF has an essential function).

It would therefore appear, that unlike other baculoviruses (e.g. *Autographa californica* MNPV), the DNA sequences flanking both the 5' and 3' sequences of the polyhedrin promoter and coding region are necessary for viral replication. These sequences cannot be disrupted during the construction of transfer vectors if viable recombinant viruses are to be generated.

In the second approach to generating a pol+ recombinant HaSNPVs, the polyhedrin promoter and coding region were copied from the transfer vector pA44ASL by PCR using the primers A44RV and A443'Bam (5'GTTTCGGATCCACAAACA-3')(SEQ ID NO:20) under the following conditions:

5 minutes at 95° C. 35 seconds at 95° C., 1 minutes at 50° C., 1.5 minutes at 72° C. (25 cycles).

The amplified fragments of DNA were then digested with Eco RV and BamHI, and ligated into pBCSK−. The pBCSK− vector had been digested with Not I and then the over-hanging ends filled-in with the Klenow fragment of DNA polymerase I to generate a blunt end. After the end-filling reaction, the vector was digested with Bam HI prior to ligation with the amplified DNA fragment. This clone is referred to as pBC-polamp3.

A fragment containing the polyhedrin promoter, coding sequence and putative polyadenylation signal was removed from pBS-polamp3 by digestion with Bam HI and Sac I and ligated into the pBacPAK8 transfer vector (Clontech Laboratories, Palo Alto, Calif.) that had been digested with Bgl II and Sac I to generate the shuttle vector pBacPAK8-cpolamp3. The polyhedrin promoter, coding sequence and putative polyadenylation signal was then removed from this shuttle vector by digestion with Stu I and Sma I and ligated into the Sma I site of the transfer vector pA44NS31. The transfer vector in which the inserted polyhedrin promoter-coding sequence is in the same orientation as the in situ promoter of the parental vector, pA44EB1, is termed pA44POLNAD and that in which it is in the opposite orientation is termed pA44POLNAR.

pA44POLNAD and pA44POLNAR were used in co-transfection experiments with viral DNA from the recombinant pNS31-Gus. Transfection supernatants were harvested 10–13 days post-transfection and subjected to serial and limiting end-point dilution to isolate putative recombinants. In experiments with pA44POLNAD recombinants were isolated that were phenotypically pol$^+$ and unable to express b-glucoronidase. In contrast we were unable to isolate any recombinants that were phenotypically pol$^+$ and unable to express b-glucoronidase from transfections carried out with pA44POLNAR.

REFERENCES

Belyaev, A. S. and Roy, P. (1993) Development of baculovirus triple and quadruple expression vectors: co-expression of three and four bluetongue virus proteins and the synthesis of bluetongue virus-like particles in insect cells. Nucl. Acids Res. 21; 1219–1223.

Birnboim, H. C. and Doly, J. (1979). A rapid extraction procedure for screening recombinant plasmid DNA. Nucleic Acids Res. 7, 1513–1523.

Carbonell L. F. Hodge, M. R. Tomalski, M. D. and Miller, L. K. (1988) Synthesis of a gene coding for an insect-specific scorpion neurotoxin and attempts to express it using baculovirus vectors. Gene 73: 409–418

Emery, V. C. and Bishop D. H. L. (1987) The development of multiple expression vectors for the high level synthesis of eukaryotic proteins: expression of LCMV-N and AcNPV polyhedrin protein by a recombinant baculovirus. Protein Engineering 1; 359–366.

Hammock, B. D., Bonning, B. C., Possee, R. D., Hanzlik, T. N. and Maeda, S. (1990) Expression and effects of the juvenile hormone esterase in a baculovirus vector. Nature 344: 456–461.

Herman, G. F., O'Brien, W. F. and Beaudet, A. L. (1986) An *E. coli* b-galactosidase cassette suitable for study of eukaryotic expression. Nucl. Acids Res. 14, 7130.

Horowitz and Barnes (1983) A simple, inexpensive and precise microcell for the exchange dialysis and equilibrium dialysis of Small samples. Analytical Biochemistry 128, 478–480

Ignoffo, C. M., Hostetter, D. L. and Smith, D. B. (1976) Gustatory stimulant, sunlight protectant, evaporation retardant; three characteristics of a microbial insecticide adjuvant. J. Econ. Entomol. 69: 207–210.

Ignoffo, C. M., McIntosh, A. H. and Garcia, C. (1983) Susceptibility of larvae of *H. zea, H. virescens* and *H. armigera* (Lep: Noctuidae) to three baculoviruses. Entomophaga 28: 1–8.

Jefferson, R. A. (1987) GUS gene fusion systems user's manual. Version 1.1, Cambrige, U.K.

Kang, Y. C. (1990) Improved baculovirus expression system capable of producing foreign gene proteins at high levels. PCT Application. International Publication number WO 90/10078

Knell, J. D. and Summers, M. D. (1984) A physical map for the *Heliothis zea* SNPV genome. J. Gen Virol 65, 445–450.

McIntosh, A. H., Maramorosch, K. and Rechtoris, C. (1973) Adaptation of an insect cell line (*Agallia constricta*) in a mammalian cell culture medium. In Vitro 8:375–378.

Maeda, S. (1989) Expression of foreign genes in insects using baculovirus vectors. Ann. Rev. Entomol. 34;351–372.

Miller, L. K. (1990) Improved baculovirus expression vectors. PCT Application. International Publication number WO 90/14428

Miller, L. K. (1991) Insect virus vector with broadened host range. U.S. Pat. No. 5,004,687.

Nei, M. and Miller, J. C. (1990) A simple method for estimating average nucleotide substitutions within and between populations from restriction data. Genetics 125: 873–879.

Morrison (1979). Transformation and preservation of competent bacterial cells by freezing. Methods in Enzymology 68, 326–331.

Oakeshott, J. G., Collet, C., Phillis, R. Neilsen, K. M., Russell, R. J., Chambers, G. K., Ross, V. and Richmond, R. C. (1987) Molecular cloning and characterisation of esterase 6' a serine hydrolase from Drosophila. Proc. Natl. Acad. Sci. USA 84: 3359–3363.

Shorey, H. H. and Hale, R. L. (1965). Mass-rearing of the larvae of nine noctuid species on a simple artificial medium J. Econ. Entomol. 38, 522–524.

Russell, R. M., Robertson, J. L. and Savin, N. E. (1977) POLO: a new computer program for probit analysis. Bull. Entomolo. Soc. Amer. 23, 209–213.

Sambrook, J., Fritsch, E. F. and Maniatis, T. (1989) Molecular cloning: a laboratory manual. 2nd ed. Cold Spring Harbor Laboratory Press, Cold Spring Harbor.

Stewart L. M. D., Hirst M., Lopez Ferber M., Merryweather A. T., Cayley P. J., Possee R. D. (1991) Construction of an improved baculovirus insecticide containing an insect-specific toxin gene. Nature 352:85–88.

Smith, I. R. L. and Crook, N. E. (1988). In vivo isolation of baculovirus genotypes. Virology 166, 240–244.

Takehara, K., Ireland, D. and Bishop, D. H. L. (1988) Co-expression of hepatitis B surface and core antigens using baculovirus multiple expression vectors. J. Gen. Virol. 69, 2763–2777.

Tomalski M. D. and Miller L. K. (1991) Insect paralysis by baculovirus-mediated expression of a mite neurotoxin gene. Nature 352:82–85

Vail, P. V., Jay, D. L., Stewart, F. D., Martinez, A. J. and Dulmage, H. T. (1978) Comparative susceptibility of *Heliothis virescens* and *H. zea* to the nuclear polyhedrosis virus isolated from *Autographa californica*. J. Econ. Entomol. 71, 293–296.

Wood, H. A., Munckenbeck Totter, K., Davis, T. R. and Hughes, P. R. (1993) Per os infectivity of preoccluded virions from polyhedrin-minus recombinant baculoviruses. J. Invertebr. Pathol. 62, 64–67.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A recombinant HaSNPV characterized in that heterologous DNA is located in one or more non-essential regions of the viral genome, in a manner to permit the expression of the heterologous DNA, and wherein said recombinant HaSNPV produces functional polyhedrin.

2. A recombinant HaSNPV according to claim 1 prepared from an HaSNPV isolate having a Bam HI restriction fragment size profile as shown in Table 1.

3. A recombinant HaSNPV according to claim 1 prepared from an HaSNPV isolate with a polyhedrin gene comprising a nucleotide sequence as shown in SEQ ID NOS: 8, 9, 10 or 11.

4. A recombinant HaSNPV according to claim 3, wherein said HaSNPV isolate has a Bam HI restriction fragment size profile as shown in Table 1.

5. A recombinant HaSNPV according to claim 1 prepared from an HaSNPV isolate comprising a nucleotide sequence encoding the amino acid sequence of SEQ ID NO:21.

6. A recombinant HaSNPV according to claim 1, wherein heterologous DNA is located within the region encoding chitinase or the ecdysteroid UDP-glucosyl transferase.

7. A recombinant HaSNPV according to claim 1, wherein heterologous DNA is located within a region about 150 nucleotides upstream of the polyhedrin start site in a manner which is not disruptive to the expression of an adjacent 5' ORF.

8. A recombinant HaSNPV according to claim 1, wherein the heterologous DNA comprises gene(s) encoding one or more substances that are deleterious to insects.

9. A recombinant HaSNPV according to claim 8, wherein the gene(s) encodes a substance selected from the group consisting of *Pyemotes tritici* tox 34#-like toxins, insect neurohormones, juvenile hormone esterase and juvenile hormone binding proteins.

10. A recombinant HaSNPV according to claim 1, wherein the heterologous DNA is expressed by a polyhedrin promoter of HaSNPV.

11. A method for controlling the proliferation of pest insects, comprising applying to an infested area a recombinant HaSNPV according to claim 1, optionally in admixture with an acceptable agricultural carrier.

12. A method for producing a desired protein, polypeptide or peptide comprising infecting susceptible host cells with a recombinant HaSNPV according to claim 1.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 879 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 4..876

(xi) SEQUENCE DESCRIPTION: SEQ ID NO:1:

```
TTA ATG AAA ATT TGT ACA TTT TTT ATT CCT TTA TTC AAA ATG AAC TTG        48
    Met Lys Ile Cys Thr Phe Phe Ile Pro Leu Phe Lys Met Asn Leu
    1               5                  10                  15

TTT TTT TTA TTT ATT ATT CCA ACA ATT TTA GCA GTT AAA CCT TTT AGG        96
Phe Phe Leu Phe Ile Ile Pro Thr Ile Leu Ala Val Lys Pro Phe Arg
                20                  25                  30

TCT TTT AAT AAT ATT TCC TTA ATT GAT AAT GGC AAT GTC GAA TCT GTA       144
Ser Phe Asn Asn Ile Ser Leu Ile Asp Asn Gly Asn Val Glu Ser Val
            35                  40                  45

AGA GCA GTA GTT ATT GAT TAT TGT GAT ATT AGA CAT CCA AAT AAT TTA       192
Arg Ala Val Val Ile Asp Tyr Cys Asp Ile Arg His Pro Asn Asn Leu
        50                  55                  60

TGT AAA AAA CAT TTT GAA ATC GAT TCA TAT TGG AAT GAT GAT ACG GAT       240
Cys Lys Lys His Phe Glu Ile Asp Ser Tyr Trp Asn Asp Asp Thr Asp
    65                  70                  75

TGT TTT ACA AAT ATT GGA TGC AAA GTA TAT GGA GGA TTT GAT ATT ATT       288
Cys Phe Thr Asn Ile Gly Cys Lys Val Tyr Gly Gly Phe Asp Ile Ile
80                  85                  90                  95

GGT GGT CAT ACC CCT AAA GTT GGA ACT GTA TGT AGA CTT AAA AAA GGA       336
Gly Gly His Thr Pro Lys Val Gly Thr Val Cys Arg Leu Lys Lys Gly
                100                 105                 110

GAA AAT AAA TTT GGA TAT TGT AAT TCA AAG GGA AAT TGC GTT GAA AGA       384
Glu Asn Lys Phe Gly Tyr Cys Asn Ser Lys Gly Asn Cys Val Glu Arg
            115                 120                 125

GAT TTT AAA GAA AGT TTT GGA ATA TCT ATA AAA ATA AAA GGA ATT TCT       432
Asp Phe Lys Glu Ser Phe Gly Ile Ser Ile Lys Ile Lys Gly Ile Ser
        130                 135                 140

AAT AAA GGA GAT GAT GAA CCA GCA TGT CCA CAA TAT AAA AAT ACT TGG       480
Asn Lys Gly Asp Asp Glu Pro Ala Cys Pro Gln Tyr Lys Asn Thr Trp
    145                 150                 155

ATT AAT TAT GGG AAA TGT AAT GAA CCT TAT TAT TGT GGA ACA AAT CAT       528
Ile Asn Tyr Gly Lys Cys Asn Glu Pro Tyr Tyr Cys Gly Thr Asn His
160                 165                 170                 175

GGA TTA TTT TAT GCA AAC AAA AGA AAA CTC GAT TAC TTT CCC ACA GAC       576
Gly Leu Phe Tyr Ala Asn Lys Arg Lys Leu Asp Tyr Phe Pro Thr Asp
                180                 185                 190

GGT GAA AAA TGT AAT TCA AAT AAT ATA CCA TAT GCT GTT TGT TAT TTA       624
Gly Glu Lys Cys Asn Ser Asn Asn Ile Pro Tyr Ala Val Cys Tyr Leu
            195                 200                 205

GGA AGA TGT CAT ACA ACA GGT GGT TTT TTT AGT GAA TTT GGA ACT ATT       672
Gly Arg Cys His Thr Thr Gly Gly Phe Phe Ser Glu Phe Gly Thr Ile
        210                 215                 220
```

```
GTT AAA AAT GTC GAA ATC GTA ACT TTA TCA GAT GGA AAG AAC AGT TCT      720
Val Lys Asn Val Glu Ile Val Thr Leu Ser Asp Gly Lys Asn Ser Ser
    225                 230                 235

AGA AGA GGA AAA CAT AAA AAT TTA CCT ACT TCT AAA GTA TTT GAT AGT      768
Arg Arg Gly Lys His Lys Asn Leu Pro Thr Ser Lys Val Phe Asp Ser
240                 245                 250                 255

TAT AGT ATA TAT GAT ATT GAT CCT AAA AAT TGG AAA ATT GAA GAT GAT      816
Tyr Ser Ile Tyr Asp Ile Asp Pro Lys Asn Trp Lys Ile Glu Asp Asp
                260                 265                 270

GAT AAA GAT GTT ACT GTT CAT GAA AAT ACA TTA GAT CCA AAA AGT GAT      864
Asp Lys Asp Val Thr Val His Glu Asn Thr Leu Asp Pro Lys Ser Asp
            275                 280                 285

TCA AGA CTG TGT TAA                                                  879
Ser Arg Leu Cys
        290
```

(2) INFORMATION FOR SEQ ID NO:2:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Ile Cys Thr Phe Phe Ile Pro Leu Phe Lys Met Asn Leu Phe
1               5                   10                  15

Phe Leu Phe Ile Ile Pro Thr Ile Leu Ala Val Lys Pro Phe Arg Ser
            20                  25                  30

Phe Asn Asn Ile Ser Leu Ile Asp Asn Gly Asn Val Glu Ser Val Arg
        35                  40                  45

Ala Val Val Ile Asp Tyr Cys Asp Ile Arg His Pro Asn Asn Leu Cys
    50                  55                  60

Lys Lys His Phe Glu Ile Asp Ser Tyr Trp Asn Asp Thr Asp Cys
65                  70                  75                  80

Phe Thr Asn Ile Gly Cys Lys Val Tyr Gly Gly Phe Asp Ile Gly
                85                  90                  95

Gly His Thr Pro Lys Val Gly Thr Val Cys Arg Leu Lys Lys Gly Glu
                100                 105                 110

Asn Lys Phe Gly Tyr Cys Asn Ser Lys Gly Asn Cys Val Glu Arg Asp
            115                 120                 125

Phe Lys Glu Ser Phe Gly Ile Ser Ile Lys Ile Lys Gly Ile Ser Asn
        130                 135                 140

Lys Gly Asp Asp Glu Pro Ala Cys Pro Gln Tyr Lys Asn Thr Trp Ile
145                 150                 155                 160

Asn Tyr Gly Lys Cys Asn Glu Pro Tyr Tyr Cys Gly Thr Asn His Gly
                165                 170                 175

Leu Phe Tyr Ala Asn Lys Arg Lys Leu Asp Tyr Phe Pro Thr Asp Gly
            180                 185                 190

Glu Lys Cys Asn Ser Asn Asn Ile Pro Tyr Ala Val Cys Tyr Leu Gly
        195                 200                 205

Arg Cys His Thr Thr Gly Gly Phe Phe Ser Glu Phe Gly Thr Ile Val
    210                 215                 220

Lys Asn Val Glu Ile Val Thr Leu Ser Asp Gly Lys Asn Ser Ser Arg
225                 230                 235                 240

Arg Gly Lys His Lys Asn Leu Pro Thr Ser Lys Val Phe Asp Ser Tyr
```

```
                         245                 250                     255
Ser Ile Tyr Asp Ile Asp Pro Lys Asn Trp Lys Ile Glu Asp Asp
            260                 265                 270

Lys Asp Val Thr Val His Glu Asn Thr Leu Asp Pro Lys Ser Asp Ser
        275                 280                 285

Arg Leu Cys
    290

(2) INFORMATION FOR SEQ ID NO:3:

(i) SEQUENCE CHARACTERISTICS:
        (A) LENGTH: 879 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 4..876

(xi) SEQUENCE DESCRIPTION: SEQ ID NO:3:

TTA ATG AAA ATT TGT ACA TTT TTT ATT CCT TTA TTC AAA ATG AAC TTG        48
    Met Lys Ile Cys Thr Phe Phe Ile Pro Leu Phe Lys Met Asn Leu
            295                 300                 305

TTT TTT TTA TTT ATT ATT CCA ACA ATT TTA GCA GTT AAA CCT TTT AGG        96
Phe Phe Leu Phe Ile Ile Pro Thr Ile Leu Ala Val Lys Pro Phe Arg
            310                 315                 320

TCT TTT AAT AAT ATT TCC TTA ATT GAT AAT GGC AAT GTC GAA TCT GTA       144
Ser Phe Asn Asn Ile Ser Leu Ile Asp Asn Gly Asn Val Glu Ser Val
            325                 330                 335

AGA GCA GTA GTT ATT GAT TAT TGT GAT ATT AGA CAT CCA AAT AAT TTA       192
Arg Ala Val Val Ile Asp Tyr Cys Asp Ile Arg His Pro Asn Asn Leu
    340                 345                 350

TGT AAA AAA CAT TTT GAA ATC GAT TCA TAT TGG AAT GAT GAT ACG GAT       240
Cys Lys Lys His Phe Glu Ile Asp Ser Tyr Trp Asn Asp Asp Thr Asp
355                 360                 365                 370

TGT TTT ACA AAT ATT GGA TGC AAA GTA TAT GGA GGA TTT GAT ATT ATT       288
Cys Phe Thr Asn Ile Gly Cys Lys Val Tyr Gly Gly Phe Asp Ile Ile
                375                 380                 385

GGT GGT CAT ACC CCT AAA GTT GGA ACT GTA TGT AGA CAT AAA AAA GGA       336
Gly Gly His Thr Pro Lys Val Gly Thr Val Cys Arg His Lys Lys Gly
            390                 395                 400

GAA AAT AAA TTT GGA TAT TGT AAT TCA AAG GGA AAT TGC GTT GAA AGA       384
Glu Asn Lys Phe Gly Tyr Cys Asn Ser Lys Gly Asn Cys Val Glu Arg
            405                 410                 415

GAT TTT AAA GAA AGT TTT GGA ATA TCT ATA AAA ATA AAA ATA ATA ACT       432
Asp Phe Lys Glu Ser Phe Gly Ile Ser Ile Lys Ile Lys Ile Ile Thr
    420                 425                 430

GAT AAA GGA GAA AAT GAA CCA GCA TGT CCA ATT TAT GGA AAT ACC TGG       480
Asp Lys Gly Glu Asn Glu Pro Ala Cys Pro Ile Tyr Gly Asn Thr Trp
435                 440                 445                 450

ATT AAT TAT GGA AAA TGT AAT GAA CCT TAT CAT TGT GGA ACA GAT CAT       528
Ile Asn Tyr Gly Lys Cys Asn Glu Pro Tyr His Cys Gly Thr Asp His
                455                 460                 465

TGG TTA TTA TAT GCA AAC AAA AAA AAT CTT CAT TTC TTT CCT ACA GAT       576
Trp Leu Leu Tyr Ala Asn Lys Lys Asn Leu His Phe Phe Pro Thr Asp
            470                 475                 480

GGT GAA AAA TGT AAT TCA AAA AAT ATA CCA TAT GCT GTT TGT TAT TTA       624
Gly Glu Lys Cys Asn Ser Lys Asn Ile Pro Tyr Ala Val Cys Tyr Leu
            485                 490                 495
```

```
GGA AGA TGT CAT ACA ACA GGA GGT TTT TTT AGT GAA TTC GGA ACT ATT    672
Gly Arg Cys His Thr Thr Gly Gly Phe Phe Ser Glu Phe Gly Thr Ile
    500                 505                 510

GTT AAA AAT GTC GAA ATC GTA ACT TTA TCA GAT GGA AAG AAC AGT TCT    720
Val Lys Asn Val Glu Ile Val Thr Leu Ser Asp Gly Lys Asn Ser Ser
515                 520                 525                 530

AGA AGA GGA AAA CAT AAA AAT TTA CCT ACT TCT AAA GTA TTT GAT AGT    768
Arg Arg Gly Lys His Lys Asn Leu Pro Thr Ser Lys Val Phe Asp Ser
                535                 540                 545

TAT AGT ATA TAT GAT ATT GAT CCT AAA AAT TGG AAA ATT GAA GAT GAT    816
Tyr Ser Ile Tyr Asp Ile Asp Pro Lys Asn Trp Lys Ile Glu Asp Asp
            550                 555                 560

GAT AAA GAT GTT ACT GTT CAT GAA AAT ACA TTA GAT CCA AAA AGT GAT    864
Asp Lys Asp Val Thr Val His Glu Asn Thr Leu Asp Pro Lys Ser Asp
        565                 570                 575

TCA AGA CTG TGT TAA                                                879
Ser Arg Leu Cys
    580
```

(2) INFORMATION FOR SEQ ID NO:4:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Ile Cys Thr Phe Phe Ile Pro Leu Phe Lys Met Asn Leu Phe
  1               5                  10                  15

Phe Leu Phe Ile Ile Pro Thr Ile Leu Ala Val Lys Pro Phe Arg Ser
             20                  25                  30

Phe Asn Asn Ile Ser Leu Ile Asp Asn Gly Asn Val Glu Ser Val Arg
         35                  40                  45

Ala Val Val Ile Asp Tyr Cys Asp Ile Arg His Pro Asn Asn Leu Cys
     50                  55                  60

Lys Lys His Phe Glu Ile Asp Ser Tyr Trp Asn Asp Thr Asp Cys
 65                  70                  75                  80

Phe Thr Asn Ile Gly Cys Lys Val Tyr Gly Phe Asp Ile Gly
                 85                  90                  95

Gly His Thr Pro Lys Val Gly Thr Val Cys Arg His Lys Lys Gly Glu
                100                 105                 110

Asn Lys Phe Gly Tyr Cys Asn Ser Lys Gly Asn Cys Val Glu Arg Asp
            115                 120                 125

Phe Lys Glu Ser Phe Gly Ile Ser Ile Lys Ile Lys Ile Thr Asp
        130                 135                 140

Lys Gly Glu Asn Glu Pro Ala Cys Pro Ile Tyr Gly Asn Thr Trp Ile
145                 150                 155                 160

Asn Tyr Gly Lys Cys Asn Glu Pro Tyr His Cys Gly Thr Asp His Trp
                165                 170                 175

Leu Leu Tyr Ala Asn Lys Lys Asn Leu His Phe Phe Pro Thr Asp Gly
            180                 185                 190

Glu Lys Cys Asn Ser Lys Asn Ile Pro Tyr Ala Val Cys Tyr Leu Gly
        195                 200                 205

Arg Cys His Thr Thr Gly Gly Phe Phe Ser Glu Phe Gly Thr Ile Val
    210                 215                 220
```

```
Lys Asn Val Glu Ile Val Thr Leu Ser Asp Gly Lys Asn Ser Ser Arg
225                 230                 235                 240

Arg Gly Lys His Lys Asn Leu Pro Thr Ser Lys Val Phe Asp Ser Tyr
            245                 250                 255

Ser Ile Tyr Asp Ile Asp Pro Lys Asn Trp Lys Ile Glu Asp Asp Asp
            260                 265                 270

Lys Asp Val Thr Val His Glu Asn Thr Leu Asp Pro Lys Ser Asp Ser
            275                 280                 285

Arg Leu Cys
    290

(2) INFORMATION FOR SEQ ID NO:5:

(i) SEQUENCE CHARACTERISTICS:
        (A) LENGTH: 1168 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 157..894

(xi) SEQUENCE DESCRIPTION: SEQ ID NO:5:

ATCTTTTGCA AGAATATGAA GATTTCTGTC GTCGTGTTGA AAATTTGTAA TAAAACTAAA         60

TAAACCTTTA ATATAAATAT TAAACATACA CTTTTATTTC TAAAATAAGT ATTTTTTTCC        120

TATTGTTCAA GATTGTGAAA AATCAAATAT CCCATA ATG TAT ACT CGT TAC AGT         174
                                        Met Tyr Thr Arg Tyr Ser
                                                            295

TAC AGC CCT ACT TTG GGC AAA ACC TAT GTG TAC GAC AAC AAA TAC TTT         222
Tyr Ser Pro Thr Leu Gly Lys Thr Tyr Val Tyr Asp Asn Lys Tyr Phe
            300                 305                 310

AAG AAT TTA GGT GCT GTT ATT AAA AAT GCC AAA CGC AAG AAG CAT TTA         270
Lys Asn Leu Gly Ala Val Ile Lys Asn Ala Lys Arg Lys Lys His Leu
    315                 320                 325

GAG GAG CAC GAA CAT GAA GAA CGC AAC TTA GAT TCG CTC GAC AAA TAC         318
Glu Glu His Glu His Glu Glu Arg Asn Leu Asp Ser Leu Asp Lys Tyr
330                 335                 340                 345

TTG GTG GCG GAA GAT CCT TTT TTG GGA CCT GGC AAA AAT CAA AAA CTA         366
Leu Val Ala Glu Asp Pro Phe Leu Gly Pro Gly Lys Asn Gln Lys Leu
            350                 355                 360

ACT TTG TTT AAA GAG ATT CGC AGC GTT AAG CCC GAC ACA ATG AAG CTT         414
Thr Leu Phe Lys Glu Ile Arg Ser Val Lys Pro Asp Thr Met Lys Leu
            365                 370                 375

GTA GTT AAC TGG AGC GGT CGC GAA TTT CTT CGC GAA ACT TGG ACT CGT         462
Val Val Asn Trp Ser Gly Arg Glu Phe Leu Arg Glu Thr Trp Thr Arg
            380                 385                 390

TTC ATG GAA GAC AGT TTT CCC ATT GTA AAC GAC CAA GAA ATT ATG GAC         510
Phe Met Glu Asp Ser Phe Pro Ile Val Asn Asp Gln Glu Ile Met Asp
395                 400                 405

GTG TTT CTG TCT GTT AAT ATG CGA CCA ACC AAA CCG AAC CGT TGT TAC         558
Val Phe Leu Ser Val Asn Met Arg Pro Thr Lys Pro Asn Arg Cys Tyr
410                 415                 420                 425

CGA TTC TTA GCG CAA CAC GCT CTG CGT TGT GAT CCC GAC TAT ATT CCT         606
Arg Phe Leu Ala Gln His Ala Leu Arg Cys Asp Pro Asp Tyr Ile Pro
                430                 435                 440

CAC GAA GTC ATT CGT ATT GTA GAA CCT TCC TAT GTA GGC AGT AAC AAC         654
His Glu Val Ile Arg Ile Val Glu Pro Ser Tyr Val Gly Ser Asn Asn
            445                 450                 455
```

-continued

```
GAG TAC AGA ATT AGT TTA GCC AAA AAA TAC GGC GGT TGC CCC GTT ATG      702
Glu Tyr Arg Ile Ser Leu Ala Lys Lys Tyr Gly Gly Cys Pro Val Met
        460                 465                 470

AAT TTG CAC GCT GAA TAC ACT AAT TCC TTT GAA GAT TTC ATT ACC AAC      750
Asn Leu His Ala Glu Tyr Thr Asn Ser Phe Glu Asp Phe Ile Thr Asn
        475                 480                 485

GTA ATT TGG GAG AAC TTC TAC AAA CCA ATT GTT TAC GTA GGC ACT GAT      798
Val Ile Trp Glu Asn Phe Tyr Lys Pro Ile Val Tyr Val Gly Thr Asp
490                 495                 500                 505

TCT GCC GAA GAA GAG GAA ATA CTC CTA GAG GTT TCT TTG ATA TTT AAG      846
Ser Ala Glu Glu Glu Glu Ile Leu Leu Glu Val Ser Leu Ile Phe Lys
                510                 515                 520

ATC AAA GAA TTT GCA CCT GAC GCT CCG CTA TAC ACT GGT CCT GCA TAT      894
Ile Lys Glu Phe Ala Pro Asp Ala Pro Leu Tyr Thr Gly Pro Ala Tyr
                525                 530                 535

TAAACTTGCG ATTCAGTTGA CATCGTCAAT TTGTAACTCA TAATTTTATC TAAATTCGAT    954

CGCAATTCTT GTAATTTTTG ATTGGTCGGT TTGGTTCCTA ATGCCGACAC CACATTAGCT   1014

AACGCTTTAT CGTACTGTTT TTTGAATGTC AAATCTTCCA CCGCCATAAT GAATTGTTGT   1074

AAATTTCTAT CGGACAATTG AAGTTCGACA TCATCGGATT TGTCCAAAGG ATTATCATAC   1134

GTTTCTTGTA TCAAGTTATC TTCAATAAAT ATTT                               1168
```

(2) INFORMATION FOR SEQ ID NO:6:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO:6:

```
Met Tyr Thr Arg Tyr Ser Tyr Ser Pro Thr Leu Gly Lys Thr Tyr Val
 1               5                  10                  15

Tyr Asp Asn Lys Tyr Phe Lys Asn Leu Gly Ala Val Ile Lys Asn Ala
            20                  25                  30

Lys Arg Lys Lys His Leu Glu Glu His Glu His Glu Glu Arg Asn Leu
        35                  40                  45

Asp Ser Leu Asp Lys Tyr Leu Val Ala Glu Asp Pro Phe Leu Gly Pro
    50                  55                  60

Gly Lys Asn Gln Lys Leu Thr Leu Phe Lys Glu Ile Arg Ser Val Lys
65                  70                  75                  80

Pro Asp Thr Met Lys Leu Val Val Asn Trp Ser Gly Arg Glu Phe Leu
                85                  90                  95

Arg Glu Thr Trp Thr Arg Phe Met Glu Asp Ser Phe Pro Ile Val Asn
            100                 105                 110

Asp Gln Glu Ile Met Asp Val Phe Leu Ser Val Asn Met Arg Pro Thr
        115                 120                 125

Lys Pro Asn Arg Cys Tyr Arg Phe Leu Ala Gln His Ala Leu Arg Cys
    130                 135                 140

Asp Pro Asp Tyr Ile Pro His Glu Val Ile Arg Ile Val Glu Pro Ser
145                 150                 155                 160

Tyr Val Gly Ser Asn Asn Glu Tyr Arg Ile Ser Leu Ala Lys Lys Tyr
                165                 170                 175

Gly Gly Cys Pro Val Met Asn Leu His Ala Glu Tyr Thr Asn Ser Phe
            180                 185                 190
```

```
Glu Asp Phe Ile Thr Asn Val Ile Trp Glu Asn Phe Tyr Lys Pro Ile
        195                 200                 205

Val Tyr Val Gly Thr Asp Ser Ala Glu Glu Glu Ile Leu Leu Glu
    210                 215                 220

Val Ser Leu Ile Phe Lys Ile Lys Glu Phe Ala Pro Asp Ala Pro Leu
225                 230                 235                 240

Tyr Thr Gly Pro Ala Tyr
                245
```

(2) INFORMATION FOR SEQ ID NO:7:

(i) SEQUENCE CHARACTERISTICS:
        (A) LENGTH: 5820 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1388..1973

(ix) FEATURE:
        (A) NAME/KEY: CDS
        (B) LOCATION: 2083..2820

(ix) FEATURE:
        (A) NAME/KEY: CDS
        (B) LOCATION: 4074..4875

(ix) FEATURE:
        (A) NAME/KEY: CDS
        (B) LOCATION: complement (5..317)

(ix) FEATURE:
        (A) NAME/KEY: CDS
        (B) LOCATION: complement (651..1194)

(ix) FEATURE:
        (A) NAME/KEY: CDS
        (B) LOCATION: complement (2821..3790)

(ix) FEATURE:
        (A) NAME/KEY: CDS
        (B) LOCATION: complement (5004..5820)

(xi) SEQUENCE DESCRIPTION: SEQ ID NO:7:

```
CTCGAGAATG TTGGTTTATC TGTGACTAAA GGTACGGGCC ATTTTCGGTT AGCATCGATT      60

TGTACTAAGT CGGGATTCAT TGCAACCGCA CTGTGATCAA TGGCGTTATT TTTTTCAATC     120

AATTCAATAA TTTGTCTGTA TATGTATGTT TGCAAATCGT GAAATATAGT TTCGCTGTTC     180

TCGCAACGGG TTAAATTTTT ATTCTTGATC CATTCAACTA GATTATTGTA CGAATTGTGC     240

AATTGTACCA GTTCTTCAAA TATAATATTG TGATCGACTT CGATGACAAA ATGCCAAACG     300

TCTTCAACGA ATCTCATTTG ATAGATTTTG TCAAAGTACA AACCAATAGT GCGCGGCAAA     360

GAGATAATTT TTAGCAAATT TGTAGGATCG ATGGCAAAAG ACTCTGTCGT TTCGCGACTC     420

GCGTCAACGA CATAGAAATA GATATAGTAC ACAATAAAAT TTTAGTCAGC TTAGAGCTGG     480

ACAGACTACT YTTTATCGCA ACCANTGTTA CAAAACTGAC GTTGAACACT TTGAACGGTC     540

TACTTTATAT ATTTTCGTAA CCTTATAACT ATTACGAACC GGGTTAATAT AAAAATAACT     600

AGATTAATAA ATGTATGTTT TTATTGTATA AAGATAACAA ATACACATTT ATATTATAAA     660

TCCATAAGGA TTCACATTTT TAGAAGTTAT TAATTCGTTA AAAGTAATAT AATTTCTATA     720

AGTATTTACG TCTGTTACAC AGTAATCGGA GTTATTTGTA GTATTCATAT CTGTGTAAAT     780
```

```
-continued

GTCACAATAC CAAGGTTTTC TAAAAAGTTT GTTTTCGTCG TGACATTTAA ATATATCGGA       840
AAAGCAAAAC CACAAAAAAT CTTTGTTCAA AGCCAAACTA ATATCAGTAA CTAGATTCAA       900
TTTTTCTTCG TCAATATTTT CAAAATTATA AATACGGTA TAGGCAATAC CATAATTGAA        960
CCATTTGTCG TTACGGCACC ATTTTTTCCA TCWTTTTATA TATTGTAGCA TCTGGTTCCA      1020
ATTGATTTCG TCGTTTTTAA CCGCAATTTC GCTTTCGACA GACGAATAAT ACCATCCAGA      1080
CGGTAGAGCA ATACGAATAT GTTCAAATAT AGCCATATAT TCTTTTTCGA TACGAACATT      1140
GTGATACACA ACTTGTAATA GACTCAATGT CAGCAGACTC GATGGTGTAC ACATTTTGTT      1200
AGATTCCTAA CGATGCGAAT GGTGAATAGC ATTATTGTTT AAACGGTTAT ATAGTAATTA      1260
TTAATCTAAT CTTGACATTA TCATTTTATT GATAACAATA GATATGATAA AATTATACTA      1320
TATAAATCAA AACAGAATTC ATTTTAATTA CAGTTTATAC AATTGTACAA ACAGTTTATA      1380
ACCAACCATG TGTAACGTGT GGCCAGTGGT TAACCGTGTG CTTTGCAAAC TAGTCATGCA      1440
AAATTTGTCC AAAATATATG GCAATATACA ATTTTTATAT CTGATGGGCA ACAAGCCAAA      1500
GGAAATTCAA GAGGAACAAG CCAATTTCAA CGAACTATAT TACAAGTTCA AAGTGTTTAG      1560
ATCACAATTG CCCGACATGA ATTGTGAAAC TTTTGCTCAT AAATTGATTG ACCAGAAAAT      1620
ATTGTATTGC AGAGAAAATTC ATAATTTGTA TTTGAACTTT TTATATTGCT TCTACAAACA     1680
ATACTTTGAC ACGCTGAAGA TTGACTGCCA TATTTTAAG GATTTGATAG ATGACGATGT       1740
ACCATTGCAA GATTTTGAAG AGTTAAATGT TGTTCTACTC GACAATAACA TACCAATGTA      1800
TACGGCTTTG TGTGATGATG TGTTTGAAAA GAAAACCATT ATACAAGATA TAGAATATGT      1860
AATGAACAAA ATATGCGTTG AAGGAGCGTA CGTGCCATTT CAAGAAGAAN TTTTGCAATA      1920
TCAAATCTTT TTGCAAGAAT ATGAAGATTT CTGTCGTCGT GTTGAAAATT TGTAATAAAA      1980
CGAAATAAAC CTTTAATATA AATATTAAAC ATACACTTTT ATTTCTAAAA TAAGTATTTT      2040
TTCCCTATTG TTCAAGATTG TGAAAAATCA AATATCCCAT AATGTATACT CGTTACAGTT      2100
ACAGCCCTAC TTTGGGCAAA ACCTATGTGT ACGACAACAA ATACTTTAAG AATTTAGGTG      2160
CTGTTATTAA AAATGCCAAA CGCAAGAAGC ATTTAGAGGA GCACGAACAT GAAGAACGCA      2220
ACTTAGATTC GCTCGACAAA TACTTGGTGG CGGAAGATCC TTTTTTGGGA CCTGGCAAAA      2280
ATCAAAAACT AACTTTGTTT AAAGAGATTC GCAGCGTTAA GCCCGACACA ATGAAGCTTG      2340
TAGTTAACTG GAGCGGTCGC GAATTTCTTC GCGAAACTTG GACTCGTTTC ATGGAAGACA      2400
GTTTTCCCAT TGTAAACGAC CAAGAAATTA TGGACGTGTT TCTGTCTGTT AATATGCGAC      2460
CAACCAAACC GAACCGTTGT TACCGATTCT TAGCGCAACA CGCTCTGCGT TGTGATCCCG      2520
ACTATATTCC TCACGAAGTC ATTCGTATTG TAGAACCTTC CTATGTAGGC AGTAACAACG      2580
AGTACAGAAT TAGTTTAGCC AAAAAATACG GCGGTTGCCC CGTTATGAAT TTGCACGCTG      2640
AATACACTAA TTCCTTTGAA GATTTCATTA CCAACGTAAT TTGGGAGAAC TTCTACAAAC      2700
CAATTGTTTA CGTAGGCACT GATTCTGCCG AAGAAGAGGA AATACTCCTA GAGGTTTCTT      2760
TGATATTTAA GATCAAAGAA TTTGCACCTG ACGCTCCGCT ATACACTGGT CCTGCATATT      2820
AAACTTGCGA TTCAGTTGAC ATCGTCAATT TGTAACTCAT AATTTTATCT AAATTCGATC      2880
GCAATTCTTG TAATTTTTGA TTGGTCGGTT TGGTTCCTAA TGCCGACACC ACATTAGCTA      2940
ACGCTTTATC GTACTGTTTT TTGAATGTCA AATCTTCCAC CGCCATAATG AATTGTTGTA      3000
AATTTCTATC GGACAATTGA AGTTCGACAT CATCGGATTT GTCCAAAGGA TTATCATACG      3060
TTTCTTGTAT CAAGTTATCT TCAATAAATA TTTGTAGTTT AGCAGAAACC TGTTGTGTTT      3120
GTGCATTCGA AAGCCGTTGA TTTAATTGAT TTTTTATTGA TATTAATGTG TCTTGTGCTT      3180
```

```
CAGTAGACAA AGGATAATTT TTTATCCATG AACTGTCCAA TGTTATATTG TACAAAGAAC   3240

GTACATATTG TTTTAATTCG CTGCTGGCTC GCTGCTGTTG TTCGTCGTCG GTCCACCCGT   3300

TTTCCGATTC TGACGAAACT ACAGGACTCG GTTGAACGGC TATGCGTCGT TGTAAAACCT   3360

TTGCAGTAGG ACTGGCGGCG GCGGTAACGG TATTTACTAT CGAGCCATTG GCGGGTTTTA   3420

ATACTTTTTT TAATTTAATT CCTTTCTGTA TTTGTTCCAT CAATTCGGTA CGTGGATCTT   3480

TTAAAACTTG CCGAGTCGAC GTTGTATAAT CGCGATCTTT ACTGGATGGT ATTACTATAT   3540

CTTCTATTAA TGGTAATGAC GGTGGCGGAG GAGGCGGCGG CAAAGGAGGT ATCGTCGAAG   3600

ATAAGTTTGT TTGAGGCGGC GGCGGTGGCG GCGGTATTGG TGGTGGTATT GGTGGCGGCA   3660

TATGTGTTTG CGGCGAGGAA GATTCAGAAT CGATAATTAT TGTTGGCGAA ATTGTTTTTT   3720

GCATTATATC CGATGTCGAC ACAGTTGTCG GTTTAGGTAT TGTTGTTTTA GGGACTGTTG   3780

GTACTGACAT TGTCTGTGAC AATGTTGGTA TAATAATTTG ATCTATCACC AATGTCTATT   3840

AGTACGTCGT TGTTGTATAT TTCTTGGGCC AATTTCAATA ACTGAATACA ATCGTACACG   3900

TTTAATTGTA TCCGATCAGA ATTGGACTGA GCGACAGCGC TGACCGTACG TTTCAAACCT   3960

GTGCGGCGCC GAGTTCATGC GCAGTAGAAA GTCGACATTA TTGATGTTTG TGTAGTTTTT   4020

TTCAGCCAAA TATTGTTGAA CACTTTGCAG TTGAACCATT ATCGCGAATC GCAATGGACG   4080

ACCGTTTCGT TAAGGAAATA AACCAATTTT TCGCCGAAAT AAAAATACAA AACAATGTGC   4140

GTTTGGTCGA CGGCAAGTTT GGCAAAATGT GTGTTATCAA ACACGAGCCC ACGGGCAAAC   4200

TGTTCGTAAA AAAGAGTGTC GCAATTAAAT ATGTGACCGA GATCGAACCT ATGGTGCATC   4260

AACTAATGAA GGACAACCGA TATTTCATCA AATTATATTA CTCGTTGACA ACGTTAAAAT   4320

CTCAAATACT AATATTAGAT TACGTTGCTG GAGGCGATTT GTTTGATTTT TAAAAAAAC   4380

ACAAAAAAGT ATCTGAAGCG GAAACACGTT CAATAGTGGG TCAATTAACC GAAGCACNSA   4440

ACGCGCTTCA CGCTTACAAA TTABAACATA ACGATCTCAA ACTCGAAAAC GTCCTATACG   4500

TACGTCATAA ACAAATTTAT TTGTGTGATT ATGGACTGTG TAAAATTGTC AACACGAGTT   4560

CGTGTCGAGA CGGCACAAAG GAGTACATGT CTCCGGAGAA GCTCAAACGA CAAAATTACG   4620

ATGTTCACGT CGATTGGTGG GCTTTGGGCA TCTTGACGTA TGAACTTTTA ATTGGACATC   4680

ATCCCTACAA ACATAGCAAC GACAACGAAG AAGATTTCGA TTTGGATGTA CTACAACAGA   4740

GACAACAAAA AAAACTTCAC AAATACAATT TTCTAAGTAG TGACGCTCAA AAATTTTTGG   4800

AAGCAATGTT AATGTATAAC NTTAATTACA GGTTGTGTAC ATACGAGACT GTAATAAAAC   4860

ACGGTTTTTT ATCATAATAT ATATTTAATA AAAAGAATA ATGTTGTTTC TTTATTACCA   4920

TTACAACTAA NTTATAAAAT ATTACAAAAN TTTATTTACA ATCTATTAAA ACNAAAATAT   4980

TATGATATTA TAAAAGTTAC ATTAAATATT ATCTGCTTTG CGAGCACGTG AAGTGCGTTG   5040

ACGTTTAGCT GGTGGTTCTT CAGTACGAAG AACKGGTACT CTAACCATAC GAAAAGTAGC   5100

TATCTGAGGT TTCATGTTAT CTGCCCATTG CACKATTTCA ACCKCATCGT CACTATCGTC   5160

ATTGACGAAC CTAGCAGGGC TTAAAGGTAA ATTTAAACAT TCAACATCAG ACATATCGAC   5220

AGGTTCTTGT TTGGAACAC ATTCTTCATG ATACTCATTA ATATAATCAG GATTTTCACA   5280

TTCAGTATTA AAATCATCCC CAAACAATTC TTTTTTTATG GCAATGTCAA ATGGTGCAGC   5340

GTCATTATTA TCATCAGTAG TGTTAGCATC CTTTGATGTT TTTTCTGTTT TAACAGTGAT   5400

ATGCTCGAAA TATTTGCCAT TTTTGTCTAC ATTGGTACTT TTAGCTAATT CTTTATCGAT   5460

ACTATCAAGT TCTTCAGTAC TCATTGCAAC TGGTAACACT GTCGTTGATG ATAGTTCTTT   5520
```

```
TTCAAGCAGA TTGCGCACTT CATTTTCAAT TTGACTTATT TCGTTCAATT GTGACACAAT      5580

TACTTCTGAA GCTTTCAATT GCTCTGGACT AGTTTTAGAC AATTTTTGTT TTGGTTGCAA      5640

AGCAAATTCA TTCATATTAC TATTATTATT ACTATTAGAA GAAGGAAACA CGTTATCGGA      5700

TGCGTTATCA CAATGATTGT CTATAACAGT ACGAGACAAA TTAGTAATAT TTACAATAGG      5760

AAGAGATAAA TTAGAAATAT CATCATCATC GACGCTGTTC TNGTCATTAT CATTTTTNGA      5820
```

(2) INFORMATION FOR SEQ ID NO:8:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TTTTGCAAGA ATATGAAGAT TTCTCTCGTC GTGTTGAAAA TTTGTAATAA AACTAAATAA       60

ACCTTTAATA TAAATATTAA ACATACACTT TTATTTCTAA AATAAGTATT TTTTTCCTAT      120

TGTTCAAGAT TGTGAAAAAT CAAATATCCC ATAATGTATA CTCGTTACAG TTACAGCCCT      180

ACTTTGGGCA AAACCTATGT GTACGACAAC AAATACTTTA AGAATTTAGG TGCTGTTATT      240

AAAAATGCCA AACGCAAGAA GCATTTAGAG GAGCACGAAC ATGAAGAACG CAACTTGGAT      300

TCGCTCGACA AATACTTGGT GGCGGAAGAT CCTTTTTTGG GACCTGGCAA AAATCAAAAA      360

CTAACTTTGT TTAAAGAGAT TCGCAGCGTT AAGCCCGACA CAATGAAGCT T               411
```

(2) INFORMATION FOR SEQ ID NO:9:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TTTTGCAAGA ATATGAAGAT TTCTCTCGTC GTGTTGAAAA TTTGTAATAA AACTAAATAA       60

ACCTTTAATA TAAATATTAA ACATACACTT TTATTTCTAA AATAAGTATT TTTTTCCTAT      120

TGTTCAAGAT TGTGAAAAAT CAAATATCCC ATAATGTATA CTCGTTACAG TTACAGCCCT      180

ACTTTGGGCA AAACCTATGT GTACGACAAC AAATACTTTA AGAATTTAGG TGCTGTTATT      240

AAAAATGCCA AACGCAAGAA GCATTTAGAG GAGCACGAAC ATGAAGAACG CAACTTAGAT      300

TCGCTCGACA AATACTTGGT GGCGGAAGAT CCTTTTTTGG GACCTGGCAA AAATCAAAAA      360

CTAACTTTGT TTAAAGAGAT TCGCAGCGTT AAGCCCGACA CAATGAAGCT T               411
```

(2) INFORMATION FOR SEQ ID NO:10:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TTTTGCAAGA ATATGAAGAT TTCTCTCGTC GTGTTGAAAA TTTGTAATAA AACTAAATAA       60
```

```
ACCTTTAATA TAAATATTAA ACATACACTT TTATTTCTAA AATAAGTATT TTTTTCCTAT      120

TGTTCAAGAT TGTGAAAAAT CAAATATCCC ATAATGTATA CTCGTTACAG TTACAGCCCT      180

ACTTTGGGCA AAACCTATGT GTACGACAAC AAATACTTTA AGAATTTAGG TGCTGTTATT      240

AAAAATGCCA AACGCAAGAA GCATTTAGAG GAGCACGAAC ATGAAGAACG CAACTTAGAT      300

TCGCTCGACA AATACTTGGT GGCGGAAGAT CCTTTTTTGG GACCTGGCAA AAATCAAAAA      360

CTAACTTTGT TTAAAGAGAT TCGCAGCGTT AAGCCCGACA CAATGAAGCT T              411
```

(2) INFORMATION FOR SEQ ID NO:11:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
TTTTGCAAGA ATATGAAGAT TTCTCTCGTC GTGTTGAAAA TTTGTAATAA AACCAAATAA       60

ACCTTTAATA TNNNNNNTAA ACATACACTT TTATTTCTAA AATAAGTATT TTTTTCCTAT      120

TGTTCAAGAT TGTGAAAAAT CAAATATCCC ATAATGTATA CTCGTTACAG TTACAGCCCT      180

ACTTTGGGCA AAACCTATGT GTACGACAAC AAATACTTTA AGAATTTAGG TGCTGTTATT      240

AAAAATGCCA AACGCAAGAA GCATTTAGAG GAGCACGAAC ATGAAGAACG CAACTTGGAT      300

TCGCTCGACA AATACTTGGT GGCGGAAGAT CCTTTTTTGG GACCTGGCAA AAATCAAAAA      360

CTAACTTTGT TTAAAGAGAT TCGCAGCGTT AAGCCCGACA CAATGAAGCT T              411
```

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TATGAAGATA TCTGTCGT                                                    18
```

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
TCCCATAAAG GATCCTCGTT ACAG                                             24
```

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GATCGCGGCC GCCCGGGATC CGAGCTC                                        27

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GATCGAGCTC GGATCCCGGG CGGCCGC                                        27

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GTAGGGCTGT AACTGTAACG                                                20

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

AATTCAGATC TCCCGGGC                                                  18

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GGCCGCCCGG GAGATCTG                                                  18

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GTTTGTGGGA TCCGAAAGC                                                 19

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GTTTCGGATC CACAAACA                                                            18

(2) INFORMATION FOR SEQ ID NO:21:

(i) SEQUENCE CHARACTERISTICS:
        (A) LENGTH: 104 amino acids
        (B) TYPE: amino acid
        (D) TOPOLOGY: linear (ii) MOLECULE TYPE: protein (xi) SEQUENCE DESCRIPTION: SEQ ID NO:21:

Met Arg Phe Val Glu Asp Val Trp His Phe Val Ile Glu Val Asp His
1               5                     10                15

Asn Ile Ile Phe Glu Glu Leu Val Gln Leu His Asn Ser Tyr Asn Asn
                20                     25                   30

Leu Val Glu Trp Ile Lys Asn Lys Asn Leu Thr Arg Cys Glu Asn Ser
             35                    40                   45

Glu Thr Ile Phe His Asp Leu Gln Thr Tyr Ile Tyr Arg Gln Ile Ile
        50                     55                   60

Glu Leu Ile Glu Lys Asn Ala Ile Asp His Ser Ala Val Ala Met Asn
65              70                     75                80

Pro Asp Leu Val Gln Ile Asp Ala Asn Arg Lys Trp Pro Val Pro Leu
                85                     90                   95

Val Thr Asp Lys Pro Thr Phe Ser
             100

(2) INFORMATION FOR SEQ ID NO:22:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO:22:

Met Cys Thr Pro Ser Ser Leu Leu Thr Leu Ser Leu Leu Gln Val Val
1               5                     10                15

Tyr His Asn Val Arg Ile Glu Lys Glu Tyr Met Ala Ile Phe Glu His
                20                     25                   30

Ile Arg Ile Ala Leu Pro Ser Gly Trp Tyr Tyr Ser Ser Val Glu Ser
             35                    40                   45

Glu Ile Ala Val Lys Asn Asp Glu Ile Asn Trp Asn Gln Met Leu Gln
        50                     55                   60

Tyr Ile Lys Xaa Trp Lys Lys Trp Cys Arg Asn Asp Lys Trp Phe Asn
65              70                     75                80

Tyr Gly Ile Ala Tyr Thr Val Phe Tyr Asn Phe Glu Asn Ile Asp Glu
                85                     90                   95

```
Glu Lys Leu Asn Leu Val Tyr Asp Ile Ser Leu Ala Leu Asn Lys Asp
                100                 105                 110

Phe Leu Trp Phe Cys Phe Ser Asp Ile Phe Lys Cys His Asp Glu Asn
            115                 120                 125

Lys Leu Phe Arg Lys Pro Trp Lys Cys Asp Ile Lys Thr Asp Met Asn
        130                 135                 140

Thr Thr Asn Asn Ser Asp Tyr Cys Val Thr Asp Val Asn Thr Tyr Arg
145                 150                 155                 160

Asn Tyr Ile Thr Phe Asn Glu Leu Ile Thr Ser Lys Met Cys Asn Pro
                165                 170                 175

Lys Gly Phe Ile Ile
            180

(2) INFORMATION FOR SEQ ID NO:23:

(i) SEQUENCE CHARACTERISTICS:
        (A) LENGTH: 195 amino acids
        (B) TYPE: amino acid
        (D) TOPOLOGY: linear (ii) MOLECULE TYPE: protein (xi) SEQUENCE DESCRIPTION: SEQ ID NO:23:

Met Cys Asn Val Trp Pro Val Val Asn Arg Val Leu Cys Lys Leu Val
 1               5                  10                  15

Met Gln Asn Leu Ser Lys Ile Tyr Gly Asn Ile Gln Phe Leu Tyr Leu
             20                  25                  30

Met Gly Asn Lys Pro Lys Glu Ile Gln Glu Gln Ala Asn Phe Asn
         35                  40                  45

Glu Leu Tyr Tyr Lys Phe Lys Val Phe Arg Ser Gln Leu Pro Asp Met
     50                  55                  60

Asn Cys Glu Thr Phe Ala His Lys Leu Ile Asp Gln Lys Ile Leu Tyr
 65                  70                  75                  80

Cys Arg Glu Ile His Asn Leu Lys Leu Asn Phe Leu Tyr Cys Phe Tyr
                 85                  90                  95

Lys Gln Tyr Phe Asp Thr Leu Lys Ile Asp Cys His Ile Phe Lys Asp
             100                 105                 110

Leu Ile Asp Asp Asp Val Pro Leu Gln Asp Phe Glu Leu Asn Val
         115                 120                 125

Val Leu Leu Asp Asn Asn Ile Pro Met Tyr Thr Ala Leu Cys Asp Asp
130                 135                 140

Val Phe Glu Lys Lys Thr Ile Ile Gln Asp Ile Glu Tyr Val Met Asn
145                 150                 155                 160

Lys Ile Cys Val Glu Gly Ala Tyr Val Pro Phe Gln Glu Xaa Leu
                165                 170                 175

Gln Tyr Gln Ile Phe Leu Gln Glu Tyr Glu Asp Phe Cys Arg Arg Val
             180                 185                 190

Glu Asn Leu
        195

(2) INFORMATION FOR SEQ ID NO:24:

(i) SEQUENCE CHARACTERISTICS:
        (A) LENGTH: 246 amino acids
        (B) TYPE: amino acid
        (D) TOPOLOGY: linear (ii) MOLECULE TYPE: protein
```

(xi) SEQUENCE DESCRIPTION: SEQ ID NO:24:

```
Met Tyr Thr Arg Tyr Ser Tyr Ser Pro Thr Leu Gly Lys Thr Tyr Val
 1               5                  10                  15

Tyr Asp Asn Lys Tyr Phe Lys Asn Leu Gly Ala Val Ile Lys Asn Ala
             20                  25                  30

Lys Arg Lys Lys His Leu Glu Glu His Glu His Glu Glu Arg Asn Leu
         35                  40                  45

Asp Ser Leu Asp Lys Tyr Leu Val Ala Glu Asp Pro Phe Leu Gly Pro
     50                  55                  60

Gly Lys Asn Gln Lys Leu Thr Leu Phe Lys Glu Ile Arg Ser Val Lys
65                  70                  75                  80

Pro Asp Thr Met Lys Leu Val Val Asn Trp Ser Gly Arg Glu Phe Leu
                 85                  90                  95

Arg Glu Thr Trp Thr Arg Phe Met Glu Asp Ser Phe Pro Ile Val Asn
            100                 105                 110

Asp Gln Glu Ile Met Asp Val Phe Leu Ser Val Asn Met Arg Pro Thr
        115                 120                 125

Lys Pro Asn Arg Cys Tyr Arg Phe Leu Ala Gln His Ala Leu Arg Cys
130                 135                 140

Asp Pro Asp Tyr Ile Pro His Glu Val Ile Arg Ile Val Glu Pro Ser
145                 150                 155                 160

Tyr Val Gly Ser Asn Asn Glu Tyr Arg Ile Ser Leu Ala Lys Lys Tyr
                165                 170                 175

Gly Gly Cys Pro Val Met Asn Leu His Ala Glu Tyr Thr Asn Ser Phe
            180                 185                 190

Glu Asp Phe Ile Thr Asn Val Ile Trp Glu Asn Phe Tyr Lys Pro Ile
        195                 200                 205

Val Tyr Val Gly Thr Asp Ser Ala Glu Glu Glu Ile Leu Leu Glu
    210                 215                 220

Val Ser Leu Ile Phe Lys Ile Lys Glu Phe Ala Pro Asp Ala Pro Leu
225                 230                 235                 240

Tyr Thr Gly Pro Ala Tyr
                245
```

(2) INFORMATION FOR SEQ ID NO:25:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:25:

```
Met Ser Val Pro Thr Val Pro Lys Thr Thr Ile Pro Lys Pro Thr Thr
 1               5                  10                  15

Val Ser Thr Ser Asp Ile Met Gln Lys Thr Ile Ser Pro Thr Ile Ile
             20                  25                  30

Ile Asp Ser Glu Ser Ser Pro Gln Thr His Met Pro Pro Pro Ile
         35                  40                  45

Pro Pro Pro Ile Pro Pro Pro Pro Pro Pro Gln Thr Asn Leu Ser
     50                  55                  60

Ser Thr Ile Pro Pro Leu Pro Pro Pro Pro Pro Ser Leu Pro
65                  70                  75                  80

Leu Ile Glu Asp Ile Val Ile Pro Ser Ser Lys Asp Arg Asp Tyr Thr
                 85                  90                  95
```

```
Thr Ser Thr Arg Gln Val Leu Lys Asp Pro Arg Thr Glu Leu Met Glu
            100                 105                 110

Gln Ile Gln Lys Gly Ile Lys Leu Lys Lys Val Leu Lys Pro Ala Asn
        115                 120                 125

Gly Ser Ile Val Asn Thr Val Thr Ala Ala Ser Pro Thr Ala Lys
130                 135                 140

Val Leu Gln Arg Arg Ile Ala Val Gln Pro Ser Pro Val Val Ser Ser
145                 150                 155                 160

Glu Ser Glu Asn Gly Trp Thr Asp Asp Glu Gln Gln Arg Ala Ser
                165                 170                 175

Ser Glu Leu Lys Gln Tyr Val Arg Ser Leu Tyr Asn Ile Thr Leu Asp
            180                 185                 190

Ser Ser Trp Ile Lys Asn Tyr Pro Leu Ser Thr Glu Ala Gln Asp Thr
        195                 200                 205

Leu Ile Ser Ile Lys Asn Gln Leu Asn Gln Arg Leu Ser Asn Ala Gln
210                 215                 220

Thr Gln Gln Val Ser Ala Lys Leu Gln Ile Phe Ile Glu Asp Asn Leu
225                 230                 235                 240

Ile Gln Glu Thr Tyr Asp Asn Pro Leu Asp Lys Ser Asp Asp Val Glu
                245                 250                 255

Leu Gln Leu Ser Asp Arg Asn Leu Gln Gln Phe Ile Met Ala Val Glu
            260                 265                 270

Asp Leu Thr Phe Lys Lys Gln Tyr Asp Lys Ala Leu Ala Asn Val Val
        275                 280                 285

Ser Ala Leu Gly Thr Lys Pro Thr Asn Gln Lys Leu Gln Glu Leu Arg
290                 295                 300

Ser Asn Leu Asp Lys Ile Met Ser Tyr Lys Leu Thr Met Ser Thr Glu
305                 310                 315                 320

Ser Gln Val (2) INFORMATION FOR SEQ ID NO:26:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO:26:

Met Asp Asp Asp Arg Phe Val Lys Glu Ile Asn Gln Phe Phe Ala Glu
1               5                   10                  15

Ile Lys Ile Gln Asn Asn Val Arg Leu Val Asp Gly Lys Phe Gly Lys
            20                  25                  30

Met Cys Val Ile Lys His Glu Pro Thr Gly Lys Leu Phe Val Lys Lys
        35                  40                  45

Ser Val Ala Ile Lys Tyr Val Thr Glu Ile Glu Pro Met Val His Gln
    50                  55                  60

Leu Met Lys Asp Asn Arg Tyr Phe Ile Lys Leu Tyr Ser Leu Thr
65              70                  75                  80

Thr Leu Lys Ser Gln Ile Leu Ile Leu Asp Tyr Val Ala Gly Gly Asp
            85                  90                  95

Leu Phe Asp Phe Leu Lys Lys His Lys Lys Val Ser Glu Ala Glu Thr
                100                 105                 110

Arg Ser Ile Val Gly Gln Leu Thr Glu Ala Xaa Asn Ala Leu His Ala
```

```
                115                 120                     125
Tyr Lys Leu Xaa His Asn Asp Leu Lys Leu Glu Asn Val Leu Tyr Val
            130                 135                 140

Arg His Lys Gln Ile Tyr Leu Cys Asp Tyr Gly Leu Cys Lys Ile Val
145                 150                 155                 160

Asn Thr Ser Ser Cys Arg Asp Gly Thr Lys Glu Tyr Met Ser Pro Glu
                165                 170                 175

Lys Leu Lys Arg Gln Asn Tyr Asp Val His Val Asp Trp Trp Ala Leu
            180                 185                 190

Gly Ile Leu Thr Tyr Glu Leu Leu Ile Gly His His Pro Tyr Lys His
            195                 200                 205

Ser Asn Asp Asn Glu Glu Asp Phe Asp Leu Asp Val Leu Gln Gln Arg
210                 215                 220

Gln Gln Lys Lys Leu His Lys Tyr Asn Phe Leu Ser Ser Asp Ala Gln
225                 230                 235                 240

Lys Phe Leu Glu Ala Met Leu Met Tyr Asn Xaa Asn Tyr Arg Leu Cys
                245                 250                 255

Thr Tyr Glu Thr Val Ile Lys His Gly Phe Leu Ser (2) INFORMATION FOR SEQ ID NO:27:

(i) SEQUENCE CHARACTERISTICS:
        (A) LENGTH: 272 amino acids
        (B) TYPE: amino acid
        (D) TOPOLOGY: linear (ii) MOLECULE TYPE: protein (xi) SEQUENCE DESCRIPTION: SEQ ID NO:27:

Ser Lys Asn Asp Asn Asp Xaa Asn Ser Val Asp Asp Asp Asp Ile Ser
1               5                   10                  15

Asn Leu Ser Leu Pro Ile Val Asn Ile Thr Asn Leu Ser Arg Thr Val
                20                  25                  30

Ile Asp Asn His Cys Asp Asn Ala Ser Asp Asn Val Phe Pro Ser Ser
            35                  40                  45

Asn Ser Asn Asn Asn Ser Asn Met Asn Glu Phe Ala Leu Gln Pro Lys
        50                  55                  60

Gln Lys Leu Ser Lys Thr Ser Pro Glu Gln Leu Lys Ala Ser Glu Val
65                  70                  75                  80

Ile Val Ser Gln Leu Asn Glu Ile Ser Gln Ile Glu Asn Glu Val Arg
                85                  90                  95

Asn Leu Leu Glu Lys Glu Leu Ser Ser Thr Thr Val Leu Pro Val Ala
            100                 105                 110

Met Ser Thr Glu Glu Leu Asp Ser Ile Asp Lys Glu Leu Ala Lys Ser
        115                 120                 125

Thr Asn Val Asp Lys Asn Gly Lys Tyr Phe Glu His Ile Thr Val Lys
    130                 135                 140

Thr Glu Lys Thr Ser Lys Asp Ala Asn Thr Thr Asp Asp Asn Asn Asp
145                 150                 155                 160

Ala Ala Pro Phe Asp Ile Ala Ile Lys Lys Glu Leu Phe Gly Asp Asp
                165                 170                 175

Phe Asn Thr Glu Cys Glu Asn Pro Asp Tyr Ile Asn Glu Tyr His Glu
            180                 185                 190

Glu Cys Val Pro Lys Gln Glu Pro Val Asp Met Ser Asp Val Glu Cys
        195                 200                 205
```

-continued

```
Leu Asn Leu Pro Leu Ser Pro Ala Arg Phe Val Asn Asp Asp Ser Asp
        210             215                 220

Asp Xaa Val Glu Ile Val Gln Trp Ala Asp Asn Met Lys Pro Gln Ile
225             230                 235                 240

Ala Thr Phe Arg Met Val Arg Val Pro Val Leu Arg Thr Glu Glu Pro
                245                 250                 255

Pro Ala Lys Arg Gln Arg Thr Ser Arg Ala Arg Lys Ala Asp Asn Ile
            260                 265                 270
```